(12) United States Patent
Baker et al.

(10) Patent No.: US 7,485,732 B2
(45) Date of Patent: Feb. 3, 2009

(54) SUBSTITUTED 3-ALKYL AND 3-ALKENYL AZETIDINE DERIVATIVES

(75) Inventors: Robert K. Baker, Cranford, NJ (US); Jianming Bao, Scotch Plains, NJ (US); Shouwu Miao, Edison, NJ (US); Kathleen M. Rupprecht, Cranford, NJ (US)

(73) Assignee: Merck & Co., Inc., Rahway, NJ (US)

(*) Notice: Subject to any disclaimer, the term of this patent is extended or adjusted under 35 U.S.C. 154(b) by 66 days.

(21) Appl. No.: 10/557,246

(22) PCT Filed: Jun. 9, 2004

(86) PCT No.: PCT/US2004/018348

§ 371 (c)(1), (2), (4) Date: Nov. 15, 2005

(87) PCT Pub. No.: WO2005/000809

PCT Pub. Date: Jan. 6, 2005

(65) Prior Publication Data

US 2006/0293299 A1    Dec. 28, 2006

Related U.S. Application Data

(60) Provisional application No. 60/477,850, filed on Jun. 11, 2003.

(51) Int. Cl.
*C07D 205/04* (2006.01)
(52) U.S. Cl. ........................................... 548/960
(58) Field of Classification Search ............ 514/210.19, 514/210.2; 548/950
See application file for complete search history.

(56) References Cited

U.S. PATENT DOCUMENTS

| | | | |
|---|---|---|---|
| 4,052,383 A | 10/1977 | Gold et al. | |
| 4,133,881 A | 1/1979 | Cale et al. | |
| 4,242,261 A | 12/1980 | Cale | |
| 6,355,631 B1 | 3/2002 | Achard et al. | |
| 6,479,479 B2 | 11/2002 | Achard et al. | |
| 6,518,264 B2 | 2/2003 | Achard et al. | |
| 6,858,603 B2 | 2/2005 | Achard et al. | |
| 6,872,717 B2 * | 3/2005 | Achard et al. | 514/210.17 |
| 2002/0016337 A1 | 2/2002 | Cuny et al. | |
| 2003/0055033 A1 | 3/2003 | Achard et al. | |

FOREIGN PATENT DOCUMENTS

| | | |
|---|---|---|
| EP | 1328269 | 5/2004 |
| WO | WO 97/46511 | 12/1997 |
| WO | WO 99/04794 | 2/1999 |
| WO | WO 00/15609 | 3/2000 |
| WO | WO 00/71518 | 11/2000 |
| WO | WO 01/64632 | 9/2001 |
| WO | WO 01/64633 | 9/2001 |
| WO | WO 01/64634 | 9/2001 |
| WO | WO 01/64676 | 9/2001 |
| WO | WO 02/12187 | 2/2002 |
| WO | WO 03/007939 | 1/2003 |
| WO | WO 03/018060 | 3/2003 |
| WO | WO 03/020314 | 3/2003 |
| WO | WO 2004/056800 | 7/2004 |
| WO | WO 2004/096763 | 11/2004 |
| WO | WO 2004/096794 | 11/2004 |
| WO | WO 2005/000809 | 1/2005 |
| WO | WO 2005/077897 | 8/2005 |

OTHER PUBLICATIONS

U.S. Appl. No. 11/602,577.*
Lange et al., Drug Discovery Today, vol. 10 (2005), pp. 693-702, "Medicinal chemistry strategies to CB1 cannabinoind receptor antagonists".
Adam et al., Exp. Opin. Ther. Patents, vol. 12 (2002), pp. 1475-1489, "Recent advances in the cannabinoids".

* cited by examiner

*Primary Examiner*—Kamal A Saeed
*Assistant Examiner*—Yong Chu
(74) *Attorney, Agent, or Firm*—Baerbel R. Brown; Catherine D. Fitch

(57) ABSTRACT

Novel compounds of the structural formula (I) are antagonists and/or inverse agonists of the Cannabinoid-1 (CB1) receptor and are useful in the treatment, prevention and suppression of diseases mediated by the CB1 receptor. The compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, the treatment of obesity or eating disorders, as well as the treatment of asthma, constipation, chronic intestinal pseudo-obstruction, and cirrhosis of the liver.

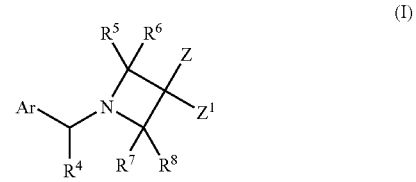

(I)

1 Claim, No Drawings

SUBSTITUTED 3-ALKYL AND 3-ALKENYL AZETIDINE DERIVATIVES

CROSS-REFERENCE TO RELATED APPLICATIONS

This application is a U.S. National Phase application under 35 U.S.C. §371 of PCT Application No. PCT/US2004/018348, filed Jun. 9, 2004, which claims priority under 35 U.S.C. §119 from U.S. Provisional Application No. 60/477,850, filed Jun. 11, 2003.

BACKGROUND OF THE INVENTION

Marijuana (*Cannabis sativa L.*) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

There are at least two CB1 modulators characterized as an inverse agonista or an antagonists, N-(1-piperidinyl)-5-(4-chlorophenyl)-1-(2,4-dichlorophenyl)-4-methylpyrazole-3-carboxamide (SR141716A), and 3-(4-chlorophenyl-N'-(4-chlorophenyl)sulfonyl-N-methyl-4-phenyl-4,5-dihydro-1H-pyrazole-1-carboxamide (SLV-319), in clinical trials for treatment of eating disorders and/or smoking cessation at this time. There still remains a need for potent low molecular weight CB1 modulators that have pharmacokinetic and pharmacodynamic properties suitable for use as human pharmaceuticals.

U.S. Pat. Nos. 5,624,941, 6,028,084, and 6,509,367, PCT Publications WO98/31227, WO98/41519, WO98/43636 and WO98/43635, and EP-658546 disclose substituted pyrazoles having activity against the cannabinoid receptors.

U.S. Pat. Nos. 6,355,631, U.S. Pat. No. 6,479,479 and PCT publications WO 01/64632, 01/64633, and 01/64634 are directed to azetidine derivatives as cannabinoid antagonists.

Other cannabinoid receptor modulating compounds are disclosed in U.S. Pat. Nos. 4,973,587, 5,013,837, 5,081,122, 5,112,820, 5,292,736, and 5,532,237, and PCT publications WO 97/29079, WO 98/37061, WO 99/02499, WO 00/10967, WO 00/10968, WO 01/58869, WO 01/70700, WO 02/076949, WO 03/026647, WO 03/026648, WO 03/027069, WO 03/027076, WO 03/027114, and WO 03/077847.

SUMMARY OF THE INVENTION

The present invention is concerned with substituted 3-alkyl and 3-alkenyl azetidine derivatives of general formula I:

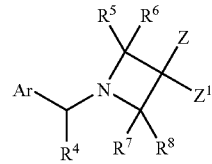

(I)

and pharmaceutically acceptable salts thereof which are modulators of and, in particular, antagonists and/or inverse agonists of the Cannabinoid-1 (CB1) receptor and are useful in the treatment, prevention or suppression of diseases mediated by the Cannabinoid-1 (CB 1) receptor. In one aspect, the invention is concerned with the use of these novel compounds to selectively antagonize the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine, including smoking cessation. The compounds are also useful for the treatment of obesity or eating disorders associated with excessive food intake and complications associated therewith, including left ventricular hypertrophy. The compounds are also useful for the treatment of constipation and chronic intestinal pseudo-obstruction. The compounds are also useful for the treatment of cirrhosis of the liver. The compounds are also useful for the treatment of asthma.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals.

The invention is also concerned with pharmaceutical formulations comprising one of the compounds as an active ingredient.

The invention is further concerned with processes for preparing the compounds of this invention.

DETAILED DESCRIPTION OF THE INVENTION

The compounds used in the methods of the present invention are represented by structural formula I:

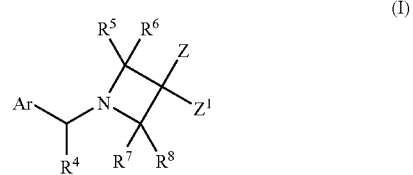

(I)

wherein:
Ar is selected from:
(1) phenyl, and
(2) pyridyl;
wherein phenyl and pyridyl are unsubstituted or substituted with one or two $R^c$ substituents;
$R^4$ is selected from:
(1) $C_{1-6}$alkyl, straight chain or branched,
(2) $C_{2-6}$alkenyl, straight chain or branched,
(3) $C_{2-6}$alkynyl, straight chain or branched,
(4) $C_{3-7}$cycloalkyl,
(5) phenyl, and
(6) heteroaryl;
wherein alkyl, alkenyl, and alkynyl are unsubstituted or substituted with one to three $R^b$ substituents, and cycloalkyl, phenyl and heteroaryl are unsubstituted or substituted with one or two $R^c$ substituents;
$R^5$, $R^6$, $R^7$, and $R^8$ are each independently selected from: hydrogen, $C_{1-6}$ alkyl, unsubstituted or substituted with $R^b$, and $C_{2-6}$ alkenyl, unsubstituted or substituted with $R^b$;
Z is selected from hydrogen, hydroxy, fluoro, methyl, and $-N(R^{11})(R^{12})$, and $Z^1$ is selected from:

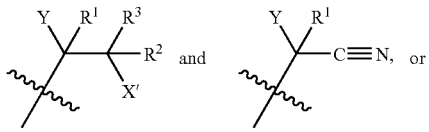

Z and $Z^1$ together form:

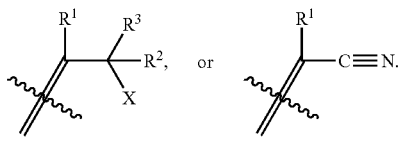

X and X' are independently selected from:
(1) hydroxy,
(2) $C_{1-6}$alkyl, straight chain or branched, unsubstituted or substituted with one to two $R^b$ substituents,
(3) perfluoro $C_{1-6}$alkyl,
(4) $C_{2-6}$alkenyl, straight chain or branched, unsubstituted or substituted with one to two $R^b$ substituents,
(5) $C_{2-6}$alkyl, straight chain or branched, unsubstituted or substituted with one to two $R^b$ substituents,
(6) cyano,
(7) $-C(O)R^{10}$,
(8) $-C(O)OR^{10}$,
(9) $-C(O)N(R^{11})(R^{12})$,
(10) $-N(R^9)S(O)_nR^{10}$,
(11) $-NR^9C(O)R^{10}$,
(12) $-NR^9C(O)OR10$,
(13) $-N(R11)(R^{12})$,
(14) $-S(O)_nR^{10}$,
(15) $-OR^{10}$,
(16) $-OC(O)R^{10}$, and
(17) $-OC(O)N(R^{11})(R^{12})$;
Y is selected from:
(1) hydrogen,
(2) hydroxy,
(3) $C_{1-3}$ alkyloxy,
(4) fluoro,
(5) $C_{1-3}$ alkyl,
(6) trifluoromethyl, and
(7) $-N(R^{11})(R^{12})$;
$R^1$ is selected from:
(1) aryl,
(2) heteroaryl,
(3) $C_{3-7}$ cycloalkyl, and
(4) cycloheteroalkyl,
wherein aryl, heteroaryl, cycloalkyl and cycloheteroalkyl are unsubstituted or substituted with one to three $R^c$ substituents;
$R^2$ is selected from:
(1) hydrogen,
(2) $C_{1-6}$alkyl, straight chain or branched, unsubstituted or substituted with one or two $R^b$ substituents,
(3) fluoro,
(4) hydroxyl,
(5) perfluoro $C_{1-6}$alkyl, straight chain or branched; and
$R^3$ is selected from:
(1) hydrogen,
(2) $C_{1-6}$alkyl, straight chain or branched, unsubstituted or substituted with one or two $R^b$ substituents,
(3) fluoro,
(4) hydroxy,
(5) perfluoro $C_{1-6}$alkyl, straight chain or branched;
or $R^2$ and $R^3$, together with the carbon atom to which they are attached, form a carbonyl group,
or a 3 to 7 membered carbocyclic ring;
provided that when X' is hydroxy, $-NR^9C(O)R^{10}$, $-NR^9C(O)OR^{10}$, $-N(R^{11})(R^{12})$, or $OR^{10}$, then:
(1) $R^2$ and $R^3$ are not both hydrogen, nor
(2) do $R^2$ and $R^3$ form a carbonyl group together with the carbon to which they are attached;
$R^9$ is selected from: hydrogen, $C_{1-6}$alkyl, and $C_{2-6}$alkenyl, straight chain or branched, unsubstituted or substituted with one to three halogen atoms;
$R^{10}$ is selected from:
(1) $C_{1-4}$alkyl, straight chain or branched, unsubstituted or substituted with one to three $R^a$ substituents,
(2) aryl, unsubstituted or substituted with one to three $R^a$ substituents,
(3) aryl $C_{1-4}$alkyl, wherein alkyl is straight or branched chain, unsubstituted or substituted on one, two or three carbon atoms with one to three $R^a$ substituents, and
(4) $-CF_3$;
$R^{11}$ and $R^{12}$ are each independently selected from:
(1) hydrogen,
(2) $C_{1-8}$ alkyl, straight chain or branched, unsubstituted or substituted with one to three substituents selected from $R^a$,
(3) $C_{2-8}$ alkenyl, straight chain or branched,
(4) perfluoro $C_{1-6}$ alkyl, straight chain or branched,
(5) $C_{3-7}$cycloalkyl, unsubstituted or substituted with one to three substituents selected from $R^a$,
(6) cycloalkyl-$C_{1-6}$alkyl, wherein alkyl is straight chain or branched,
(7) cycloheteroalkyl,
(8) aryl, unsubstituted or substituted with one to three substituents selected from $R^a$,
(9) heteroaryl, unsubstituted or substituted on a carbon or nitrogen atom with one to three substituents selected from $R^a$,
(10) aryl $C_{1-6}$alkyl, wherein alkyl is straight chain or branched,
(11) heteroaryl $C_{1-6}$alkyl, wherein alkyl is straight chain or branched, or $R^{11}$ and $R^{12}$ together with the atom(s) to which they are attached form a heterocyclic ring of 4 to 7 members containing 0-2 additional heteroatoms independently selected from oxygen, sulfur and N—$R^9$;

each $R^a$ is independently selected from:
(1) halogen,
(2) N($R^e$)($R^f$),
(3) carboxy,
(4) $C_{1-4}$alkyl,
(5) $C_{1-4}$alkoxy,
(6) aryl,
(7) aryl $C_{1-4}$alkyl,
(8) hydroxy,
(9) $CF_3$,
(10) —OC(O)$C_{1-4}$alkyl, and
(11) aryloxy,
wherein alkyl is straight chain or branched;

each $R^b$ is independently selected from:
(1) halogen,
(2) —$OR^{10}$,
(3) —$CF_3$,
(4) aryl,
(5) heteroaryl,
(6) cyano,
(7) —C(O)$R^{10}$,
(8) —C(O)O$R^{10}$,
(9) —C(O)N($R^e$)($R^f$),
(10) —N($R^9$)S(O)$_n R^{10}$,
(11) —$NR^9$C(O)$R^{10}$,
(12) —$NR^9$C(O)O$R^{10}$,
(13) —N($R^e$)($R^f$),
(14) —S(O)$_n R^{10}$,
(15) —S(O)$_2$O$R^{10}$,
(16) —OC(O)$R^{10}$, n
(17) —OC(O)N($R^e$)($R^f$), y
(18) —$NO_2$,
(19) $C_{3-7}$ cycloalkyl, and
(20) cycloheteroalkyl;
wherein cycloalkyl, cycloheteroalkyl, heteroaryl and aryl are optionally substituted with one to four substituents selected from a group independently selected from $R^d$;

each $R^c$ is independently selected from:
(1) halogen,
(2) —$OR^{10}$,
(3) $CF_3$,
(4) aryl,
(5) heteroaryl,
(6) cyano,
(7) —C(O)$R^{10}$,
(8) —C(O)O$R^{10}$,
(9) —C(O)N($R^{11}$)($R^{12}$),
(10) —N($R^9$)S(O)$_n R^{10}$,
(11) —$NR^9$C(O)$R^{10}$,
(12) —$NR^9$C(O)O$R^{10}$,
(13) —N($R^{11}$)($R^{12}$),
(14) —S(O)$_n R^{10}$,
(15) —S(O)$_2$O$R^{10}$,
(16) —OC(O)$R^{10}$,
(17) —OC(O)N($R^{11}$)($R^{12}$),
(18) —$NO_2$,
(19) $C_{3-7}$ cycloalkyl,
(20) cycloheteroalkyl;
(21) $C_{1-6}$ alkyl,
(22) $C_{2-6}$ alkenyl,
(23) $C_{2-6}$ alkynyl, and
(24) aryl-$C_{1-6}$ alkyl;

wherein alkyl, alkenyl, alkynyl are straight chain or branched; alkyl, alkenyl, alkynyl, cycloalkyl, cycloheteroalkyl and aryl are optionally substituted with one to four substituents selected from a group independently selected from $R^d$;

each $R^d$ is independently selected from:
(1) halogen,
(2) —$NR^{11}R^{12}$,
(3) $C_{1-4}$alkyl,
(4) $C_{1-4}$alkoxy,
(5) aryl,
(6) aryl $C_{1-4}$alkyl,
(7) hydroxy,
(8) $CF_3$,
(9) —$OCF_3$,
(10) —C(O)$R^{10}$,
(11) —$CO_2 R^{10}$,
(12) —C(O)$NR^{11}R^{12}$,
(13) —OC(O)$C_{1-4}$alkyl,
(14) —$NR^9$C(O)$R^{10}$,
(15) —OC(O)$NR^{11}R^{12}$,
(16) —$NR^9$C(O)O$R^{10}$,
(17) —$NR^9$C(O)$NR^{11}R^{12}$,
(18) —OC(O)$NR^{11}R^{12}$, and
(19) aryloxy,
wherein alkyl is straight chain or branched;

$R^e$ and $R^f$ are each independently selected from:
(1) hydrogen,
(2) $C_{1-8}$ alkyl, straight chain or branched, unsubstituted or substituted with one to three substituents selected from halogen, hydroxyl, and $C_{1-6}$alkyloxy-,
(3) $C_{2-8}$ alkenyl, straight chain or branched,
(4) perfluoro $C_{1-6}$ alkyl, straight chain or branched,
(5) $C_{1-8}$ alkylcarbonyl-, straight chain or branched, unsubstituted or substituted on a carbon atom with one to three substituents selected from halogen, hydroxyl, and $C_{1-6}$alkyloxy-,
(6) $C_{1-8}$ alkylcarbonyloxy-, straight chain or branched, unsubstituted or substituted on a carbon atom with one to three substituents selected from halogen, hydroxyl, and $C_{1-6}$alkyloxy-,
(7) $C_{3-7}$cycloalkyl,
(8) cycloalkyl-$C_{1-6}$alkyl, wherein alkyl is straight chain or branched,
(9) cycloheteroalkyl,
(10) aryl, unsubstituted or substituted with one to three substituents selected from halogen, amino, carboxy, methyl, methoxy, hydroxy, trifluoromethyl, and methylcarbonyloxy,
(11) arylcarbonyl-, unsubstituted or substituted on a carbon atom with one to three substituents selected from halogen, amino, carboxy, methyl, methoxy, hydroxy, trifluoromethyl, and methylcarbonyloxy,
(12) arylcarbonyloxy-, unsubstituted or substituted on a carbon atom with one to three substituents selected from halogen, amino, carboxy, methyl, methoxy, hydroxy, trifluoromethyl, and methylcarbonyloxy,
(13) heteroaryl, unsubstituted or substituted on a carbon or nitrogen atom with one to three substituents selected from halogen, amino, carboxy, methyl, methoxy, hydroxy, trifluoromethyl, and methylcarbonyloxy,
(14) aryl $C_{1-6}$alkyl, wherein alkyl is straight chain or branched, and
(15) heteroaryl $C_{1-6}$alkyl, wherein alkyl is straight chain or branched, or $R^e$ and $R^f$ together with the atom(s) to which they are attached form a heterocyclic ring of 4 to 7 members containing 0-2 additional heteroatoms independently selected from oxygen, sulfur and N—$R^9$; n is selected from 0, 1, and 2;

or a pharmaceutically acceptable salt thereof.

In one embodiment of the present invention, Ar is selected from:
(1) phenyl, and
(2) pyridyl;

wherein phenyl and pyridyl are unsubstituted or substituted with one or two $R^c$ substituents.

In one class of this embodiment, Ar is selected from:
(1) phenyl, and
(2) pyridyl;

wherein phenyl and pyridyl are unsubstituted or substituted with one or two substituents independently selected from: halogen, methyl, trifluoromethyl, cyano, —$S(O)_nR^{10}$, and —$NHSO_2CH_3$.

In a subclass of this class, Ar is selected from:
(1) phenyl,
(2) 4-chlorophenyl,
(3) 4-fluorophenyl,
(4) 4-chloro-3-iodophenyl,
(5) 4-cyanophenyl,
(6) 4-trifluoromethylphenyl,
(7) 4-bromophenyl,
(8) 4-methylphenyl,
(9) 3-cyanophenyl,
(10) 3-methylsulfonylphenyl,
(11) 3-methylsulfonylaminophenyl,
(12) 3-bromophenyl,
(13) pyrid-3-yl,
(14) 6-chloro-pyrid-3-yl,
(15) 6-fluoropyrid-3-yl,
(16) 6-cyanopyrid-3-yl,
(17) pyrid-2-yl,
(18) 5-chloro-pyrid-2-yl,
(19) 5-fluoro-pyrid-2-yl,
(20) 5-cyano-pyrid-2-yl,
(21) pyrid-4-yl, and
(22) 2-chloro-pyrid-4-yl.

In another subclass Ar is selected from:
(1) phenyl,
(2) 4-chlorophenyl,
(3) 4-fluorophenyl,
(4) 4-chloro-3-iodophenyl,
(5) 4-cyanophenyl,
(6) 4-trifluoromethylphenyl,
(7) 4-bromophenyl,
(8) 4-methylphenyl,
(9) 3-cyanophenyl,
(10) 3-methylsulfonylphenyl, and
(11) 5-chloropyrid-2-yl, In yet another subclass Ar is selected from: phenyl, 4-chlorophenyl, 3-cyanophenyl, 4-cyanophenyl, 4-trifluoromethylphenyl, 4-chloro-3-iodophenyl, 4-bromophenyl, 3-methylsulfonylphenyl, 4-fluorophenyl, and 4-methylphenyl.

In another class of this embodiment, Ar is selected from phenyl, and pyridyl; wherein phenyl and pyridyl are unsubstituted or substituted with one or two substituents independently selected from: halogen, methyl, trifluoromethyl, cyano, —$S(O)_nR^{10}$.

In a subclass of this class, Ar is selected from:
(1) phenyl,
(2) 4-chlorophenyl,
(3) 4-fluorophenyl,
(4) 4-cyanophenyl,
(5) pyrid-3-yl,
(6) 6-chloro-pyrid-3-yl,
(7) 6-fluoro-pyrid-3-yl,
(8) 6-cyano-pyrid-3-yl,
(9) pyrid-2-yl,
(10) 5-chloro-pyrid-2-yl,
(11) 5-fluoro-pyrid-2-yl,
(12) 5-cyano-pyrid-2-yl, and
(13) pyrid-4-yl.

In another subclass, Ar is selected from:
(1) phenyl,
(2) 4-chlorophenyl, and
(3) 4-fluorophenyl.

In still another subclass, Ar is 4-chlorophenyl.

In one embodiment of the present invention, $R^4$ is selected from:
(1) $C_{1-6}$alkyl, straight chain or branched,
(2) $C_{2-6}$alkenyl, straight chain or branched,
(3) $C_{2-6}$alkynyl, straight chain or branched,
(4) $C_{3-7}$cycloalkyl,
(5) phenyl, and
(6) heteroaryl;

wherein alkyl, alkenyl, and alkynyl are unsubstituted or substituted with one to three $R^b$ substituents, and cycloalkyl, phenyl and heteroaryl are unsubstituted or substituted with one or two $R^c$ substituents.

In one class of this embodiment, $R^4$ is selected from:
(1) $C_{1-6}$alkyl, straight chain or branched,
(2) $C_{2-6}$alkenyl, straight chain or branched,
(3) $C_{2-6}$alkynyl, straight chain or branched,
(4) $C_{3-7}$cycloalkyl,
(5) phenyl, and
(6) heteroaryl;

wherein alkyl, alkenyl, and alkynyl are unsubstituted or substituted with one to three $R^b$ substituents, and cycloalkyl, phenyl, and heteroaryl are unsubstituted or substituted with one or two substituents independently selected from: halogen, $C_{1-3}$ alkyl, trifluoromethyl, cyano, —$S(O)_nR^{10}$, methyl, and —$NHSO_2CH_3$.

In one class of this embodiment, $R^4$ is selected from:
(1) $C_{1-6}$alkyl, straight chain or branched,
(2) $C_{2-6}$alkenyl, straight chain or branched,
(3) $C_{2-6}$alkynyl, straight chain or branched,
(4) $C_{3-7}$cycloalkyl,
(5) phenyl, and
(6) heteroaryl;

wherein alkyl, alkenyl, and alkynyl are unsubstituted or substituted with one to three $R^b$ substituents, and cycloalkyl, phenyl, and heteroaryl are unsubstituted or substituted with one or two substituents independently selected from: halogen, $C_{1-3}$ alkyl, trifluoromethyl, cyano, —$S(O)_nR^{10}$.

In one subclass of this class, $R^4$ is selected from:
(1) $C_{1-6}$alkyl, straight chain or branched,
(2) $C_{2-6}$alkenyl, straight chain or branched,
(3) $C_{2-6}$alkynyl, straight chain or branched,
(4) $C_{3-7}$cycloalkyl,
(5) phenyl, and
(6) pyridyl;

wherein alkyl, alkenyl, and alkynyl are unsubstituted or substituted with one to three halogen substituents, and cycloalkyl, phenyl, and pyridyl are unsubstituted or substituted with one or two substituents independently selected from: halogen, cyano, —$S(O)_nR^{10}$.

In another subclass of this class, R⁴ is selected from:
(1) $C_{1-6}$alkyl, straight chain or branched,
(2) $C_{2-6}$alkenyl, straight chain or branched,
(3) phenyl,
(4) pyridyl, and
(5) thienyl, wherein alkyl, and alkenyl are unsubstituted or substituted with one to three halogen substituents, and phenyl, pyridyl and thienyl are unsubstituted or substituted with one or two substituents independently selected from: halogen, methyl, cyano, —$S(O)_2CH_3$, trifluoromethyl, and —$NHSO_2CH_3$.

In another subclass of this class, R⁴ is selected from:
(1) methyl,
(2) n-butyl,
(3) 3-butenyl,
(4) phenyl,
(5) 4-chlorophenyl,
(6) 4-fluorophenyl,
(7) 3-cyanophenyl,
(8) 2-chlorophenyl,
(9) 3-bromophenyl,
(10) 4-trifluoromethylphenyl,
(11) 4-methylsulfonylphenyl,
(12) thienyl,
(13) 4-bromo-2-thienyl,
(14) 4-cyano-2-thienyl,
(15) pyridyl,
(16) 2-chloro-5-pyridyl,
(17) 2-chloro-4-pyridyl, and
(18) 3-chloro-6-pyridyl.

In another subclass of this class, R⁴ is selected from:
(1) $C_{1-6}$alkyl, straight chain or branched,
(2) $C_{2-6}$alkenyl, straight chain or branched,
(3) phenyl, and
(4) pyridyl;

wherein alkyl, and alkenyl are unsubstituted or substituted with one to three halogen substituents, and phenyl and pyridyl are unsubstituted or substituted with one or two substituents independently selected from: halogen, cyano, —$S(O)_2CH_3$.

In yet another subclass of this class, R⁴ is selected from:
(1) methyl,
(2) ethyl,
(3) n-propyl,
(4) n-butyl,
(5) isobutyl,
(6) t-butyl,
(7) 3-methylbutyl,
(8) 3,3-dimethylbutyl,
(9) n-pentyl,
(10) n-hexyl,
(11) straight chain $C_{2-6}$alkenyl,
(12) phenyl,
(13) 4-chlorophenyl,
(14) 4-fluorophenyl,
(15) 4-cyanophenyl,
(16) 3-cyanophenyl,
(17) 4-methylsulfonylphenyl,
(18) pyrid-3-yl,
(19) 6-chloro-pyrid-3-yl,
(20) 6-fluoro-pyrid-3-yl,
(21) 6-cyano-pyrid-3-yl,
(22) 4-chloro-pyrid-3-yl,
(23) 4-fluoro-pyrid-3-yl,
(24) 4-cyano-pyrid-3-yl,
(25) pyrid-2-yl,
(26) 5-chloro-pyrid-2-yl,
(27) 5-fluoro-pyrid-2-yl,
(28) 5-cyano-pyrid-2-yl, and
(29) pyrid-4-yl.

In still another subclass of this class, R⁴ is selected from:
(1) methyl,
(2) n-butyl,
(3) 3-butenyl,
(4) phenyl,
(5) 4-chlorophenyl,
(6) 4-fluorophenyl,
(7) 4-cyanophenyl,
(8) 3-cyanophenyl, and
(9) 4-methylsulfonylphenyl.

In still another subclass of this class, R⁴ is selected from:
(1) methyl,
(2) n-butyl,
(3) 3-butenyl,
(4) phenyl,
(5) 4-chlorophenyl,
(6) 4-fluorophenyl, and
(7) 3-cyanophenyl.

In one embodiment of the present invention, R⁵, R⁶, R⁷, and R⁸ are each independently selected from: hydrogen, $C_{1-6}$ alkyl, unsubstituted or substituted with $R^b$, and $C_{2-6}$ alkenyl, unsubstituted or substituted with $R^b$.

In one class of this embodiment, R⁵, R⁶, R⁷, and R⁸ are each independently selected from: hydrogen, methyl and $C_2$ alkenyl.

In one subclass of this class, one of R⁵, R⁶, R⁷, and R⁸ is methyl and the other three are each hydrogen.

In another subclass of this class, R⁵, R⁶, R⁷, and R⁸ are each hydrogen.

In one embodiment of the present invention, Z is selected from hydrogen, hydroxy, fluoro, methyl, and —$N(R^{11})(R^{12})$, and $Z^1$ is selected from:

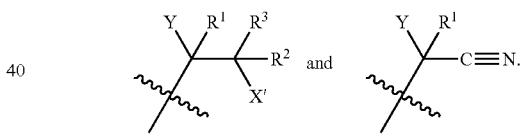

In one class of this embodiment, Z is selected from hydrogen, hydroxy, fluoro, methyl, and —$NH_2$, and $Z^1$ is selected from:

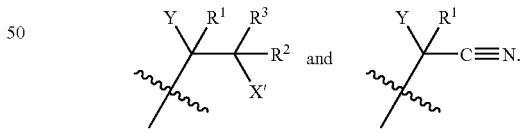

In one subclass of this class, Z is selected from hydrogen and hydroxy, and $Z^1$ is:

In another subclass of this class, Z is selected from hydrogen and hydroxy, and $Z^1$ is:

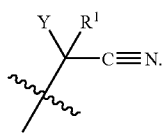

In still another subclass of this class, Z is hydrogen, and $Z^1$ is:

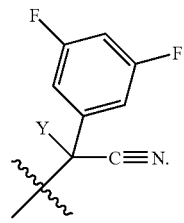

In one embodiment of the present invention, Y is selected from:
(1) hydrogen,
(2) hydroxy,
(3) $C_{1-3}$ alkyloxy,
(4) fluoro,
(5) $C_{1-3}$ alkyl,
(6) trifluoromethyl, and
(7) —$N(R^{11})(R^{12})$.

In one class of this embodiment, Y is selected from:
(1) hydrogen,
(2) hydroxy,
(3) methoxy,
(4) fluoro,
(5) methyl,
(6) trifluoromethyl, and
(7) —$NH_2$.

In one subclass of this class, Y is selected from:
(1) hydrogen,
(2) hydroxy, and
(3) methyl.

In another subclass of this class, Y is selected from:
(1) hydrogen,
(2) hydroxy, and
(3) fluoro.

In another subclass of this class, Y is hydrogen.

In one embodiment of the present invention, X' is selected from:
(1) hydroxy,
(2) $C_{1-6}$alkyl, straight chain or branched, unsubstituted or substituted with one or two $R^b$ substituents,
(3) perfluoro $C_{1-6}$alkyl,
(4) $C_{2-6}$alkenyl, straight chain or branched, unsubstituted or substituted with one to two $R^b$ substituents,
(5) $C_{2-6}$alkynyl, straight chain or branched, unsubstituted or substituted with one to two $R^b$ substituents,
(6) cyano,
(7) —$C(O)R^{10}$,
(8) —$C(O)OR^{10}$,
(9) —$C(O)N(R^{11})(R^{12})$,
(10) —$N(R^9)S(O)_nR^{10}$,
(11) —$NR^9C(O)R^{10}$,
(12) —$NR^9C(O)OR^{10}$,
(13) —$N(R^{11})(R^{12})$,
(14) —$S(O)_nR^{10}$,
(15) —$OR^{10}$,
(16) —$OC(O)R^{10}$, and
(17) —$OC(O)N(R^{11})(R^{12})$.

In one class of this embodiment, X' is selected from:
(1) hydroxy,
(2) $C_{1-6}$alkyl, straight chain or branched, unsubstituted or substituted with one or two $R^b$ substituents,
(3) trifluoromethyl,
(4) $C_{2-6}$alkenyl, straight chain or branched, unsubstituted or substituted with one to two $R^b$ substituents,
(5) cyano,
(6) —$C(O)R^{10}$,
(7) —$C(O)OR^{10}$,
(8) —$C(O)N(R^{11})(R^{12})$,
(9) —$N(R^9)S(O)_nR^{10}$.
(10) —$NR^9C(O)R^{10}$,
(11) —$NR^9C(O)OR^{10}$,
(12) —$N(R^{11})(R^{12})$,
(13) —$S(O)_2R^{10}$,
(14) —$OR^{10}$,
(15) —$OC(O)R^{10}$, and
(16) —$OC(O)N(R^{11})(R^{12})$.

In one subclass of this class, X' is selected from:
(1) hydroxy,
(2) $C_{1-4}$alkyl, straight chain or branched, unsubstituted or substituted with a substituent selected from halogen, hydroxy, and methoxy,
(3) trifluoromethyl,
(4) $C_{2-4}$alkenyl, straight chain or branched,
(5) cyano,
(6) —$C(O)CH_3$,
(7) —$C(O)OH$,
(8) —$C(O)OCH_3$,
(9) —$C(O)N(R^{11})(R^{12})$,
(10) —$NHS(O)_2R^{10}$,
(11) —$NHC(O)R^{10}$,
(12) —$NHC(O)OR^{10}$,
(13) —$N(R^{11})(R^{12})$,
(14) —$S(O)_2R^{10}$,
(15) $OR^{10}$,
(16) —$OC(O)R^{10}$, and
(17) —$OC(O)N(R^{11})(R^{12})$.

In another subclass of this class, X' is selected from:
(1) hydroxy,
(2) methyl,
(3) ethyl,
(4) isopropyl,
(5) t-butyl,
(6) sec-butyl,
(7) n-butyl,
(8) hydroxymethyl,
(9) trifluoromethyl,
(10) allyl,
(11) cyano,
(12) —$C(O)CH_3$,
(13) —$C(O)OH$,
(14) —$C(O)OCH_3$,
(15) —$C(O)N(CH_3)_2$,
(16) —$C(O)NH$—$CH(CH_3)_2$,
(17) —$NHS(O)_2C(CH_3)_3$,
(18) —$N(CH_3)_2$,
(19) —$NH$—$CH(CH_3)_2$
(20) —$OC(O)CH_3$,
(21) —$OC(O) N(CH_3)_2$, and
(22) —$OC(O)NH$—$CH(CH_3)_2$.

In another subclass of this class, X' is selected from:
(1) $C_{1-4}$alkyl, straight chain or branched, unsubstituted or substituted with a substituent selected from halogen, hydroxy, and methoxy,
(2) trifluoromethyl,
(3) $C_{2-4}$alkenyl, straight chain or branched,
(4) cyano,
(5) —C(O)CH$_3$,
(6) —C(O)OH,
(7) —C(O)OCH$_3$,
(8) —C(O)N(R$^{11}$)(R$^{12}$),
(9) —NHS(O)$_2$R$^{10}$,
(10) —S(O)$_2$R$^{10}$,
(11) —OC(O)R$^{10}$, and
(12) —OC(O)N(R$^{11}$)(R$_{12}$),
(13) —OCH$_3$, and,
(14) —NH$_2$.

In yet another subclass of this class, X' is selected from:
(1) hydroxy,
(2) NH$_2$,
(3) methyl, and
(4) methoxy.

In still another subclass of this class, X' is selected from:
(1) $C_{1-4}$alkyl, straight chain or branched, unsubstituted or substituted with a substituent selected from halogen, hydroxy, and methoxy,
(2) trifluoromethyl,
(3) $C_{2-4}$alkenyl, straight chain or branched,
(4) cyano,
(5) —C(O)CH$_3$,
(6) —C(O)OH,
(7) —C(O)OCH$_3$,
(8) —C(O)N(R$^{11}$)(R$^{12}$),
(9) —NHS(O)$_2$R$^{10}$,
(10) —S(O)$_2$R$^{10}$,
(11) —OC(O)R$^{10}$, and
(12) —OC(O)N(R$^{11}$)(R$^{12}$).

In another embodiment of the present invention, Z and Z$^1$ together form:

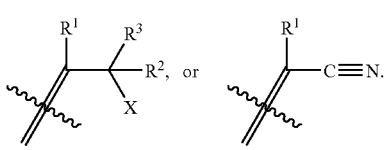

In one class of this embodiment, Z and Z$^1$ together form:

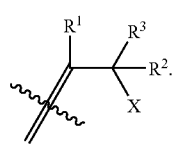

In another class of this embodiment, Z and Z$^1$ together form:

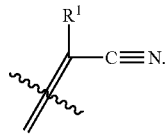

In one subclass of this class, Z and Z$^1$ together form:

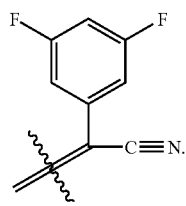

In another subclass of this class, Z and Z$^1$ together form:

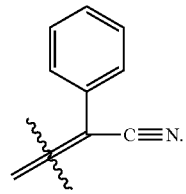

In one embodiment of the present invention, X is selected from:
(1) hydroxy,
(2) $C_{1-6}$alkyl, straight chain or branched, unsubstituted or substituted with one or two R$^b$ substituents,
(3) perfluoro $C_{1-6}$alkyl,
(4) $C_{2-6}$alkenyl, straight chain or branched, unsubstituted or substituted with one to two R$^b$ substituents,
(5) $C_{2-6}$alkynyl, straight chain or branched, unsubstituted or substituted with one to two R$^b$ substituents,
(6) cyano,
(7) —C(O)R$^{10}$,
(8) —C(O)OR$^{10}$,
(9) —C(O)N(R$^{11}$)(R$^{12}$),
(10) —N(R$^9$)S(O)$_n$R$^{10}$,
(11) —NR$^9$C(O)R$^{10}$,
(12) —NR$^9$C(O)OR$^{10}$,
(13) —N(R$^{11}$)(R$^{12}$),
(14) —S(O)$_n$R$^{10}$,
(15) —OR$^{10}$,
(16) —OC(O)R$^{10}$, and
(17) —OC(O)N(R$^{11}$)(R$^{12}$);

In one class of this embodiment, X is selected from:
(1) hydroxy,
(2) $C_{1-6}$alkyl, straight chain or branched, unsubstituted or substituted with one or two R$^b$ substituents,
(3) trifluoromethyl,
(4) $C_{2-6}$alkenyl, straight chain or branched, unsubstituted or substituted with one to two R$^b$ substituents,
(5) cyano,
(6) —C(O)R$^{10}$,
(7) —C(O)OR$^{10}$,
(8) —C(O)N(R$^{11}$)(R$^{12}$),
(9) —N(R$^9$)S(O)$_n$R$^{10}$,
(10) —NR$^9$C(O)R$^{10}$,

(11) —NR⁹C(O)OR¹⁰,
(12) —N(R¹¹)(R¹²),
(13) —S(O)₂R¹⁰,
(14) —OR¹⁰,
(15) —OC(O)R¹⁰, and
(16) —OC(O)N(R¹¹)(R¹²).

In one subclass of this class, X is selected from:
(1) hydroxy,
(2) $C_{1-4}$alkyl, straight chain or branched, unsubstituted or substituted with a substituent selected from halogen, hydroxy, and methoxy,
(3) trifluoromethyl,
(4) $C_{2-4}$alkenyl, straight chain or branched,
(5) cyano,
(6) —C(O)CH₃,
(7) —C(O)OH,
(8) —C(O)OCH₃,
(9) —C(O)N(R¹¹)(R¹²),
(10) —NHS(O)₂R¹⁰,
(11) —NHC(O)R¹⁰,
(12) —NHC(O)OR¹⁰,
(13) —N(R¹¹)(R¹²),
(14) —S(O)₂R¹⁰,
(15) —OR¹⁰,
(16) —OC(O)R¹⁰, and
(17) —OC(O)N(R¹¹)(R¹²).

In another subclass of this class, X is selected from:
(1) hydroxy,
(2) methyl,
(3) ethyl,
(4) isopropyl,
(5) t-butyl,
(6) sec-butyl,
(7) n-butyl,
(8) hydroxymethyl-
(9) trifluoromethyl,
(10) allyl,
(11) cyano,
(12) —C(O)CH₃,
(13) —C(O)OH,
(14) —C(O)OCH₃,
(15) —C(O)N(CH₃)₂,
(16) —C(O)NH—H(CH₃)₂,
(17) —NHS(O)₂C(CH₃)₃,
(18) —N(CH₃)₂,
(19) —NH—CH(CH₃)₂
(20) —OC(O)CH₃,
(21) —OC(O) N(CH₃)₂, and
(22) —OC(O)NH—CH(CH₃)₂.

In another subclass of this class, X is selected from:
(1) hydroxy,
(2) methyl,
(3) ethyl,
(4) isopropyl,
(5) t-butyl,
(6) sec-butyl,
(7) n-butyl,
(8) hydroxymethyl-
(9) trifluoromethyl,
(10) allyl,
(11) cyano,
(12) —C(O)CH₃,
(13) —C(O)OH,
(14) —C(O)OCH₃,
(15) —C(O)N(CH₃)₂,
(16) —C(O)NH—CH(CH₃)₂,
(17) —NHS(O)₂C(CH₃)₃,
(18) —N(CH₃)₂,
(19) —NH—CH(CH₃)₂,
(20) —OC(O)CH₃,
(21) —OC(O) N(CH₃)₂,
(22) —OC(O)NH—CH(CH₃)₂,
(23) methoxy, and
(24) NH₂.

In still another subclass of this class, X is selected from:
(1) hydroxy,
(2) methyl,
(3) ethyl,
(4) methoxy,
(5) cyano,
(6) NH₂,
(7) N(CH₃)₂,
(8) —NH—(CH₃)₂,
(9) —OC(O)CH₃,
(10) —OC(O)N(CH₃)₂, and
(11) —OC(O)NH—CH(CH₃)₂.

In yet another subclass of this class, X is selected from:
(1) hydroxy,
(2) NH₂,
(3) methyl, and
(4) methoxy.

In one embodiment of the present invention, R¹ is selected from:
(1) aryl,
(2) heteroaryl,
(3) $C_{3-7}$ cycloalkyl, and
(4) cycloheteroalkyl, wherein aryl, heteroaryl, cycloalkyl and cycloheteroalkyl are unsubstituted or substituted with one to three $R^c$ substituents.

In one class of this embodiment, R¹ is selected from:
(1) phenyl,
(2) imidazolyl,
(3) thienyl,
(4) pyridyl,
(5) cyclopropyl,
(6) cyclopentyl, and
(7) cyclohexyl.

wherein the R¹ moiety is unsubstituted or substituted with one or two $R^c$ substituents.

In one subclass of this class, R¹ is selected from
(1) phenyl,
(2) imidazolyl,
(3) thienyl,
(4) pyridyl,
(5) cyclopropyl,
(6) cyclopentyl, and
(7) cyclohexyl, wherein the R¹ moiety is unsubstituted or substituted with one or two substituents independently selected from halogen, methyl, cyano, SO₂CH₃, and trifluoromethyl.

In one subclass of this class, R¹ is selected from:
(1) phenyl,
(2) imidazolyl,
(3) thienyl, and
(4) pyridyl, wherein the R¹ moiety is unsubstituted or substituted with one or two substituents independently selected from halogen, methyl, cyano, SO₂CH₃, and trifluoromethyl.

In yet another subclass of this class, R¹ is selected from:
(1) phenyl,
(2) 3,5-difluorophenyl,
(3) 3-chlorophenyl, (4) 3-fluorophenyl,
(5) 4-fluorophenyl,
(6) 3-trifluoromethylphenyl,
(7) 3-cyanophenyl,
(8) 1-methyl-1H-imidazol-4-yl,
(9) thien-3-yl,
(10) thien-2-yl,
(11) pyrid-3-yl, and
(12) 5-cyano-pyrid-3-yl.

In still another subclass of this class, $R^1$ is 3,5-difluorophenyl.

In one subclass of this class, $R^1$ is:
(1) phenyl,
(2) imidazolyl,
(3) thienyl,
(4) pyridyl,
(5) triazolyl, and
(6) azetidinyl, wherein the $R^1$ moiety is unsubstituted or substituted with one or two substituents independently selected from: halogen, methyl, cyano, $SO_2CH_3$, $SCH_3$, $SCH_2CH_3$, $SCH(CH_3)_2$, $NH_2$, trifluoromethyl, thienyl, triazolyl, imidazolyl, and azetidinyl.

In another subclass of this class, $R^1$ is selected from:
(1) phenyl,
(2) 3,5-difluorophenyl,
(3) 3-chlorophenyl,
(4) 3-fluorophenyl,
(5) 4-fluorophenyl,
(6) 3-trifluoromethylphenyl,
(7) 3-cyanophenyl,
(8) 1-methyl-1H-imidazol-4-yl,
(9) thien-3-yl,
(10) thien-2-yl,
(11) pyrid-3-yl,
(12) 5-cyano-pyrid-3-yl,
(13) 4H-1,2,4-triazol-4-yl,
(14) 1H-1,2,4-triazol-4-yl,
(15) 3-fluoro-5-(methylthio)phenyl,
(16) 3-fluoro-5-(ethylthio)phenyl,
(17) 3-fluoro-5-(isopropylthio)phenyl,
(18) 3-fluoro-5-(1H-imidazol-1-yl)phenyl,
(19) 3-fluoro-5-(1H-1,2,4-triazol-1-yl)phenyl,
(20) 3-fluoro-5-(azetidin-1-yl)phenyl,
(21) 3-cyano-5-fluorophenyl,
(22) 3-amino-5-fluorophenyl, and
(23) 3-fluoro-5(4H-1,2,4-triazol-4-yl)phenyl.

In one embodiment of the present invention, $R^2$ and $R^3$, together with the carbon atom to which they are attached, form a carbonyl group.

In another embodiment of the present invention, $R^2$ and $R^3$, together with the carbon atom to which they are attached, form a 3 to 7 membered carbocyclic ring system.

In one class of this embodiment, $R^2$ and $R^3$, together with the carbon atom to which they are attached, form a 3, 4, or 5-membered carbocyclic ring.

In one subclass of this class, $R^2$ and $R^3$, together with the carbon atom to which they are attached, form a 4-membered carbocyclic ring.

In another embodiment of the present invention, $R^2$ and $R^3$ are each independently selected from:
(1) hydrogen,
(2) $C_{1-6}$alkyl, straight chain or branched, unsubstituted or substituted with one or two $R^b$ substituents,
(3) fluoro,
(4) hydroxyl, and
(5) perfluoro $C_{1-6}$alkyl, straight chain or branched.

In a class of this embodiment, $R^2$ and $R^3$ are each independently selected from:
(1) hydrogen,
(2) methyl,
(3) fluoro,
(4) hydroxyl, and
(5) trifluoromethyl.

In a subclass of this class, $R^2$ is selected from:
(1) hydrogen,
(2) methyl, and
(3) hydroxyl, and
$R^3$ is selected from:
(1) methyl, and
(2) hydroxyl.

In another subclass, $R^2$ is selected from:
(1) hydrogen,
(2) fluoro,
(3) methyl, and
(4) hydroxyl, and
$R^3$ is selected from methyl, and hydroxyl.

In another subclass of the present invention, $R^2$ and $R^3$ are each fluoro.

In one embodiment of the present invention, $R^9$ is selected from: hydrogen, $C_{1-6}$alkyl, and $C_{2-6}$alkenyl, straight chain or branched, unsubstituted or substituted with one to three halogen atoms.

In one class of this embodiment, $R^9$ is selected from: hydrogen, and $C_{1-6}$alkyl, straight chain or branched, unsubstituted or substituted with one to three halogen atoms.

In a subclass of this class, $R^9$ is selected from: hydrogen, $C_{1-6}$alkyl, straight chain or branched, and trifluoromethyl.

In another subclass of this class, $R^9$ is selected from: hydrogen and methyl.

In one embodiment of the present invention, $R^{10}$ is selected from:
(1) $C_{1-4}$-alkyl, straight chain or branched, unsubstituted or substituted with one to three $R^a$ substituents,
(2) aryl, unsubstituted or substituted with one to three $R^a$ substituents,
(3) aryl $C_{1-4}$alkyl, wherein alkyl is straight or branched chain, unsubstituted or substituted on one, two or three carbon atoms with one to three $R^a$ substituents, and wherein the aryl group is substituted with one to three $R^b$ substituents, and
(4) —$CF_3$.

In one class of this embodiment, $R^{10}$ is selected from:
(1) $C_{1-4}$alkyl, straight chain or branched, unsubstituted or substituted with one to three $R^a$ substituents,
(2) phenyl, unsubstituted or substituted with one to three $R^a$ substituents,
(3) benzyl, wherein the phenyl group is substituted with one to three $R^a$ substituents, and
(4) —$CF_3$.

In one subclass of this class, $R^{10}$ is selected from:
(1) $C_{1-4}$alkyl, straight chain or branched,
(2) phenyl, unsubstituted or substituted with one or two $R^a$ substituents, and
(3) —$CF_3$.

In one embodiment of the present invention, $R^{11}$ and $R^{12}$ together with the atom(s) to which they are attached form a heterocyclic ring of 4 to 7 members containing 0-2 additional heteroatoms independently selected from oxygen, sulfur and N—$R^9$.

In one class of this embodiment, $R^{11}$ and $R^{12}$ together with the atom(s) to which they are attached form a heterocyclic ring of 5 to 6 members.

In another embodiment of the present invention, $R^{11}$ and $R^{12}$ are each independently selected from:
(1) hydrogen,
(2) $C_{1-8}$ alkyl, straight chain or branched, unsubstituted or substituted with one to three substituents selected from $R^a$,
(3) $C_{2-8}$ alkenyl, straight chain or branched,
(4) perfluoro $C_{1-6}$ alkyl, straight chain or branched,
(5) $C_{3-7}$cycloalkyl, unsubstituted or substituted with one to three substituents selected from $R^a$,
(6) cycloalkyl-$C_{1-6}$alkyl, wherein alkyl is straight chain or branched,
(7) cycloheteroalkyl,
(8) aryl, unsubstituted or substituted with one to three substituents selected from $R^a$,
(9) heteroaryl, unsubstituted or substituted on a carbon or nitrogen atom with one to three substituents selected from $R^a$,
(10) aryl $C_{1-6}$alkyl, wherein alkyl is straight chain or branched, and
(11) heteroaryl $C_{1-6}$alkyl, wherein alkyl is straight chain or branched.

In a class of this embodiment, $R^{11}$ and $R^{12}$ are each independently selected from:
(1) hydrogen,
(2) $C_{1-6}$ alkyl, straight chain or branched, unsubstituted or substituted with one or two substituents selected from $R^a$,
(3) $C_{2-6}$ alkenyl, straight chain or branched,
(4) trifluoromethyl,
(5) $C_{3-7}$cycloalkyl, unsubstituted or substituted with one to three substituents selected from $R^a$,
(6) cycloalkyl-methyl,
(7) cycloheteroalkyl,
(8) phenyl, unsubstituted or substituted with one to three substituents selected from $R^a$,
(9) pyridyl, unsubstituted or substituted on a carbon or nitrogen atom with one to three substituents selected from $R^a$,
(10) benzyl, and
(11) pyridylmethyl.

In a subclass of this class, $R^{11}$ and $R^{12}$ are each independently selected from:
(1) hydrogen,
(2) $C_{1-4}$ alkyl, straight chain or branched, unsubstituted or substituted with one or two substituents selected from $R^a$,
(3) trifluoromethyl,
(4) phenyl,
(5) pyridyl, and
(6) benzyl.

In a subclass of this class, $R^{11}$ and $R^{12}$ are each independently selected from:
(1) hydrogen,
(2) methyl, and
(3) isopropyl.

In one embodiment of the present invention, each $R^a$ is independently selected from:
(1) halogen,
(2) $N(R^e)(R^f)$,
(3) carboxy,
(4) $C_{1-4}$alkyl,
(5) $C_{1-4}$alkoxy,
(6) aryl,
(7) aryl $C_{1-4}$alkyl,
(8) hydroxy,
(9) $CF_3$,
(10) —$OC(O)C_{1-4}$alkyl, and
(11) aryloxy, wherein alkyl may be straight chain or branched.

In one class of this embodiment, each $R^a$ is independently selected from
(1) chloro,
(2) fluoro,
(3) $NH_2$,
(4) carboxy,
(5) methyl,
(6) ethyl,
(7) isopropyl,
(8) n-propyl,
(9) n-butyl,
(10) t-butyl,
(11) sec-butyl,
(12) methoxy,
(13) phenyl,
(14) benzyl,
(15) hydroxy,
(16) $CF_3$,
(17) —$OC(O)CH_3$, and
(18) phenoxy.

In one subclass of this class, each $R^a$ is independently selected from:
(1) fluoro,
(2) chloro,
(3) methyl,
(4) methoxy,
(5) hydroxy, and
(6) $CF_3$.

In another embodiment of the present invention, each $R^b$ is independently selected from:
(1) halogen,
(2) —$OR^{10}$,
(3) —$CF_3$,
(4) aryl,
(5) heteroaryl,
(6) cyano,
(7) —$C(O)R^{10}$,
(8) —$C(O)OR^{10}$,
(9) —$C(O)N(R^e)(R^f)$,
(10) —$N(R^9)S(O)_nR^{10}$,
(11) —$NR^9C(O)R^{10}$,
(12) —$NR^9C(O)OR^{10}$,
(13) —$N(R^e)(R^f)$,
(14) —$S(O)_nR^{10}$,
(15) —$S(O)_2OR^{10}$,
(16) —$OC(O)R^{10}$,
(17) —$OC(O)N(R^e)(R^f)$,
(18) —$NO_2$,
(19) $C_{3-7}$ cycloalkyl, and
(20) cycloheteroalkyl;

wherein cycloalkyl, cycloheteroalkyl, heteroaryl and aryl are optionally substituted with one to four substituents selected from a group independently selected from $R^d$.

In one class of this embodiment, each $R^b$ is independently selected from:
(1) halogen,
(2) hydroxy,
(3) methyoxy,
(4) —$CF_3$,
(5) phenyl,
(6) cyano,
(7) —$C(O)CH_3$,
(8) —$C(O)OH$, (9) —C(O)OCH$_3$,
(10) —C(O)NH$_2$,
(11) —C(O)NH(CH$_3$),
(12) —C(O)N(CH$_3$)$_2$,
(13) —NH$_2$,
(14) —S(O)$_2$CH$_3$,
(15) —S(O)$_2$H,
(16) —OC(O)R$^{10}$,
(17) —OC(O)N(CH$_3$)$_2$,
(18) —OC(O)NH—CH(CH$_3$)$_2$,
(19) —NO$_2$,
(20) cyclopropyl, and
(21) cyclohexyl, wherein cycloalkyl and phenyl are optionally substituted with one or two substituents selected from a group independently selected from R$^d$.

In one subclass of this class, each R$^b$ is independently selected from:
(1) fluoro,
(2) chloro,
(3) hydroxy,
(4) methyoxy,
(5) —CF$_3$,
(6) phenyl,
(7) cyano,
(8) —C(O)CH$_3$,
(9) —C(O)OH,
(10) —C(O)OCH$_3$,
(11) —C(O)NH$_2$,
(12) —C(O)NH(CH$_3$),
(13) —C(O)N(CH$_3$)$_2$,
(14) —NH$_2$,
(15) —S(O)$_2$CH$_3$,
(16) —OC(O)N(CH$_3$)$_2$, and
(17) —OC(O)NH—CH(CH$_3$)$_2$, wherein cycloalkyl and phenyl are optionally substituted with one or two substituents selected from a group independently selected from R$^d$.

In another subclass of this class, each R$^b$ is independently selected from:
(1) fluoro,
(2) chloro,
(3) hydroxy,
(4) methyoxy,
(5) —CF$_3$,
(6) cyano,
(7) —C(O)CH$_3$,
(8) —C(O)OH,
(9) —C(O)OCH$_3$,
(10) —C(O)NH$_2$,
(11) —C(O)NH(CH$_3$), and
(12) —C(O)N(CH$_3$)$_2$, wherein cycloalkyl and phenyl are optionally substituted with one or two substituents selected from a group independently selected from R$^d$.

In one embodiment of the present invention, each R$^c$ is independently selected from:
(1) halogen,
(2) —OR$^{10}$,
(3) —CF$_3$,
(4) aryl,
(5) heteroaryl,
(6) cyano,
(7) —C(O)R$^{10}$,
(8) —C(O)OR$^{10}$,
(9) —C(O)N(R$^{11}$)(R$^{12}$),
(10) —N(R$^9$)S(O)$_n$R$^{10}$,
(11) —NR$^9$C(O)R$^{10}$,
(12) —NR$^9$C(O)OR$^{10}$,
(13) —N(R$^{11}$)(R$^{12}$),
(14) —S(O)$_n$R$^{10}$,
(15) —S(O)$_2$OR$^{10}$,
(16) —OC(O)R$^{10}$,
(17) —OC(O)N(R$^{11}$)(R$^{12}$),
(18) —NO$_2$,
(19) C$_{3-7}$ cycloalkyl,
(20) cycloheteroalkyl;
(21) C$_{1-6}$ alkyl,
(22) C$_{2-6}$ alkenyl,
(23) C$_{2-6}$ alkynyl, and
(24) aryl-C$_{1-6}$ alkyl;

wherein alkyl, alkenyl, alkynyl are straight chain or branched; alkyl, alkenyl, alkynyl, cycloalkyl, cycloheteroalkyl and aryl are optionally substituted with one to four substituents selected from a group independently selected from R$^d$.

In one class of this embodiment, each R$^c$ is independently selected from:
(1) halogen,
(2) —OH,
(3) —OCH$_3$,
(4) —CF$_3$,
(5) phenyl,
(6) pyridyl,
(7) cyano,
(8) —C(O)CH$_3$,
(9) —C(O)OR$^{10}$,
(10) —C(O)NH$_2$,
(11) —N(H)S(O)$_2$R$^{10}$,
(12) —NHC(O)R$^{10}$,
(13) —NHC(O)OR$^{10}$,
(14) —N(CH$_3$)$_2$,
(15) NH$_2$,
(16) —S(O)$_2$R$^{10}$,
(17) —OC(O)CH$_3$,
(18) —OC(O)N(CH$_3$)$_2$,
(19) —OC(O)NH—CH(CH$_3$)$_2$,
(20) —NO$_2$,
(21) cyclopropyl,
(22) methyl,
(23) C$_{2-6}$ alkenyl, and
(24) benzyl;

wherein alkyl, alkenyl, alkynyl are straight chain or branched; alkyl, alkenyl, alkynyl, cycloalkyl, cycloheteroalkyl and aryl are optionally substituted with one or two substituents selected from a group independently selected from R$^d$.

In one subclass of this class, each R$^c$ is independently selected from:
(1) halogen,
(2) —OH,
(3) —OCH$_3$,
(4) —CF$_3$,
(5) cyano, and
(6) —S(O)$_2$R$^{10}$.

In another class of this embodiment, each R$^c$ is independently selected from:
(1) halogen,
(2) —OH,
(3) —OCH$_3$,
(4) —CF$_3$,
(5) phenyl,
(6) pyridyl, (7) triazolyl,
(8) azetidinyl,
(9) imidazolyl,
(10) thienyl,
(11) cyano,
(12) —C(O)CH$_3$,
(13) —C(O)OR$^{10}$,
(14) —C(O)NH$_2$,
(15) —NHS(O)$_2$R$^{10}$,
(16) —NHC(O)R$^{10}$,
(17) —NHC(O)OR$^{10}$,
(18) —N(CH$_3$)$_2$,
(19) NH$_2$,
(20) SR$^{10}$,
(21) —S(O)$_2$R$^{10}$,
(22) —OC(O)CH$_3$,
(23) —OC(O)N(CH$_3$)$_2$,
(24) —OC(O)NH—CH(CH$_3$)$_2$,
(25) —NO$_2$,
(26) cyclopropyl,
(27) methyl,
(28) C$_{2-6}$ alkenyl, and
(29) benzyl;

wherein alkyl, alkenyl, are straight chain or branched; alkyl, alkenyl, cycloalkyl, cycloheteroalkyl aryl, and heteroaryl are optionally substituted with one or two substituents independently selected from R$^d$.

In a subclass of this class, each R$^c$ is independently selected from:
(1) halogen,
(2) —OH,
(3) —CH$_3$,
(4) —CF$_3$,
(5) cyano,
(6) —S(O)$_2$R$^{10}$,
(7) triazolyl
(8) azetidinyl,
(9) imidazolyl,
(10) SCH$_3$,
(11) SCH$_2$CH$_3$,
(12) SCH(CH$_3$)$_2$, and
(13) NH$_2$.

In one embodiment of the present invention, each R$^d$ is independently selected from:
(1) halogen,
(2) —NR$^{11}$R$^{12}$
(3) C$_{1-4}$alkyl,
(4) C$_{1-4}$alkoxy,
(5) aryl,
(6) aryl C$_{1-4}$alkyl,
(7) hydroxy,
(8) CF$_3$,
(9) —OCF$_3$,
(10) —C(O)R$^{10}$,
(11) —CO$_2$R$^{10}$,
(12) —C(O)NR$^{11}$R$^{12}$,
(13) —OC(O)C$_{1-4}$alkyl,
(14) —NR$^9$C(O)R$^{10}$,
(15) —OC(O)NR$^{11}$R$^{12}$,
(16) —NR$^9$C(O)OR$^{10}$,
(17) —NR$^9$C(O)NR$^{11}$R$^{12}$,
(18) —OC(O)NR$^{11}$R$^{12}$, and
(19) aryloxy, wherein alkyl is straight chain or branched.

In one class of this embodiment of the present invention, each R$^d$ is independently selected from:

(1) halogen,
(2) —NH$_2$,
(3) methyl,
(4) methoxy,
(5) phenyl,
(6) benzyl,
(7) hydroxy,
(8) CF$_3$,
(9) —OCF$_3$,
(10) —C(O)CH$_3$,
(11) —CO$_2$H,
(12) —CO$_2$CH$_3$,
(13) —C(O)NH$_2$,
(14) —OC(O)CH$_3$,
(15) —NHC(O)CH$_3$,
(16) —OC(O)N(CH$_3$)$_2$,
(17) —NHC(O)OCH$_3$,
(18) —NHC(O)N(CH$_3$)$_2$,
(19) —OC(O)N(CH$_3$)$_2$, and
(20) phenyloxy.

In one subclass of this class of the present invention, each R$^d$ is independently selected from:
(1) halogen,
(2) methyl,
(3) methoxy,
(4) hydroxy,
(5) CF$_3$, and
(6) —OCF$_3$.

In one embodiment of the present invention, R$^e$ and R$^f$ together with the atom(s) to which they are attached form a heterocyclic ring of 4 to 7 members containing 0-2 additional heteroatoms independently selected from oxygen, sulfur and N—R$^9$.

In one class of this embodiment, R$^e$ and R$^f$ together with the atom(s) to which they are attached form a heterocyclic ring of 5 to 6 members.

In another embodiment of the present invention, R$^e$ and R$^f$ are each independently selected from:
(1) hydrogen
(2) C$_{1-8}$ alkyl, straight chain or branched, unsubstituted or substituted with one to three substituents selected from halogen, hydroxyl, and C$_{1-6}$alkyloxy-,
(3) C$_{2-8}$ alkenyl, straight chain or branched,
(4) perfluoro C$_{1-6}$ alkyl, straight chain or branched,
(5) C$_{1-8}$ alkylcarbonyl-, straight chain or branched, unsubstituted or substituted on a carbon atom with one to three substituents selected from halogen, hydroxyl, and C$_{1-6}$alkyloxy-,
(6) C$_{1-8}$ alkylcarbonyloxy-, straight chain or branched, unsubstituted or substituted on a carbon atom with one to three substituents selected from halogen, hydroxyl, and C$_{1-6}$alkyloxy-,
(7) C$_{3-7}$cycloalkyl,
(8) cycloalkyl-C$_{1-6}$alkyl, wherein alkyl is straight chain or branched,
(9) cycloheteroalkyl,
(10) aryl, unsubstituted or substituted with one to three substituents selected from halogen, amino, carboxy, methyl, methoxy, hydroxy, trifluoromethyl, and methylcarbonyloxy,
(11) arylcarbonyl-, unsubstituted or substituted on a carbon atom with one to three substituents selected from halogen, amino, carboxy, methyl, methoxy, hydroxy, trifluoromethyl, and methylcarbonyloxy,
(12) arylcarbonyloxy-, unsubstituted or substituted on a carbon atom with one to three substituents selected from halogen, amino, carboxy, methyl, methoxy, hydroxy, trifluoromethyl, and methylcarbonyloxy,
(13) heteroaryl, unsubstituted or substituted on a carbon or nitrogen atom with one to three substituents selected from halogen, amino, carboxy, methyl, methoxy, hydroxy, trifluoromethyl, and methylcarbonyloxy,
(14) aryl $C_{1-6}$alkyl, wherein alkyl is straight chain or branched, and
(15) heteroaryl $C_{1-6}$alkyl, wherein alkyl is straight chain or branched.

In one class of this embodiment, $R^e$ and $R^f$ are each independently selected from:
(1) hydrogen
(2) $C_{1-4}$ alkyl, straight chain or branched, unsubstituted or substituted with one to three substituents selected from halogen, hydroxyl, and methoxy,
(3) alkyl,
(4) trifluoromethyl,
(5) $C_{1-4}$ alkylcarbonyl-, straight chain or branched, unsubstituted or substituted on a carbon atom with one to three substituents selected from halogen, hydroxyl, and methoxy,
(6) methylcarbonyloxy-,
(7) cyclopropyl,
(8) cyclohexyl,
(9) phenyl, unsubstituted or substituted with one to three substituents selected from halogen, amino, carboxy, methyl, methoxy, hydroxy, trifluoromethyl, and methylcarbonyloxy,
(10) phenylcarbonyl-, unsubstituted or substituted on a carbon atom with one to three substituents selected from halogen, amino, carboxy, methyl, methoxy, hydroxy, trifluoromethyl, and methylcarbonyloxy,
(11) arylcarbonyloxy-, unsubstituted or substituted on a carbon atom with one to three substituents selected from halogen, amino, carboxy, methyl, methoxy, hydroxy, trifluoromethyl, and methylcarbonyloxy,
(12) pyridyl, unsubstituted or substituted on a carbon or nitrogen atom with one to three substituents selected from halogen, amino, carboxy, methyl, methoxy, hydroxy, trifluoromethyl, and methylcarbonyloxy, and
(13) benzyl.

In one class of this embodiment, $R^e$ and $R^f$ are each independently selected from:
(1) hydrogen
(2) methyl,
(3) alkyl, and
(4) trifluoromethyl.

In one embodiment of the present invention, when X' is hydroxy, —$NR^9C(O)R^{10}$, —$NR^9C(O)OR^{10}$, —$N(R^{11})(R^{12})$, or $OR^{10}$, then $R^2$ and $R^3$ are not:
(1) both hydrogen, nor
(2) form a carbonyl group together with the carbon to which they are attached.

In another embodiment of the present invention, when X' is hydroxy, —$C(O)N(R^{11})R^{12})$, —$NR^9C(O)R^{10}$, —$NR^9C(O)OR^{10}$, —$N(R^{11})(R^{12})$, or $OR^{10}$, then $R^2$ and $R^3$ are not:
(1) both hydrogen, nor
(2) form a carbonyl group together with the carbon to which they are attached.

"Alkyl", as well as other groups having the prefix "alk", such as alkoxy, alkanoyl, means carbon chains which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, alkyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each having from 3 to 10 carbon atoms. Examples of cycloalkyl include cyclopropyl, cyclobutyl, cyclopentyl, cyclohexyl, cycloheptyl, cyclooxtyl, tetrahydronaphthyl, decahydronaphthyl, and the like.

"Aryl" means mono- or bicyclic aromatic rings containing only carbon atoms. Examples of aryl include phenyl, naphthyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzothiazolyl, furo(2,3-b)pyridyl, quinolyl, indolyl, isoquinolyl, oxazolidinyl, and the like. The heteroaryl ring may be substituted on one or more carbon atoms. In one embodiment of the present invention, heteroaryl is pyridinyl, imidazolyl, and thienyl.

"Cycloheteroalkyl" means mono- or bicyclic or bridged saturated rings containing at least one heteroatom selected from N, S and O, each of said ring having from 3 to 10 atoms in which the point of attachment may be carbon or nitrogen. Examples of "cycloheteroalkyl" include pyrrolidinyl, piperidinyl, piperazinyl, imidazolidinyl, pyranyl, tetrahydrofuranyl, morpholinyl, dioxanyl, oxanyl, azetidinyl, perhydroazepinyl, tetrahydrofuranyl, 1-thia-4-aza-cyclohexane (thiomorpholinyl), hexahydrothienopyridinyl, thienopyridinyl, azacycloheptyl, and the like. The term also includes partially unsaturated monocyclic rings that are not aromatic, such as 2- or 4-pyridones attached through the nitrogen or N-substituted-1H, 3H)-pyrimidine-2,4-diones (N-substituted uracils). The cycloheteroalkyl ring may be substituted on the ring carbons and/or the ring nitrogens.

"Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$alkyl substituent is equivalent to:

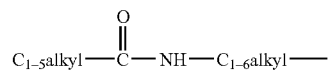

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camrsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or prodrug formulations.

It will be understood that, as used herein, references to the compounds of Formula I are meant to also include the pharmaceutically acceptable salts.

Compounds of the present invention are modulators of the CB1 receptor. In particular, the compounds of structural formula I are antagonists or inverse agonists of the CB1 receptor.

An "agonist" is a compound (hormone, neurotransmitter or synthetic compound) which binds to a receptor and mimics the effects of the endogenous regulatory compound, such as contraction, relaxation, secretion, change in enzyme activity, etc. An "antagonist" is a compound, devoid of intrinsic regulatory activity, which produces effects by interfering with the binding of the endogenous agonist or inhibiting the action of an agonist. An "inverse agonist" is a compound which acts on a receptor but produces the opposite effect produced by the agonist of the particular receptor.

Compounds of this invention are modulators of the CB1 receptor and as such are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of obesity or eating disorders associated with excessive food intake and complications associated therewith, including left ventricular hypertrophy, as well as treating or preventing obesity in other mammalian species, including canines and felines. The compounds are also useful for the treatment of constipation and chronic intestinal pseudo-obstruction. The compounds are also useful for the treatment of cirrhosis of the liver. The compounds are also useful for the treatment of asthma.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the mammalian patient in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-181); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); f) reduction in opiate self-administration in mice (Sci. 1999, 283, 401-404); g) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leukocyte recruitment and bronchial hyperresponsiveness in the guinea-pig." Eur. J. Pharmacol., 282, 243 (1995)); h) mediation of the vasodilated state in advanced liver cirrhosis induced by carbon tetrachloride (Nature Medicine, 2001, 7 (7), 827-832); i) amitriptyline-induced constipation in cynomolgus monkeys is beneficial for the evaluation of laxatives (Biol. Pharm Bulletin (Japan), 2000, 23(5), 657-9); j) neuropathology of paediatric chronic intestinal pseudo-obstruction and animal models related to the neuropathology of paediatric chronic intestinal pseudo-obstruction (Journal of Pathology (England), 2001, 194 (3), 277-88).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day. In one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 750 or 1000 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or companion animal such as a dog or cat, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those well known to those of ordinary skill in that art. To be administered in the form of a transdermal delivery system, the dosage administration will, of course, be continuous rather than intermittent throughout the dosage regimen.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet cachet or capsule contains from about 0.01 to 1,000 mg, particularly 0.01, 0.05, 0.1, 0.5, 1.0, 2.5, 3, 5, 6, 10, 15, 25, 30, 40, 50, 75, 100, 125, 150, 175, 180, 200, 225, 250, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Capsule | mg/capsule |
|---|---|
| Compound of Formula I | 25 |
| Lactose Powder | 573.5 |
| Magnesium Stearate | 1.5 |
| | 600 |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, anxiolytics, anti-Parkinson's agents, anti-epileptics, anorectic agents, serotonin reuptake inhibitors, other anti-obesity agents, as well as antidiabetic agents, lipid lowering agents, and antihypertensive agents which may be administered separately or in the same pharmaceutical compositions.

The present invention also provides a method for the treatment or prevention of a CB1 receptor modulator mediated disease, which method comprises administration to a patient in need of such treatment or at risk of developing a CB1 receptor modulator mediated disease of an amount of a CB1 receptor modulator and an amount of one or more active ingredients, such that together they give effective relief.

In a further aspect of the present invention, there is provided a pharmaceutical composition comprising a CB1 receptor modulator and one or more active ingredients, together with at least one pharmaceutically acceptable carrier or excipient.

Thus, according to a further aspect of the present invention there is provided the use of a CB 1 receptor modulator and one or more active ingredients for the manufacture of a medicament for the treatment or prevention of a CB1 receptor modulator mediated disease. In a further or alternative aspect of the present invention, there is therefore provided a product comprising a CB1 receptor modulator and one or more active ingredients as a combined preparation for simultaneous, separate or sequential use in the treatment or prevention of CB1 receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anorectic agent, such that together they give effective relief.

Suitable anorectic agents of use in combination with a compound of the present invention include, but are not limited to, aminorex, amphechloral, amphetamine, benzphetainine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof Particularly preferred halogenated amphetamine derivatives of use in combination with a compound of the present invention include: fenfluramine and dexfenfluramine, and pharmaceutically acceptable salts thereof.

The present invention also provides a method for the treatment or prevention of obesity, which method comprises administration to a patient in need of such treatment an amount of a compound of the present invention and an amount of another agent useful in treating obesity and obesity-related conditions, such that together they give effective relief.

Suitable agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone; rosiglitazone; troglitazone; BRL49653; CLX-0921; 5-BTZD, and GW-0207, LG-100641, and LY-300512, and the like and compounds disclosed in WO97/10813, 97/27857, 97/28115, 97/28137, 97/27847, 03/000685, 03/027112, 03/035602, 03/048130, 03/055867, and the like; (2) biguanides such as buformin; metformin; and phenformin, and the like; (3) protein tyrosine phosphatase-1B (PTP-1B) inhibitors, such as ISIS 113715, and those disclosed in WO 03/032916, WO 03/032982, WO 03/041729, WO 03/055883; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride; and A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-$NH_2$), and the like; (12) non-thiazolidinediones such as JT-501, and farglitazar (GW-2570/GI-262579), and the like; (13) PPARα/γ dual agonists such as BVT-142, CLX-0940, GW-1536, GW1929, GW-2433, KRP-297, L-796449, LR-90, MK-0767, SB 219994, muraglitazar and reglitazar (JTT-501) and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/004458, WO 03/016265, WO 03/018010, WO 03/033481, WO 03/033450, WO 03/033453, WO 03/043985, WO 03/053976; and (14) other insulin sensitizing drugs; (15) VPAC2 receptor agonists; (16) GLK modulators, such as those disclosed in WO 03/015774; (17) retinoid modulators such as those disclosed in WO 03/000249; (18) GSK 3beta/GSK 3 inhibitors such as 4-[2-(2-bromophenyl)-4-(4-fluorphenyl-1H-imidazol-5-yl]pyridine and those compounds disclosed in WO 03/024447, WO 03/037869, WO 03/037877, WO 03/037891, WO 03/068773, EP 1295884, EP 1295885, and the like; (19) glycogen phosphorylase (HGLPa) inhibitors, such as those disclosed in WO 03/037864; (20) ATP consumption promotors such as those disclosed in WO 03/007990; (21) TRB3 inhibitors, (22) vanilloid receptor ligands such as those disclosed in WO 03/049702, (23) hypoglycemic agents such as those disclosed in WO 03/015781, WO 03/040114, (24) glycogen synthase kinase 3 inhibitors such as those disclosed in WO 03/035663, (25) and agents such as those disclosed in WO 99/51225 and US 20030134890; and WO 01/24786, WO 03/059870; (26) Insulin-responsive DNA binding protein-1 (IRDBP-1) as disclosed in WO 03/057827, and the like; (27) Adenosine A2 antagonists such as those disclosed in WO 03/035639, WO 03/035640, and the like; and (b) lipid lowering agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, fluvastatin, lovastatin, pravastatin, rivastatin, rosuvastatin, simvastatin, and ZD-4522, and the like and compounds disclosed in WO 03/033481; (3) HMG-CoA synthase inhibitors; (4) cholesterol absorption inhibitors such as stanol esters, beta-sitosterol, sterol glycosides such as tiqueside; and azetidinones such as ezetilibe, and the like; (5) acyl coenzyme A -cholesterol acyl transferase (ACAT) inhibitors such as avasimibe, eflucimibe, KY505, SMP 797, and the like; (6) CETP inhibitors such as JTT 705, torcetrapib, CP 532,632, BAY63-2149, SC 591, SC 795, and the like; (7) squalene synthetase inhibitors; (8) anti-oxidants such as probucol, and the like; (9) PPARα agonists such as beclofibrate, benzafibrate, ciprofibrate, clofibrate, etofibrate, fenofibrate, gemcabene, and gemfibrozil, GW 7647, BM 170744, LY518674; and other fibric acid derivatives, such as Atromid®, Lopid® and Tricor®, and those disclosed in WO 03033456, WO 03/033481, WO 03/043997, WO 03/048116, WO 03/053974, WO 03/059864, WO 03/05875, and the like; (10) FXR receptor modulators such as GW 4064, SR 103912, and the like; (11) LXR receptor modulators such as GW 3965, T9013137, and XTCO179628, and those disclosed in US 20030125357, WO 03/045382, WO 03/053352, WO 03/059874, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; (16) PPARδ agonists such as GW 501516, and GW 590735, and the like, such as those disclosed in WO97/28149, WO 01/79197, WO 02/14291, WO 02/46154, WO 02/46176, WO 02/076957, WO 03/016291, WO 03/033493; (17) triglyceride synthesis inhibitors; (18) microsomal triglyceride transport (MTTP) inhibitors, such as inplitapide, LAB687, and CP346086, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists; (25) PPAR modulators such as those disclosed in WO 99/07357, WO 99/11255, WO 9912534, WO 99/15520, WO 99/46232, WO 00/12491, WO 00/23442, WO 00/236331, WO 00/236332, WO 00/218355,WO 00/238553, WO 01/25181, WO 01/79150, WO 02/79162, WO 02/100403,WO 02/102780, WO 02/081428, WO 03/016265, WO 03/033453, WO 03/042194, WO 03/043997, WO 03/066581, and the like; (26) niacin-bound chromium, as disclosed in WO 03/039535; (27) substituted acid derivatives disclosed in WO 03/040114; (28) apolipoprotein B inhibitors such as those disclosed in WO 02/090347, WO 02/28835, WO 03/045921, WO 03/047575; (29) Factor Xa modulators such as those disclosed in WO 03/047517, 35 WO 03/047520, WO 03/048081, and the like; and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as candesartan, eprosartan, irbesartan, losartan, pratosartan, tasosartan, telmisartan, valsartan, and EXP-3137, FI6828K, and $RNH_{6270}$, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663; (2) NE (norepinephrine) transporter inhibitors, such as GW 320659, despiramine, talsupram, and nomifensine; (3) CB1 (cannabinoind-1 receptor) antagonist/inverse agonists, such as rimonabant (Sanofi Synthelabo), SR-147778 (Sanofi Synthelabo), BAY 65-2520 (Bayer), and SLV 319 (Solvay), and those disclosed in U.S. Pat. Nos. 4,973,587, 5,013,837, 5,081,122, 5,112,820, 5,292, 736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 03/086940, WO 03/084943; and U.S. Pat. No. 6,509,367 and EPO Application No. EP-658546; (4) ghrelin antagonists, such as those disclosed in WO 01/87335, and WO 02/08250; (5) H3 (histamine $H_3$) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor ($MCH_1R$) antagonists, such as T-226296 (Takeda), SNP-7941 (Synaptic), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480; and Japanese Patent Application Nos. JP 13226269, and JP 1437059; (7) MCH$_2$R (melanin concentrating hormone 2R) agonist/antagonists; (8) NPY1 (neuropeptide Y Y1) antagonists, such as BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, GW-569180A, GW-594884A, GW-587081X, GW-548118X; FR 235,208; FR226928, FR 240662, FR252384; 1229U91, GI-264879A, CGP71683A, LY-377897, LY366377, PD-160170, SR-120562A, SR-120819A, JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; European Patent Nos. EP-01010691, and EP-01044970; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A; and those disclosed in WO 01/96302, WO 01/68609, WO 02/44172, WO 02/51232, WO 02/51838, WO 02/089800, WO 02/090355, WO 03/023561, WO 03/032991, WO 03/037847; (14) BRS3 (bombesin receptor subtype 3) agonists; (15) CCK-A (cholecystokinin-A) agonists, such as AR-R 15849, GI 181771, JMV-180, A-71378, A-71623 and SR146131, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170, 292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP424,391, L-692,429 and L-163,255, and those disclosed in U.S. Pat. No. 6,358, 951, U.S. Patent Application Nos. 2002/049196 and 2002/022637; and WO 01/56592, and WO 02/32888; (19) 5HT2c (serotonin receptor 2c) agonists, such as BVT933, DPCA37215, IK264; PNU 22394; WAY161503, R-1065, and YM 348; and those disclosed in U.S. Pat. No. 3,914,250; and WO 02/36596, WO 02/48124, WO 02/10169, WO 01/66548, WO 02/44152; WO 02/51844, WO 02/40456, and WO 02/40457; (20) Mc3r (melanocortin 3 receptor) agonists; (21) Mc4r (melanocortin 4 receptor) agonists, such as CHIR86036 (Chiron); ME-10142, ME-10145, and HS-131 (Melacure), and those disclosed in WO 99/64002, WO 00/74679, WO 01/991752, WO 01/0125192, WO 01/52880, WO 01/74844, WO 01/70708, WO 01/70337, WO 01/91752, WO 02/059095, WO 02/059107, WO 02/059108, WO 02/059117, WO 02/06276, WO 02/12166, WO 02/11715, WO 02/12178, WO 02/15909, WO 02/38544, WO 02/068387, WO 02/068388, WO 02/067869, WO 02/081430, WO 03/06604, WO 03/007949, WO 03/009847, WO 03/009850, WO 03/013509, and WO 03/031410; (22) monoamine reuptake inhibitors, such as sibutratmine (Meridia®/Reductil®) and salts thereof, and those compounds disclosed in U.S. Pat. Nos. 4,746,680, 4,806,570, and 5,436, 272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644, 673); (27) ACC2 (acetyl-CoA carboxylase-2) inhibitors; (28) β3 (beta adrenergic receptor 3) agonists, such as AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114, N-5984 (Nisshin Kyorin), LY-377604 (Lilly), and SR 59119A, and those disclosed in U.S. Pat. Nos. 5,705,515, 5,451,677; and WO94/18161, WO95/29159, WO97/46556, WO98/04526 and WO98/32753, WO 01/74782, WO 02/32897, WO 03/014113, WO 03/016276, WO 03/016307, WO 03/024948, WO 03/024953; and WO 03/037881; (29) DGAT1 (diacylglycerol acyltransferase 1) inhibitors; (30) DGAT2 (diacylglycerol acyltransferase 2)inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7, 8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoylestrone, disclosed in del Mar-Grasa, M. et al., Obesity Research, 9:202-9 (2001); (36) glucocorticoid antagonists; (37) 11β HSD-1 (11-beta hydroxy steriod dehydrogenase type 1) inhibitors, such as BVT 3498, BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, WO 01/90090, WO 01/90092 and WO 02/072084; (38) SCD-1 (stearoyl-CoA desaturase-1) inhibitors; (39) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444; and the compounds disclosed in WO 02/083128, WO 02/062764, WO 03/000180, WO 03/000181, WO 03/000250, WO 03/002530, WO 03/002531, WO 03/002553, WO 03/002593, WO 03/004498, WO 03/004496, WO 03/017936, WO 03/024942, WO 03/024965, WO 03/033524, WO 03/037327 and EP 1 258 476; (40) lipase inhibitors, such as tetrahydrolipstatin (orlistat/Xenical®), Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, and U.S. Pat. Nos. 4,598,089, 4,452,813, 5,512,565, 5,391,571, 5,602,151, 4,405,644, 4,189,438, and 4,242,453; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as those disclosed in WO 03/026591; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041; (50) appetite suppressants such as those in WO 03/40107; (51) 5HT6 receptor modulators, such as those in WO 03/030901, WO 03/035061, WO 03/039547, and the like; (52) 5HT1a modulators such as those disclosed in WO 03/031439, and the like; (53) mGluR5 modulators such as those disclosed in WO 03/029210, WO 03/047581, WO 03/048137, WO 03/051315, WO 03/051833, WO 03/053922, WO 03/059904, and the like; (54) 5HT antagonists such as those in WO 03/037871, WO 03/037887, and the like; (55) fat resorption inhibitors such as those in WO 03/053451, and the like; (56) interleukin-6 (IL-6) and modulators thereof, as in WO 03/057237, and the like.

Specific NPY5 antagonists of use in combination with a compound of the present invention include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-5-phenyl-2-pyrimidinyl)spiro[cyclohexane-1,1'(3'H)-isobenzofuran]4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1(3H),1'-cyclohexane]4'-carboxamide, and pharmaceutically acceptable salts and esters thereof.

Specific DP-IV inhibitors of use in combination with a compound of the present invention are selected from:

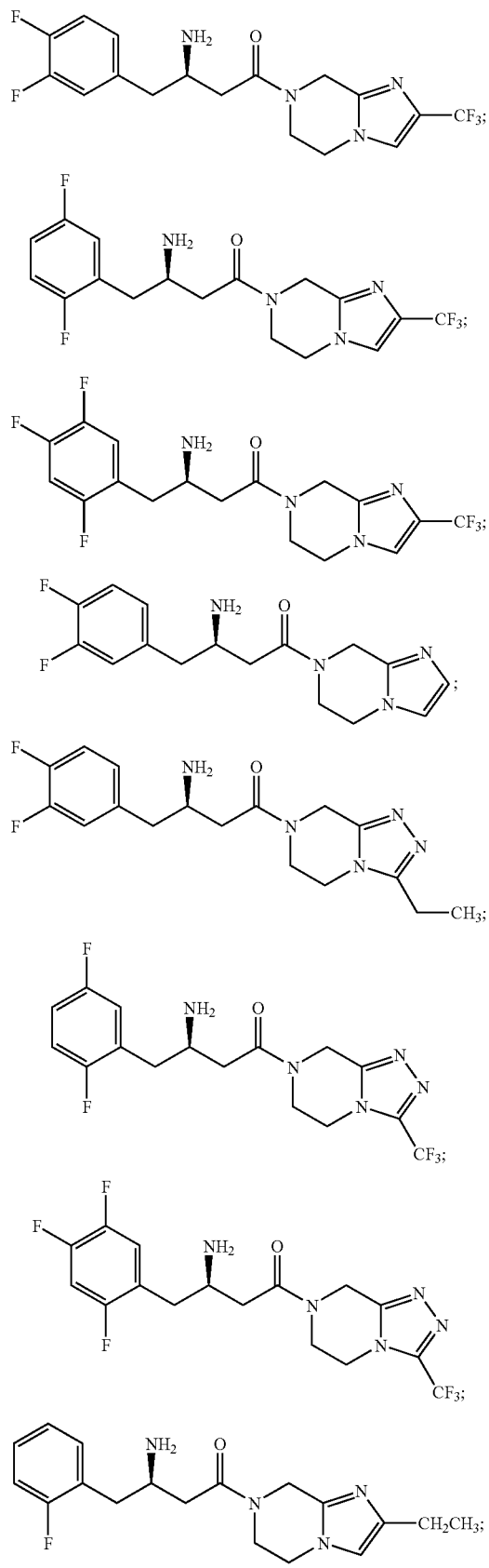

-continued

-continued

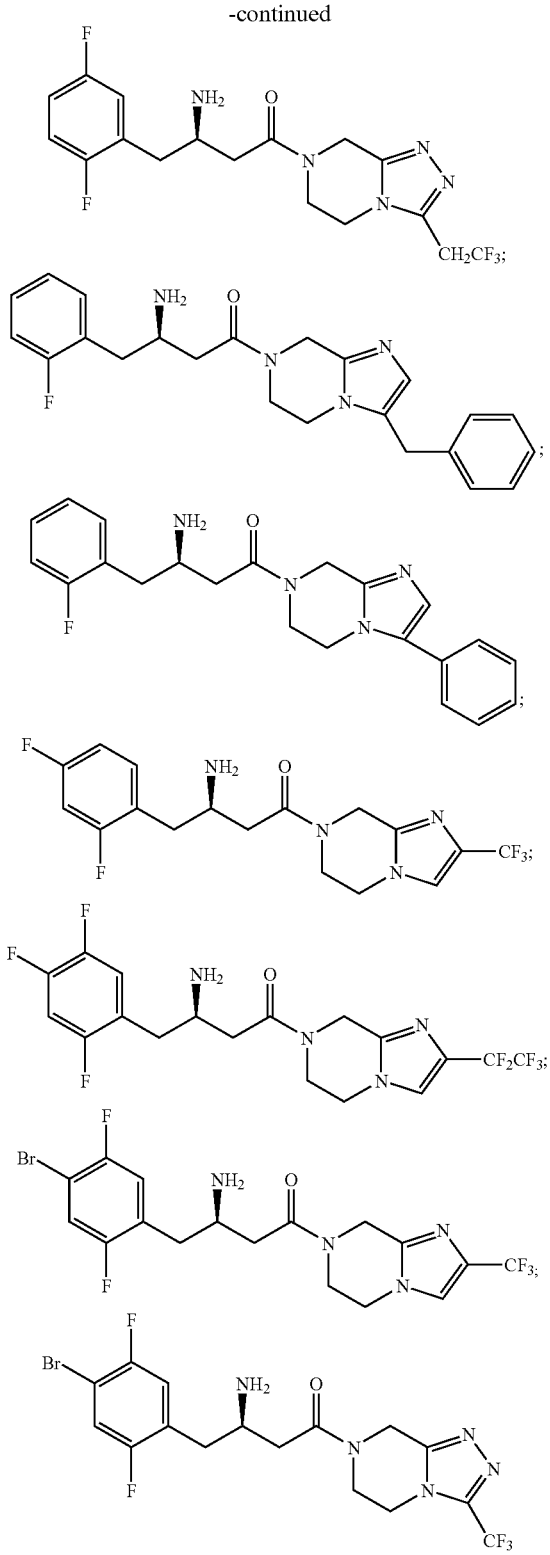

and pharmaceutically acceptable salts thereof.

"Obesity" is a condition in which there is an excess of body fat. The operational definition of obesity is based on the Body Mass Index (BMI), calculated as body weight per height in meters squared (kg/m$^2$). "Obesity" refers to a condition whereby an otherwise healthy subject has a Body Mass Index (BMI) greater than or equal to 30 kg/m$^2$, or a condition whereby a subject with at least one co-morbidity has a BMI greater than or equal to 27 kg/m$^2$. An "obese subject" is an otherwise healthy subject with a Body Mass Index (BMI) greater than or equal to 30 kg/m$^2$ or a subject with at least one co-morbidity with a BMI greater than or equal to 27 kg/m$^2$. A "subject at risk for obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asian countries, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrhythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The compounds of formula I are also useful for treating or preventing obesity and obesity-related disorders in cats and dogs. As such, the term "mammal" includes companion animals such as cats and dogs.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

It will be appreciated that for the treatment or prevention of migraine, a compound of the present invention may be used in conjunction with other anti-migraine agents, such as ergotamines or 5-$HT_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RINAs), serotonin and noradrenaline reuptake inhibitors (SNRIs), corticotropin releasing factor (CRF) antagonists, α-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine, imipramine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677. Still further, neurokinin-1 (NK-1) receptor antagonists may be favorably employed with the CB1 receptor modulators of the present invention. NK-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833, 5,637,699; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, 97/49710, 98/24438-98/24441, 98/24442-98/24445, 02/16343, and 02/16344; and in British Patent Publication Nos. 2 266 529, 2 268 931, 2 269 170, 2 269 590, 2 271 774, 2 292 144, 2 293 168, 2 293 169, and 2 302 689.

Specific neurokinin-1 receptor antagonists of use in the present invention include: (±)-(2R3R,2S3S)-N-{[2-cyclopropoxy-5-(trifluoromethoxy)-phenyl]methyl }-2-phenylpiperidin-3-amine; 2-(R)-(1-(R)-(3,5-bis(trifluoromethyl)phenyl)ethoxy)-3-(S)-4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763; or a pharmaceutically acceptable salt thereof.

Suitable atypical anti-depressants include: bupropion, lithium, nefazodone, trazodone and viloxazine, and pharmaceutically acceptable salts thereof.

Suitable classes of anti-anxiety agents include benzodiazepines and $5\text{-}HT_{1A}$ agonists or antagonists, especially $5\text{-}H_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable $5\text{-}HT_{1A}$ receptor agonists or antagonists include, in particular, the $5\text{-}HT_{1A}$ receptor partial agonists buspirone, flesinoxan, gepirone and ipsapirone, and pharmaceutically acceptable salts thereof.

Suitable corticotropin releasing factor (CRF) antagonists include those previously discussed herein.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

In particular, compounds of structural formula I are useful for aiding in stopping consumption of tobacco and are useful in treating nicotine dependence and nicotine withdrawal. The compounds of formula I produce in consumers of nicotine, such as tobacco smokers, a total or partial abstinence from smoking. Further, withdrawal symptoms are lessened and the weight gain that generally accompanies quitting tobacco consumption is reduced or nonexistent. For smoking cessation, the compound of form I may be used in combination with a nicotine agonist or a partial nicotine agonist, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania.

The present invention also provides a method for the treatment or prevention of mania, which method comprises administration to a patient in need of such treatment or at risk of developing mania of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient.

It will be appreciated that the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania.

It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of CB1 receptor modulators in combination with an antipsychotic agent in the treatment or prevention of hypomania.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a CB1 receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a CB1 receptor modulator is the 5-$HT_{2A}$ receptor antagonists, examples of which include MDL100907 and fananserin. Also of use in combination with a CB 1 receptor modulator are the serotonin dopamine antagonists (SDAs) which are believed to combine 5-$HT_{2A}$ and dopamine receptor antagonist activity, examples of which include olanzapine and ziperasidone.

Still further, NK-1 receptor antagonists may be favorably employed with the CB1 receptor modulators of the present invention. Preferred NK-1 receptor antagonists for use in the present invention are selected from the classes of compounds described previously.

It will be appreciated that a combination of a conventional anti-asthmatic drug with a CB1 receptor modulator may provide an enhanced effect in the treatment of asthma, and may be used for the treatment or prevention of asthma, which method comprises administration to a patient in need of such treatment an amount of a compound of the present invention and an amount of an anti-asthmatic agent, such that together they give effective relief.

Suitable anti-asthmatic agents of use in combination with a compound of the present invention include, but are not limited to: (a) VLA-4 antagonists such as natalizumab and the compounds described in U.S. Pat. No. 5,510,332, WO97/03094, WO97/02289, WO96/40781, WO96/22966, WO96/20216, WO96/01644, WO96/06108, WO95/15973 and WO96/31206; (b) steroids and corticosteroids such as beclomethasone, methylprednisolone, betamethasone, prednisone, dexamethasone, and hydrocortisone; (c) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (d) non-steroidal anti-asthmatics including β2-agonists (such as terbutaline, metaproterenol, fenoterol, isoetharine, albuterol, bitolterol, salmeterol, epinephrine, and pirbuterol), theophylline, cromolyn sodium, atropine, ipratropium bromide, leukotriene antagonists (such as zafirlukast, montelukast, pranlukast, iralukast, pobilukast, and SKB-106,203), and leukotriene biosynthesis inhibitors (such as zileuton and BAY-1005); (e) anti-cholinergic agents including muscarinic antagonists (such as ipratropium bromide and atropine); and (f) antagonists of the chemokine receptors, especially CCR-3; and pharmaceutically acceptable salts thereof.

It will be appreciated that a combination of a conventional anti-constipation drug with a CB1 receptor modulator may provide an enhanced effect in the treatment of constipation or chronic intestinal pseudo-obstruction, and for use for the manufacture of a medicament for the treatment or prevention of constipation or chronic intestinal pseudo-obstruction.

The present invention also provides a method for the treatment or prevention of constipation, which method comprises administration to a patient in need of such treatment an amount of a compound of the present invention and an amount of an anti-constipation agent, such that together they give effective relief.

Suitable anti-constipation agents of use in combination with a compound of the present invention include, but are not limited to, osmotic agents, laxatives and detergent laxatives (or wetting agents), bulking agents, and stimulants; and pharmaceutically acceptable salts thereof. A particularly suitable class of osmotic agents include, but are not limited to sorbitol, lactulose, polyethylene glycol, magnesium, phosphate,and sulfate; and pharmaceutically acceptable salts thereof. A particularly suitable class of laxatives and detergent laxatives, include, but are not limited to, magnesium, and docusate sodium; and pharmaceutically acceptable salts thereof. A particularly suitable class of bulking agents include, but are not limited to, psyllium, methylcellulose, and calcium polycarbophil; and pharmaceutically acceptable salts thereof. A particularly suitable class of stimulants include, but are not limited to, anthroquinones, and phenolphthalein; and pharmaceutically acceptable salts thereof.

It will be appreciated that a combination of a conventional anti-cirrhosis drug with a CB1 receptor modulator may provide an enhanced effect in the treatment or prevention of cirrhosis of the liver, and for use for the manufacture of a medicament for the treatment or prevention of cirrhosis of the liver.

The present invention also provides a method for the treatment or prevention of cirrhosis of the liver, which method comprises administration to a patient in need of such treatment an amount of a compound of the present invention and an anti-cirrhosis agent, such that together they give effective relief.

Suitable anti-cirrhosis agents of use in combination with a compound of the present invention include, but are not limited to, corticosteroids, penicillamine, colchicine, interferon-γ, 2-oxoglutarate analogs, prostaglandin analogs, and other anti-inflammatory drugs and antimetabolites such as azathioprine, methotrexate, leflunamide, indomethacin, naproxen, and 6-mercaptopurine; and pharmaceutically acceptable salts thereof.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations used in the following Schemes and Examples:

aq or aq.: aqueous; BOC or boc: benzyloxycarbonyl; brine: saturated sodium chloride solution; Bu: butyl; DAST: diethylaminosulfur trifluoride; DBU: 1,8-diazabicyclo[5.4.0]undec-7-ene; DIBAL-H: diisobutyl aluminum hydride; DMAP: 4-dimethylaminopyridine; DMF: dimethylformamide; DMSO: dimethylsulfoxide; EDAC: 1-ethyl-3-(3,3-diethylaminopropyl)-carbodiimide hydrochloride; Et: ethyl; g or gm: gram; h or hr: hours; HOAc: acetic acid; HOBT: 1-hydroxybenzotriazole; HPLC: high pressure liquid chromatography; HPLC/MS: high pressure liquid chromatography/ mass spectroscopy; in vacuo: rotoevaporation; iPr: isopropyl; LC-MS or LCMS: liquid chromatography-mass spectrum; LHMDS: Lithium Hexamethyl Disilylamide-LiN(SiMe$_3$)$_2$; M: molar; mCPBA: 3-chloroperbenzoic acid; Me: methyl; mg: milligram; MHz: megahertz; min: minutes; mL: milliliter; mmol: millimole; MPLC: medium pressure liquid chromatography; MS or ms: mass spectrum; Ms: mesyl (methane sulfonyl); N/A: Not applicable; NaHMDS: sodium hexamethyl disilylamide; Ox-Cl: oxalyl chloride; Ph: phenyl; psi: pounds per square inch; rt or RT: room temperature; R$_t$: retention time; TFA: trifluoroacetic acid; THF: tetrahydrofuran; TLC: thin layer chromatography; μL, μl, μL or μl: microliter; UV: ultra-violet.

Compounds of the present invention may be prepared by procedures illustrated in the accompanying schemes.

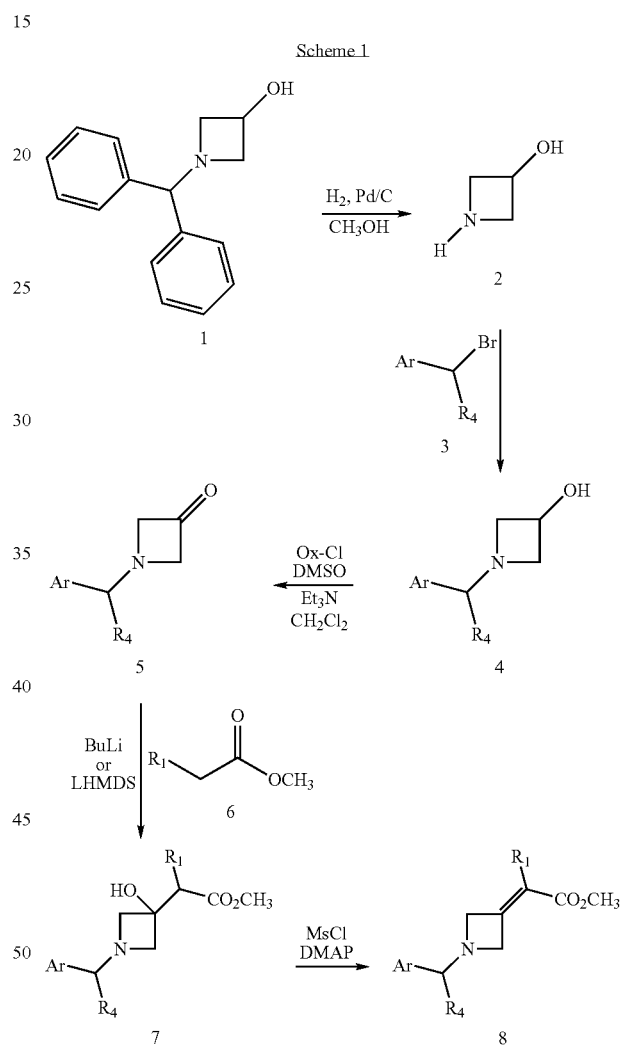

In Scheme 1, the starting material is the commercially available 1-(dimethylphenyl)-3-hyroxyazetidine (Oakwood Products, Inc.). The benzhydryl group of 1 is removed by catalytic hydrogenation in an alcoholic solvent using a palladium-charcoal catalyst and 50 psi hydrogen to afford the aminoalcohol 2. The amino group of 2 can be selectively alkylated with an appropriately substituted alkyl bromide 3 in the presence of a base such as diisopropylethylamine in an aprotic solvent such as THF to afford 4. The hydroxy group of 4 can be oxidized under Swern conditions (oxalyl chloride, DMSO, Et3N, CH$_2$Cl$_2$) to afford the appropriately substituted ketone 5. A ketene acetal is formed in situ by deprotonation of an appropriately substituted ester 6 with a strong base such as butyllithium or lithium hexamethyldisilamine in an aprotic solvent such as THF at −78° C. This ketene acetal adds to the carbonyl group of 5 to afford the hydroxy ester 7. Activation of the hydroxy group of 7 with methanesulfonyl chloride or methanesulfonic anhydride in the presence of a base such as DMAP or pyridine/DBU effects elimination to afford the olefin 8.

affords the secondary alcohol 12. The hydroxy group of 12 may be oxidized to the ketone 13 under Swern conditions. Another carbanion (either the same or different from that used in the first step) is then added to the carbonyl group of 13 to form the tertiary hydroxy compound 14.

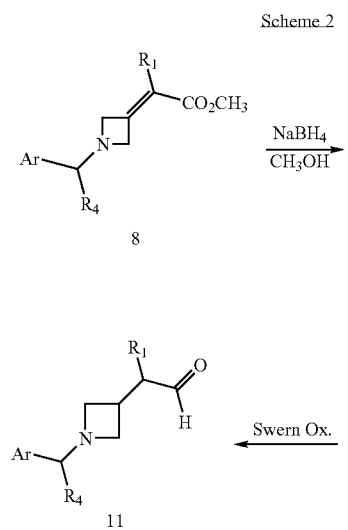

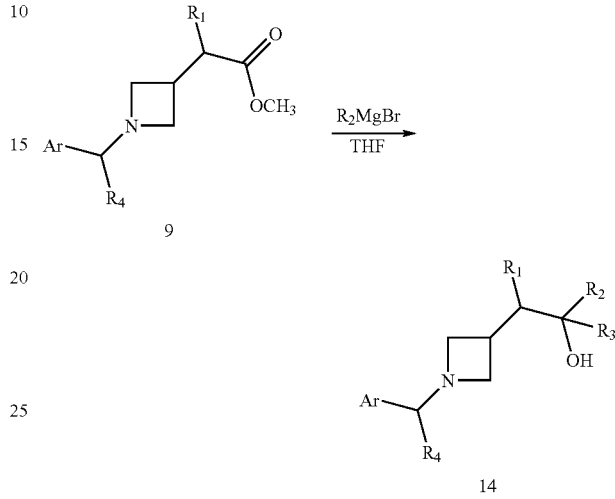

In Scheme 2, the olefin of 8 is selectively reduced to 9 using an agent such as sodium borohydride in a protic solvent like methanol. The ester of 9 is reduced to the corresponding alcohol 10 with a reagent such as lithium aluminum hydride in an aprotic solvent such as ether or THF. The hydroxy group of 10 is converted to the aldehyde 11 by oxidation under Swern conditions.

Scheme 4 illustrates the case where $R_2$ and $R_3$ are the same. Reaction of the carbonyl group of ester 9 with an excess of a carbanion such as Grignard reagent or alkyllithium reagent in an aprotic solvent such as ether or THF at low temperatures affords the tertiary alcohol 14.

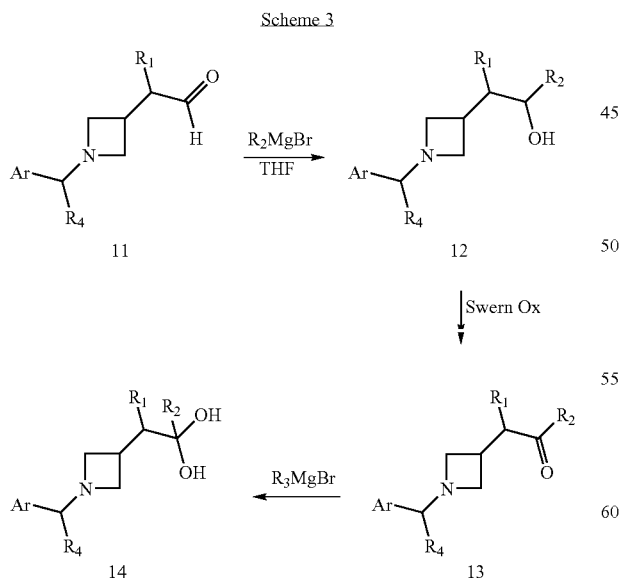

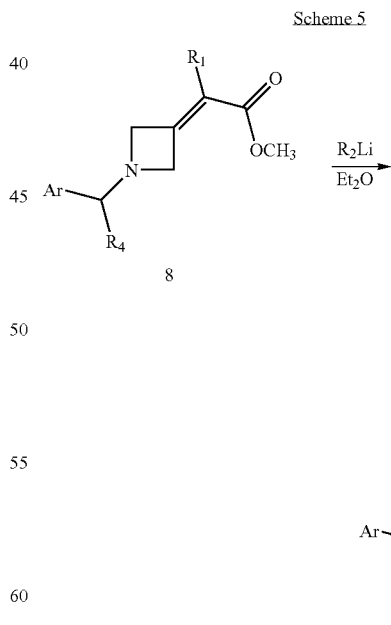

In Scheme 3, reaction of the carbonyl group of 11 with a carbanion such as Grignard reagent or alkyllithium reagent in an aprotic solvent such as ether or THF at low temperatures Scheme 6 also illustrates the case where $R_2$ and $R_3$ are the same. Reaction of the ester 8 with an excess of a carbanion such as an alkyllithium reagent in an aprotic solvent such as ether at low temperatures affords the tertiary alcohol 15.

Scheme 6

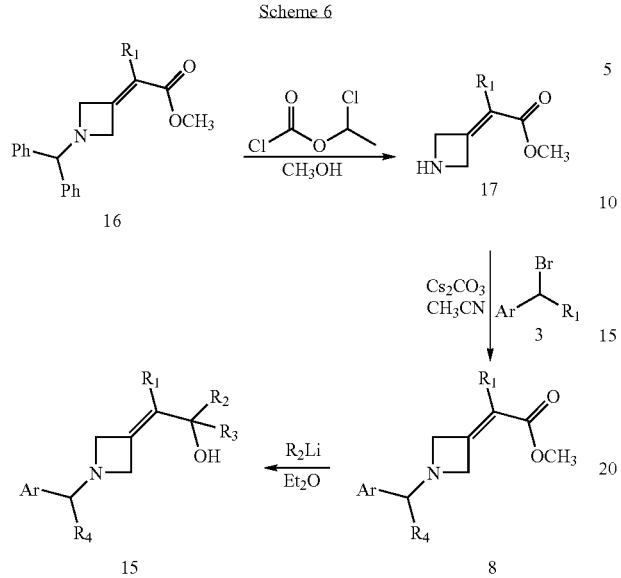

In Scheme 6, the benzhydryl group of ester 16 is selectively removed by treatment with an activating agent such as 1-chloroethyl chloroformate in THF followed by solvolysis in a nucleophilic solvent such as methanol to afford the free amine 17. The amino group of 17 is alkylated with an appropriately substituted alkyl bromide in the presence of a mild base such as cesium carbonate in an aprotic solvent such as acetonitrile to afford 8. Reaction of the ester group of 8 with an excess of a carbanion such as an alkyllithium reagent in an aprotic solvent such as ether at low temperatures affords the tertiary alcohol 15.

Scheme 7

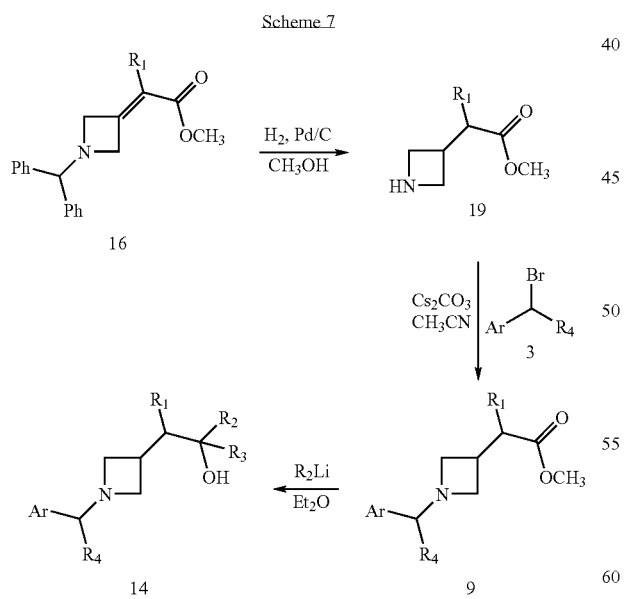

In Scheme 7, the benzhydryl group of ester 16 is removed and the olefin reduced by catalytic hydrogenation in an alcoholic solvent using a palladium-charcoal catalyst and 50 psi hydrogen to afford the aminoester 19. The amino group of 19 is alkylated with an appropriately substituted alkyl bromide in the presence of a mild base such as cesium carbonate in an aprotic solvent such as acetonitrile to afford 9. Reaction of the ester group of 9 with an excess of a carbanion such as an alkyllithium reagent in an aprotic solvent such as ether at low temperatures affords the tertiary alcohol 14.

Scheme 8

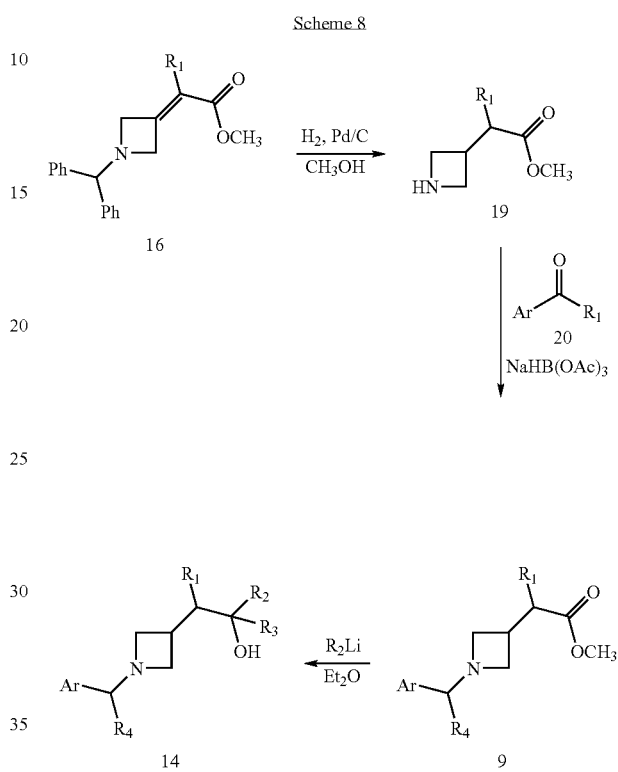

Scheme 8 depicts an alternative synthesis of 14. The benzhydryl group of ester 16 is removed and the olefin reduced by catalytic hydrogenation in an alcoholic solvent using a palladium-charcoal catalyst and 50 psi hydrogen to afford the aminoester 19. The amino group of 19 is reacted with an appropriately substituted ketone 20 in the presence of a reducing agent such as sodium triacetoxyborohydride in an aprotic solvent such as dichloroethane. Reaction of the ester group of 9 with an excess of a carbanion such as an alkyllithium or alkylcerium reagent in an aprotic solvent such as ether at low temperatures affords the tertiary alcohol 14.

Scheme 9

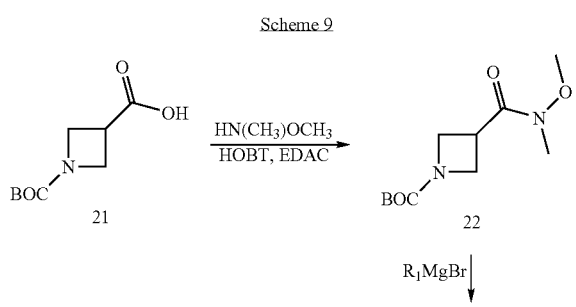

Scheme 10

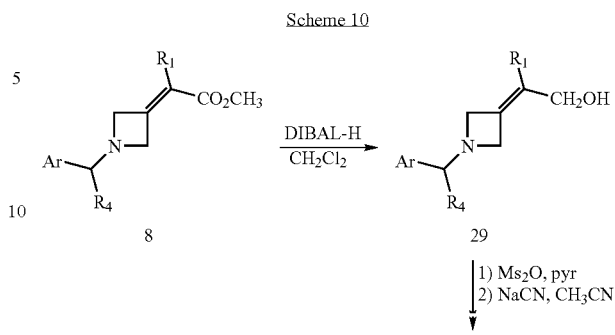

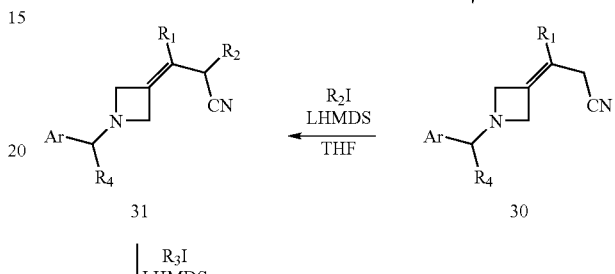

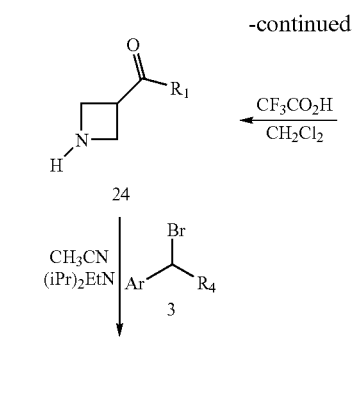

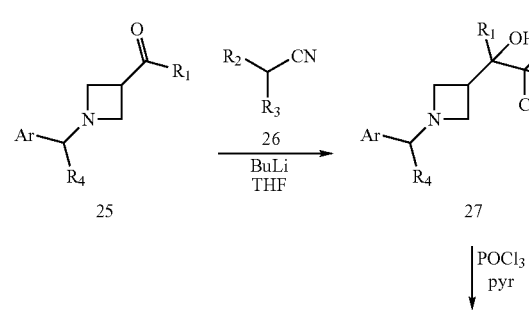

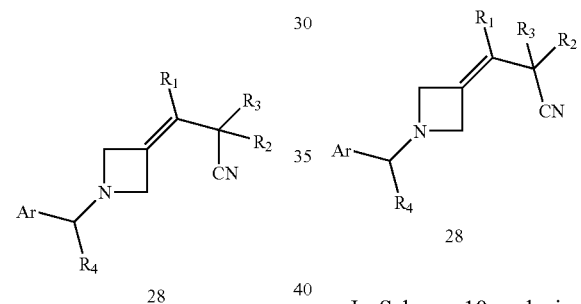

In Scheme 9, the starting material 21 is the commercially available 1-(tert-butoxycarbonyl)-azetidine-3-carboxylic acid (PepTech Corporation). The carboxy group of 21 is activated with a reagent such as EDAC (1-ethyl-3-(3,3-dimethylaminopropyl)carbodiimide hydrochloride) in the presence of N-methyl-O-methylhydroxylamine hydrochloride and HOBT in a solvent such as dichloromethane to afford amide 22. Carbanions such as an appropriately substituted Grignard reagent add selectively to the amide carbonyl group of 22 to form the ketone 23. The tert-butoxycarbonyl group of 23 is removed with trifluoroacetic acid in dichloromethane to form the amine 24, which reacts with an appropriately substituted alkyl bromide in the presence of a mild base such as diisopropylethylamine in an aprotic solvent like CH$_3$CN to afford the ketone 25. A carbanion is formed in situ by deprotonation of an appropriately substituted nitrile 26 with a strong base such as butyllithium in an aprotic solvent such as THF at –78 °C. This adds to the carbonyl group of 25 to afford the hydroxy nitrile 27. Activation of the hydroxy group of 7 with phosphorous oxychloride in the presence of a base such as pyridine effects elimination to afford the olefin 28.

In Scheme 10, reducing agents such as diisobutylaluminum hydride in an aprotic solvent such as dichloromethane add selectively to the ester carbonyl of 8 to afford the alkylic alcohyl 29. Activation of the hydroxy group of 29 with methanesulfonic anhydride in the presence of a base such as pyridine forms and displacement of the mesylate with a nucleophile such as sodium cyanide in a solvent such as acetonitrile forms the nitrile 30. The nitrite is deprotonated with a strong base such as LHMDS in an inert solvent such as THF at low temperatures and the resulting carbanion reacts with electrophiles such as an appropriately substituted alkyl iodide to afford the 31. Compound 31 may be subjected to a second round of deprotonation/alylation to form 28.

Scheme 11

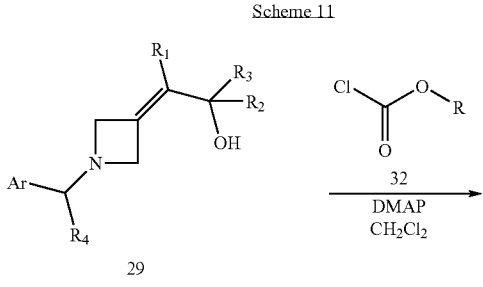

-continued

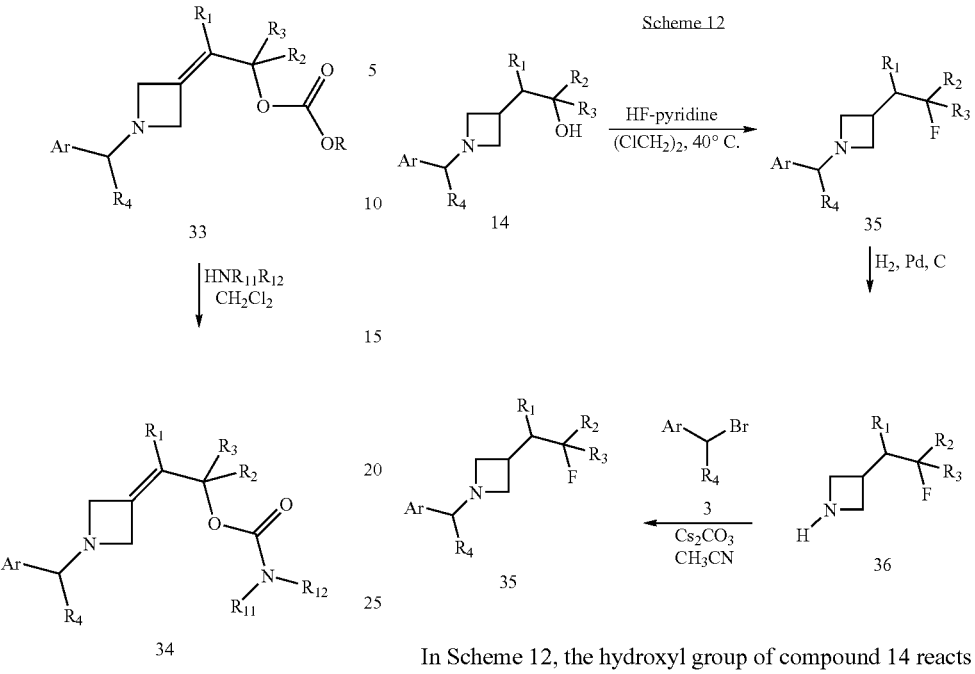

In Scheme 11, the hydroxy group of 29 is reacted with an appropriately substituted chloroformate to afford the corresponding carbonate 33. When 32 is 4-nitrophenylchloroformate, the resulting carbonate 33 is reacted with nucleophiles such as primary and secondary amines in an inert solvent such as dichloromethane to form the corresponding carbamates 34.

In Scheme 12, the hydroxyl group of compound 14 reacts under treatment with HF-pyridine complex in a solvent such as dichloroethane at 40° C. to form the corresponding fluoride 35. To change substitution on the azetidine nitrogen, the existing N-substituent may be removed by hydrogenation with a catalyst such as 10% Pd on charcoal to afford amine 36. In the latter case, the alkyl group may be replaced by alkylation with same or a differently substituted bromide 3 under conditions described in Scheme 7 to afford 35.

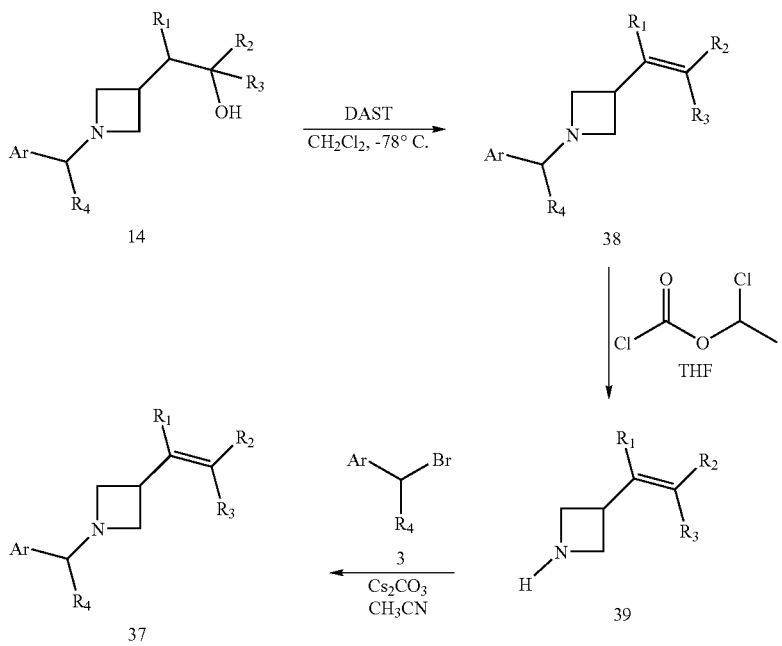

In Scheme 13, the hydroxyl group of compound 14 can be eliminated by treatment with DAST (diethylaminosulfur trifluoride) in an inert solvent such as dichloroethane to form the olefin 37. To change substitution on the azetidine nitrogen, the existing N-substiutuent may be removed by 1-chloroethyl chloroformate to afford amine 39 and the alkyl group may be replaced by alkylation with same or a differently substituted bromide 3 under conditions described in Scheme 7 to afford 37.

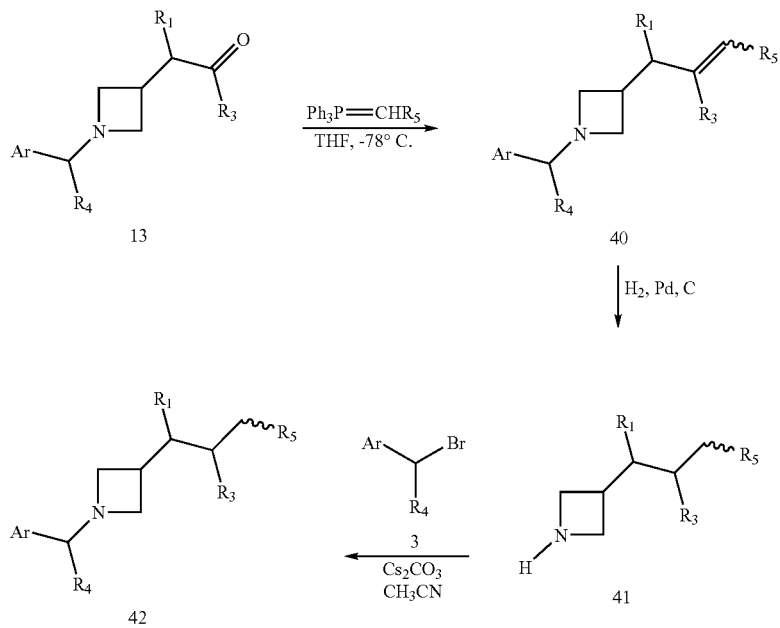

In Scheme 14, the carbonyl group of compound 13 was converted to the olefin by condensation with a Wittig reagent such as methyltriphenylphosphonium bromide that had been deprotonated with a strong base such as n-butyllithium to afford olefin 40. Hydrogenation with a catalyst such as 10% Pd on charcoal reduces the olefin and may remove the N-substiutent to afford amine 41. In the latter case, the alkyl group may be restored by alkylation with bromide 3 under conditions described in Scheme 7 to afford 42.

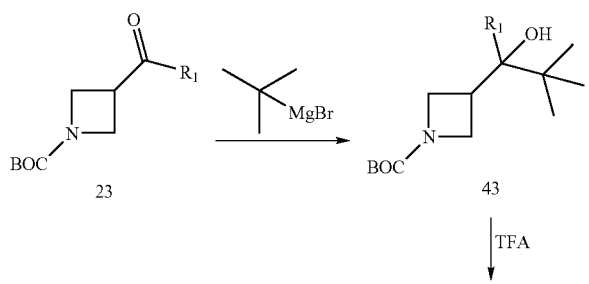

-continued

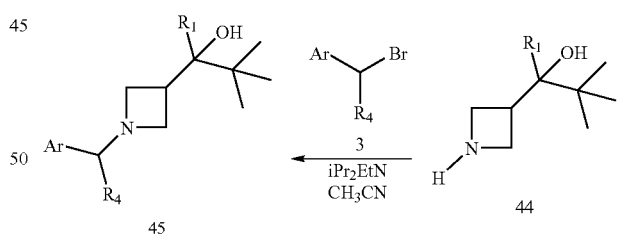

In Scheme 15, a carbanion such as tert-butylmagnesium bromide is added to the carbonyl group of compound 23 (Scheme 7) in an solvent such as THF to afford hydroxyl adduct 43. The tert-butoxycarbonyl group of 43 is removed with trifluoroacetic acid in dichloromethane to form the amine 44, which reacts with an appropriately substituted alkyl bromide in the presence of a mild base such as diisopropylethylamine or $Cs_2CO_3$ in an aprotic solvent like $CH_3CN$ to afford the alcohol 45.

Scheme 16

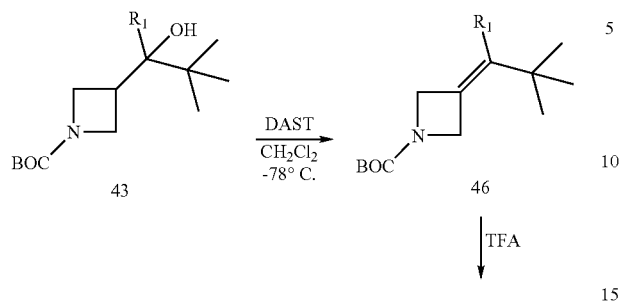

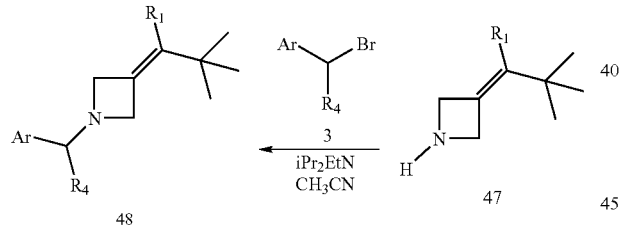

Scheme 17

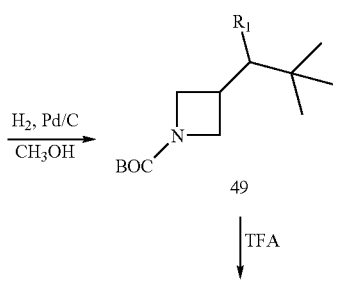

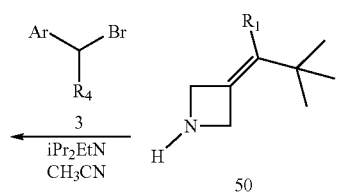

In Scheme 16, the hydroxyl group of compound 43 (Scheme 16) is eliminated by treatment with DAST (diethylaminosulfur trifluoride) in a solvent such as dichloromethane to afford olefin 46. The tert-butoxycarbonyl group of 46 is removed with trifluoroacetic acid in dichloromethane to form the amine 47, which reacts with an appropriately substituted alkyl bromide in the presence of a mild base such as diisopropylethylamine or Cs$_2$CO$_3$ in an aprotic solvent like CH$_3$CN to afford the alcohol 48.

In Scheme 17, the olefin of compound 43 (Scheme 16) is reduced by hydrogenation using a catalyst such as 10% Pd on charcoal to afford the saturated compound 49. The tert-butoxycarbonyl group of 46 is removed with trifluoroacetic acid in dichloromethane to form the amine 50, which reacts with an appropriately substituted alkyl bromide in the presence of a mild base such as diisopropylethylamine or Cs$_2$CO$_3$ in an aprotic solvent like CH$_3$CN to afford the alcohol 51.

When R$_1$ is an appropriately substituted aryl group, such as 3,5-difluorophenyl or 3-bromo-5-fluorophenyl, that aryl group may be further modified as depicted in the following schemes.

Scheme 18

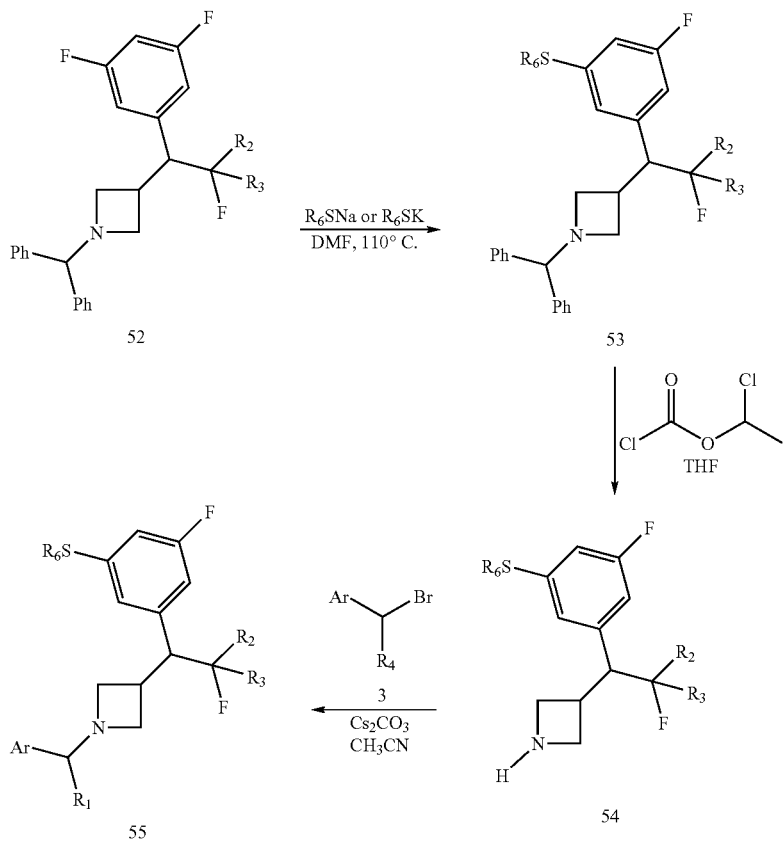

In Scheme 18, a good nucleophile such as the sodium or potassium salt of a thiol will displace one or both arylfluorides of an intermediate such as compound 52 to afford sulfide 53. The benzhydryl group of 53 is removed by treatment with 1-chloroethyl chloroformate in a solvent such as tetrahydrofuran and the resulting amine 54 reacts with an appropriately substituted alkyl bromide in the presence of a mild base such as diisopropylethylamine or $Cs_2CO_3$ in an aprotic solvent like $CH_3CN$ to afford the sulfide 55.

Scheme 19

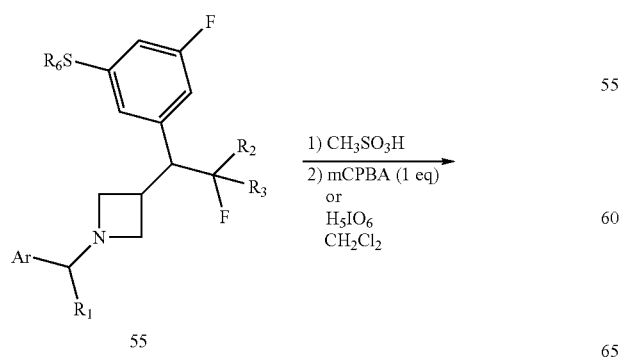

-continued

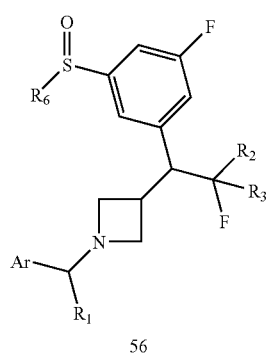

In Scheme 19, the sulfide of compound 55 is partially oxidized to the sulfoxide 53. Before oxidation, the amino group of 56 must be protonated with a strong acid such as methanesulfonic acid in an solvent such as dichloromethane. Once protonation has occurred, the sulfide may be oxidized to the sulfoxide with an oxidant such as periodic acid or by adding a limited amount of a stronger oxidant such as 3-chloroperbenzoic acid.

Scheme 20

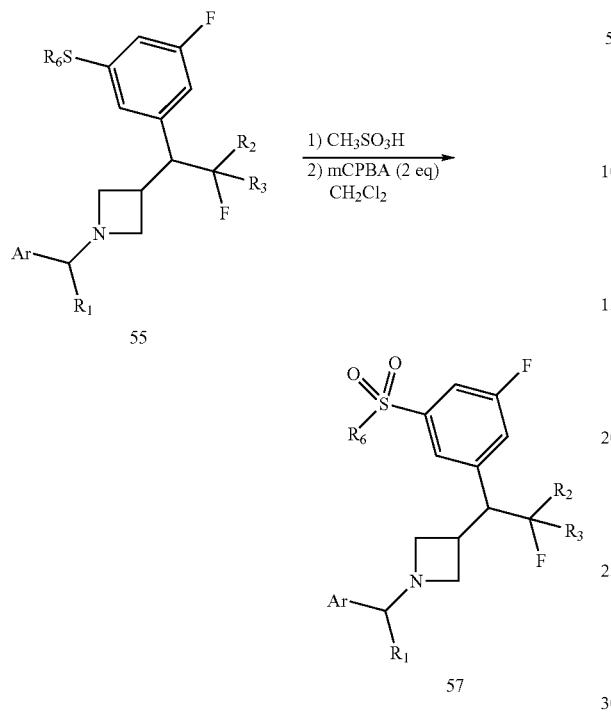

Scheme 21

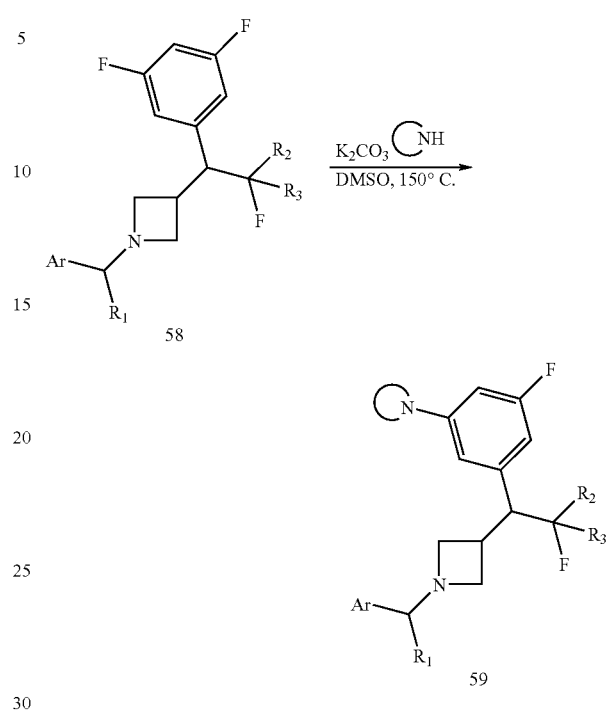

In Scheme 20, the sulfide of compound 55 is completely oxidized to the sulfone 57. Before oxidation, the amino group of 55 must be protonated with a strong acid such as methanesulfonic acid in an solvent such as dichloromethane. Once protonation has occurred, the sulfide may be oxidized to the sulfone 57 with an excess of an oxidant 3-chloroperbenzoic acid in dichloromethane.

In Scheme 21, the nitrogen group of a nitrogen-containing heterocycle such as imidazole or 1,2,4-triazole will displace one or both arylfluorides of an intermediate such as compound 58 at high temperatures in a polar aprotic solvent such as dimethylsulfoxide and in the presence of a base such as potassium carbonate to afford amines 59.

Scheme 22

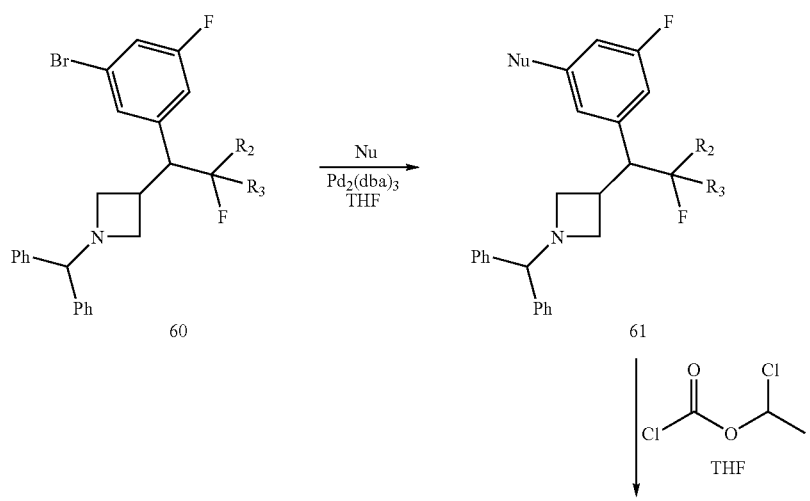

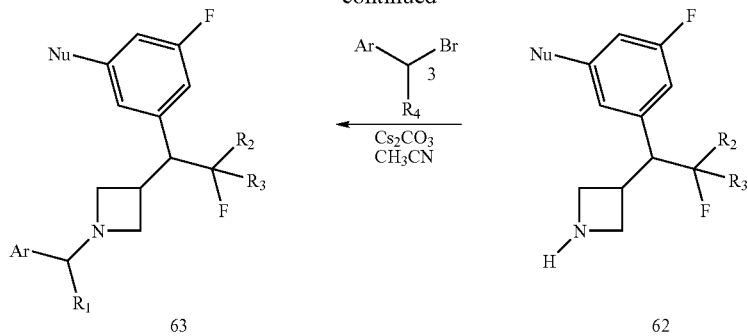

In Scheme 22, the bromo group of compound 60 can be selectively replaced by a nucleophile such as Zn(CN)$_2$ or LADS in the presence of a palladium catalyst such as Pd$_2$(dba)$_3$ to afford the corresponding aryl-substituted analog 61. The benzhydryl group of 50 is removed by treatment with 1-chloroethyl chloroformate in a solvent such as tetrahydrofuran and the resulting amine 62 reacts with an appropriately substituted alkyl bromide in the presence of a mild base such as diisopropylethylamine or Cs$_2$CO$_3$ in an aprotic solvent like CH$_3$CN to afford 63.

In Scheme 23, the amino group of compound 64 (Scheme 22) can be converted to a heterocycle such as 1,3,4-triazole 65 by treatment with a reagent such as N'-[(1E)-(dimethylamino)methylene]-N,N-dimethylhydrazonoformamide in the presence of an acid catalyst at elevated temperature in an inert solvent such as toluene. The benzhydryl group of 65 is removed by treatment with 1-chloroethyl chloroformate in a solvent such as tetrahydrofuran and the resulting amine 66 reacts with an appropriately substituted alkyl bromide in the

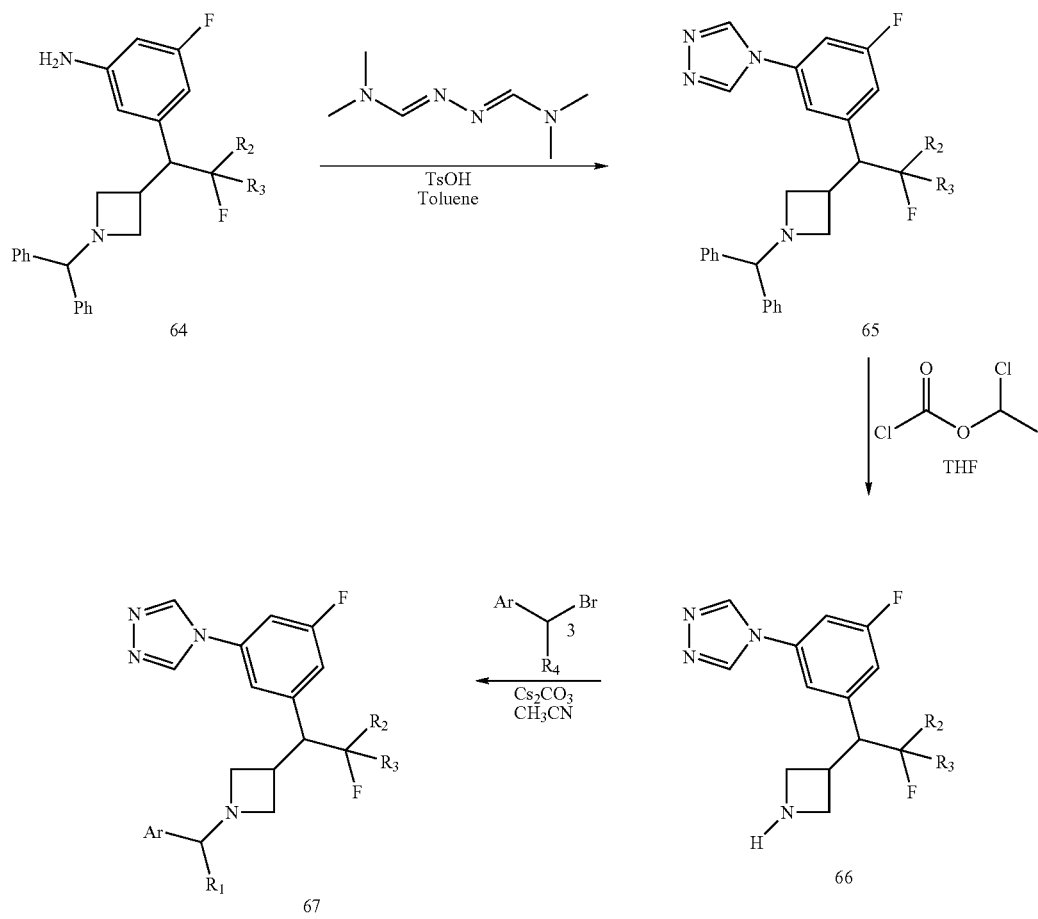

presence of a mild base such as diisopropylethylamine or Cs₂CO₃ in an aprotic solvent like CH₃CN to afford 67.

PREPARATION 1

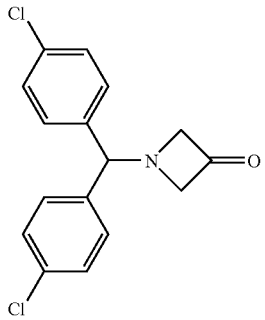

1-[Bis(4-chlorophenyl)methyl]azetidin-3-one

Step 1: Azetidin-3-ol

A mixture of 15 g (62.76 mmol) of 1-benzhydrylazetan-3-ol (1) and 3.5 g of palladium on activated carbon (10%) in 130 mL of methanol was pressurized to 50 psi with hydrogen gas and shaken at room temperature for 48 h. After removal of catalyst, the solution was concentrated to remove methanol. The residue was washed with hexanes/ether (1/1) to afford the title compound; ¹NMR(CD₃OD) δ 2.09 (s, 1H), 3.94 (m, 2H), 4.28 (m, 21H), 4.75 (m, 1H).

Step 2: 1-[Bromo(4-chlorophenyl)methyl]-4-chlorobenzene

To a solution of 15.14 g (59.3 mmol) of bis(4-chlorophenyl)methanol in 100 mL of methylene chloride was added slowly a solution of 71.2 mL of BBr₃ (71.2 mmol, 1M in CH₂Cl₂). The solution was stirred for at 0° C. for 1 h. Then 60 mL of water was added to quench the reaction and the reaction mixture was poured into 200 mL of methylene chloride. The water layer was extracted with methylene chloride (60 mL×2) and the combined organic layer was dried over Na₂SO₄ and concentrated to give the title compound; ¹NMR (CDCl₃) δ 6.24 (s, 1H), 7.36 (d, 4H, J=8.7 Hz), 7.41 (d, 2H, J=8.7 Hz).

Step 3: 1-[Bis(4-chlorophenyl)methyl]azetidin-3-ol

The reaction mixture of 22.30 g (70.5 mmol) of 1-[bromo(4-chlorophenyl)methyl]-4-chlorobenzene, 5.67 g (77.6 mmol) of azetidin-3-ol (2) and 18.4 mL (105.75 mmol) of N,N-diisopropylethylamine in 250 mL of acetonitrile was rapidly stirred for 1.5 h at rt to 91° C. Reaction mixture was concentrated to remove solvents and residue was purified by silica gel chromatography with hexanes/ethyl acetate/ammonia (2M in MeOH)=100/30/0.5 to afford the title compound; ¹NMR(CDCl₃) δ 2.03 (br s, 1H), 2.81 (m, 2H), 3.55 (m, 2H), 4.34 (s, 1H), 4.50 (m, 1H), 7.29 (m, 4H), 7.34 (m, 4H).

Step 4: 1-[Bis(4-chlorophenyl)methyl]azetidin-3-one

To a solution of 6.3 mL (71.42 mmol) of oxalyl chloride in 250 mL of methylene chloride was added slowly 10.15 mL (142.84 mmol) of DMSO at −78° C. and stirred for 20 minutes. To this was added a solution of 11 g (35.7 mmol) of 1-[bis(4-chlorophenyl)methyl]azetidin-3-ol in 30 mL of methylene chloride and the mixture was stirred for 30 minutes at −78° C. Then 24.7 mL (178.56 mmol) of triethylamine was added at −78° C. and the mixture was stirred for 1 h at −78° C. before warming to rt. The solution was poured into 500 mL of ether and washed with 50 mL of aq NaHCO₃. The organic layer was dried over Na₂SO₄ and concentrated to afford the title compound.

PREPARATION 2

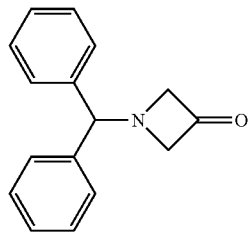

1-[bis(4-phenyl)methyl]azetidin-3-one

Prepared from 1-[Bis-phenylmethyl]azetidin-3-ol as described in Step 5 of Preparation 1; Mass Spectrum: m/e=238 (M+1).

PREPARATION 3

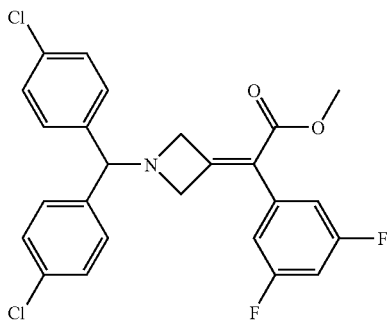

Methyl {1-[bis(4-chlorophenyl)methyl]azetidin-3-ylidene}(3,5-difluorophenyl)acetate Step 1: Methyl (3,5-difluorophenyl)acetate A solution of 5.0 g (29.1 mmol) of 3,5-difluorophenylacetic acid and a solution of 20 mL (80 mmol) of HCl in dioxane (4M) in 60 mL of methanol was heated at reflux for 6 h. After cooling, the solution was concentrated and the residue poured into 200 mL of ether/ethyl acetate (1/1). The organic layer was washed with 20 mL of water, dried over Na₂SO₄ and concentrated to afford the title compound.

Step 2: Methyl {1-[bis(4-chlorophenyl)methyl]-3-hydroxyazetidin-3-yl}(3,5-difluorophenyl)acetate A solution of 2 mL of 1.6M butyllithium in hexane and 2 mL of dry THF was cooled to −78° C. under nitrogen. To this was added a solution of 0.626 g (3.2 mmol) of methyl (3,5-difluorophenyl)acetate in 4 mL of THF and the solution was stirred at −78° C. After 20 min, a solution of 0.600 g (1.95 mmol) of 1-[bis(4-chlorophenyl)methyl]azetidin-3-one in 4 mL THF was added and the solution was stirred at −78° C. After 1 h, the reaction was quenched by addition of 10 mL of saturated NH₄Cl solution and 20 mL of ether. The layers were separated and the aqueous layer was washed with ether. The combined organic layers were washed with brine, dried over magnesium sulfate and concentrated. The residue was filtered through a plug of silica gel using 25% ether-hexane to afford the title compound; ¹NMR(CDCl₃) δ 2.91 (d, 1H J=8.3 Hz), 3.14 (d, 1H J=8.0 Hz), 3.17 (d, 2H, J=8.2 Hz), 3.32 (d, 1H J=7.8 Hz), 3.74 (s, 3H), 4.03 (s, br, 1H), 4.42 (s, 1H), 4.42 (s, 1H), 6.76 (m, 1H), 6.6.89 (m, 2H), 7.33 (m, 4H), 7.38 (m, 4H); Mass Spectrum: m/e=492 (M+1 ³⁵Cl, ³⁵Cl ) and 494 (M+1 ³⁵Cl, ³⁷Cl).

Step 3: Methyl {1-[bis(4-chlorophenyl)methyl]azetidin-3-ylidene}(3,5-difluorophenyl)acetate A solution of 0.71 g (1.44 mmol) of methyl{1-[bis(4-chlorophenyl)methyl]-3-hydroxyazetidin-3-yl}(3,5-difluorophenyl)acetate, 0.295 g (1.73 mmol) of methanesulfonyl anhydride, and 0.400 mL pyridine in 5 mL of dichloromethane was stirred at room temperature overnight. To this was added 0.400 mL of diazabicycloundecane and the solution remained stirring at room temperature. The mixture was partitioned between ether and water and the aqueous layer was washed with 20 mL of ether. The organic layers were washed with brine, combined, dried over MgSO₄ and concentrated. The residue was filtered through a pad of silica gel using 20% ether-hexane to afford the title compound; ¹NMR(CDCl₃) δ 3.67 (s, 3H), 3.84 (m, 2H), 4.25 (m, 2H), 4.54 (s, 1H), 6.76 (m, 1H), 6.78 (m, 2H), 7.33 (m, 4H), 7.38 (m, 4H); Mass Spectrum: m/e=474 (M+1 ³⁵Cl, ³⁵Cl) and 476 (M+1 ³⁵Cl, ³⁷Cl).

PREPARATION 4

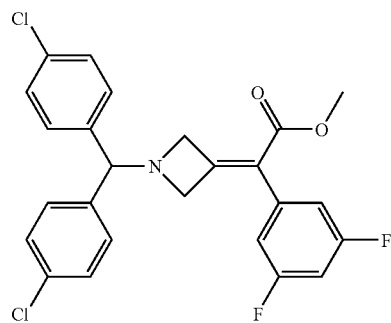

Methyl {1-[bis(4-chlorophenyl)methyl]azetidin-3-ylidene}(3,5-difluorophenyl)acetate To a solution of 3.83 g (20.57 mmol) of methyl(3,5-difluorophenyl)acetate in 30 mL of THF was added a solution of 8.6 mL (21.51 mmol) of butyllithium (2.5M solution in hexanes) and stirred for 30 minutes at −78° C. A solution of 5.73 g (18.7 mmol) of 1-[bis(4-chlorophenyl)methyl]azetidin-3-one (7) in 10 mL THF was added and the solution was stirred for 2 h at −78° C. Then 2.28 g (18.6 mmol) of 4-dimethylaminopyridine, 3.3 mL(18.7 mmol) of N,N-diisopropylethylamine and 3.0 mL (37.4 mmol) of methanesulfonyl chloride was added and the solution was stirred for 1 h as it warmed from −78° C. to rt. The reaction mixture was then warmed to 45° C. and stirred for additional 2.5 h. The mixture was poured into 250 mL of ether and washed with 50 mL of aq NaHCO₃. The organic layer was dried over Na₂SO₄ and concentrated. The residue was purified by silica gel chromatography with hexanes/ethyl acetate=15:1 to afford the title compound; ¹NMR (CDCl₃) δ 3.67 (s, 3H), 3.84 (m, 2H), 4.25 (m, 2H), 4.54 (s, 1H), 6.76 (m, 1H), 6.78 (m, 2H), 7.33 (m, 3H), 7.38 (m, 2H); Mass Spectrum: m/e=474 (M+1 ³⁵Cl, ³⁵Cl) and 476 (M+1 ³⁵Cl, ³⁷Cl).

PREPARATION 5

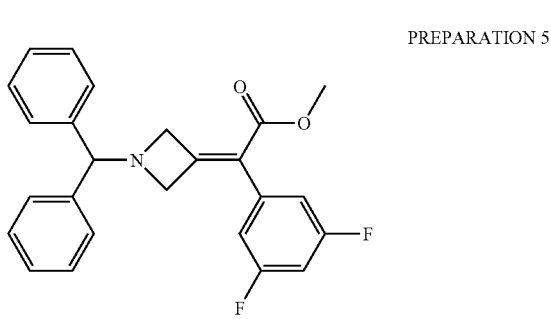

Methyl (3,5-difluorophenyl)[1-(diphenylmethyl)azetidin-3-ylidene]acetate

Prepared from 1-[bis(4-phenyl)methyl]azetidin-3-one (Preparation 2) by procedures described in Steps 1-3 of Preparation 3; Mass Spectrum: m/e=406 (M+1).

PREPARATION 6

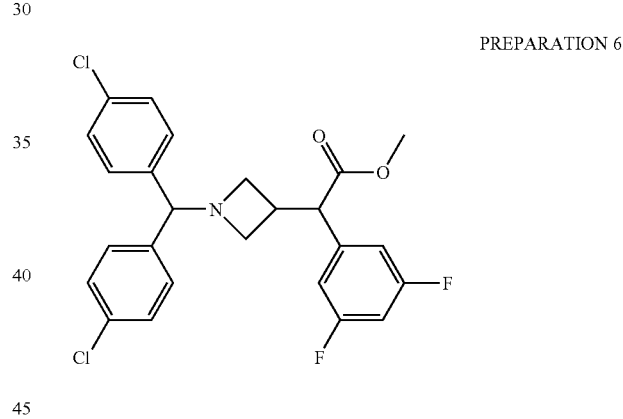

Methyl{1-[bis(4-chlorophenyl)methyl]azetidin-3-yl}(3,5-difluorophenyl)acetate

To a solution of 5.0 g (10.54 mmol) of methyl{1-[bis(4-chlorophenyl)methyl]azetidin-3-ylidene}(3,5-difluorophenyl)acetate in 60 mL of MeOH and 15 mL of CH₂Cl₂ was slowly added 798 mg (21.08 mmol) of NaBH₄. The solution was stirred for 5 h at 0° C., then poured into 250 mL of ether and washed with 50 mL of aq NaHCO₃. The organic layer was dried over Na₂SO₄ and concentrated. The residue was purified by silica gel chromatography with hexanes/ethyl acetate to afford the title compound; ¹NMR(CDCl₃) δ 2.68 (m, 1H), 2.92 (m, 1H), 3.10-3.15 (m, 2H), 3.44 (m, 1H)3.69 (s, 3H), 3.86 (d, J=11 Hz, 1H), 4.30 (s, 1H), 6.74 (m, 1H), 6.85 (m, 2H), 7.24-7.34 (m, 8H); Mass Spectrum: m/e=476 (M+1 ³⁵Cl, ³⁵Cl) and 478 (M+1 ³⁵Cl, ³⁷Cl).

PREPARATION 7

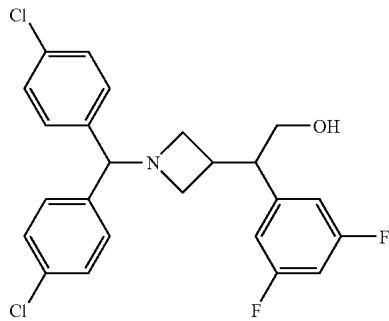

2-{1-[Bis(4-chlorophenyl)methyl]azetidin-3-yl}(3,5-difluorophenyl)ethanol

To a solution of 1.47 g (3.09 mmol) of methyl{1-[bis(4-chlorophenyl)methyl]azetidin-3-yl}(3,5-difluorophenyl)acetate in 25 mL THF was added a solution of 3.1 mL (3.1 mmol) of LiAlH$_4$ (1M solution in THF). The solution was stirred for 10 minutes at 0° C. Then 4 g of sodium sulfate decahydrate was added to quench the reaction and the mixture was stirred for 1 h at rt. The mixture was filtered and the organic layer was dried over Na$_2$SO$_4$ and concentrated to afford the title compound; $^1$NMR(CDCl$_3$) δ 3.99 (s, 2H), 4.03 (s, 2H), 4.35 (s, 2H), 4.54 (s, 1H), 6.70-6.80 (m, 3H), 7.30-7.40 (m, 8H); Mass Spectrum: m/e=446 (M+1 $^{35}$Cl, $^{35}$Cl) and 448 (M+1 $^{35}$Cl, $^{37}$Cl).

PREPARATION 8

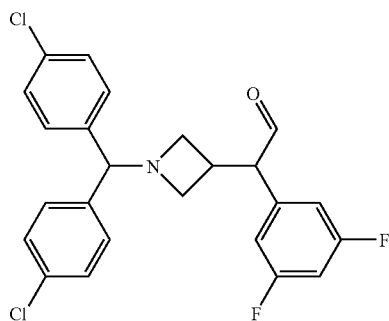

{1-[Bis(4-chlorophenyl)methyl]azetidin-3-yl}(3,5-difluorophenyl)acetaldehyde

To a solution of 0.92 mL (10.5 mmol) of oxalyl chloride in 60 mL of methylene chloride was added slowly 1.49 mL (20.96 mmol) of DMSO at −78° C. and stirred for 20 minutes. Then a solution of 2.35 g (5.24 mmol) of 2-{1-[bis(4-chlorophenyl)methyl]azetidin-3-yl}(3,5-difluorophenyl)ethanol in 10 mL of methylene chloride was added into above reaction mixture. The reaction mixture was stirred for 30 minutes at −78° C. Then 3.62 mL (26.2 mmol) of triethylamine was added at −78° C. and the mixture was stirred for 1 h at −78° C. to rt. This was poured into 200 mL of ether and washed with 30 mL of aq NaHCO$_3$. The organic layer was dried over Na$_2$SO$_4$ and concentrated to afford the title compound. $^1$NMR(CDCl$_3$) δ 2.74 (m, 1H), 2.94 (m, 1H), 3.01 (m, 1H), 3.19 (m, 1H), 3.48 (m, 1H), 3.58 (d, J=10 Hz, 1H), 4.29 (s, 1H), 6.71-6.85 (m, 3H), 7.24-7.33 (m, 8H), 9.66 (s, 1H); Mass Spectrum: m/e=446 (M+1 $^{35}$Cl, $^{35}$Cl) and 448 (M+1 $^{35}$Cl, $^{37}$Cl).

PREPARATION 9

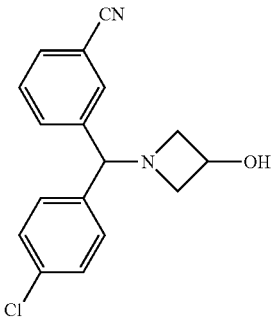

3-[(S)-(4-Chlorophenyl)(3-hydroxyazetidin-1-yl)methyl]benzonitrile

Step 1 N-[(1E)-3-cyanophenyl)methylene]-2-methylpropane-2-(R)sulfinamide

A solution of 19.0 g (157 mmole) of (R)-(+)-2-methylpropane-2-sulfinamide and 89.0 g (314 mmole) of titanium tetraisopropoxide in CH$_2$Cl$_2$ was stirred at room temperature for 10 min. Then a solution of 21.6 g (165 mmole) of 3-formylbenzonitrile in 10 mL CH$_2$Cl$_2$ was added, and the solution was stirred at room temperature. After 18 h, the reaction was quenched by the addition of 30 mL brine and the solution was rapidly stirred for 15 min. The mixture was filtered through a pad of CELITE and the residue was washed with 300 mL of CH$_2$Cl$_2$. The combined organic extracts were washed with brine, dried over Na$_2$SO$_4$ and concentrated. The residue was filtered through a pad of silica gel using 20% ethyl acetate-hexane to afford the title compound; $^1$H-NMR(CDCl$_3$) δ 1.31 (s, 9H), 7.65 (t, 1H, J=7.8 Hz), 7.82 (d, 1H, J=7.8 Hz), 8.07 (d, 1H, J=7.8 Hz), 8.20 (s, 1H), 8.62 (s, 1H); Mass Spectrum: m/e=235 (M+1).

Step 2 N-[(S)-(4-chlorophenyl)(3-cyanophenyl)methyl]-2-methylpropane-2-(R)-sulfinamide A solution of 20 g (85.4 mmole) of N-[(1E)-(3-cyanophenyl)methylene]-2-methylpropane-2-(R)sulfonamide in 1000 mL toluene and 400 mL ether was cooled to −60° C. in a dry ice-acetone bath. Then 170 mL of a 1M solution of 4-chlorophenylmagnesium bromide in ether was added at a rate such that the temperature remained between −60° C. and −50° C. and the reaction was stirred at −60° C. for 6 h. The reaction was quenched by addition of 300 mL of saturated NH$_4$Cl solution and the layers were separated. The organic layer was washed with 300 mL aliquots of saturated NH$_4$Cl solution and brine, then was dried over Na$_2$SO$_4$ and concentrated. The residue was filtered through a pad of silica gel using 10 to 30% ethyl acetate hexane to afford the title compound with de>96% as determined by analytical ChiralPak AD column; $^1$H-NMR(CDCl$_3$) δ 1.27 (s, 9H), 3.76 (s, 1H), 5.65 (d, 1H, J=2.3 Hz), 7.24-7.7 (m, 8H).

Step 3
3-[(S)-amino(4-chlorophenylmethyl]benzonitrile

To a solution of 850 mg (2.45 mmole) of N-[(S)-(4-chlorophenyl)(3-cyanophenyl)methyl]-2-methylpropane-2-(R)-sulfinamide in 20 mL of CH$_3$OH was added 2.5 mL of 4M HCL in dioxane. The solution was stirred at room temperature for 45 min, then was diluted with 40 mL ether. The solids were collected by filtration and then were dissolved in a mixture of 40 mL ether and 25 mL of saturated Na₂CO₃ solution. The aqueous layer was washed with two 20 mL portions of 3:1 ether-CH₂Cl₂. The combined organic layers were dried over Na₂CO₃ and concentrated to afford the title compound as an oil; ¹H-NMR(CDCl₃) δ 1.6 (s, 2H, br), 5.24 (s, 1H), 7.24-7.78 (m, 8H).

Step 4 3-[(S)-[(3-chloro-2-hydroxypropyl)amino](4-chlorophenyl)methyl]benzonitrile A solution of 14.0 g (58 mmole) of 3-[(S)-amino(4-chlorophenyl)methyl]benzonitrile and 10.8 g (120 mmole) of epichlorhydrin in 200 mL of methanol was stirred in the dark for 72 hours. The solution was partitioned between CH₂Cl₂ and water and the layers were separated. The organic layer was dried over Na₂SO₄ and concentrated to afford the title compound, which was used in the next step without purification; 335 (M+1, ³⁵Cl); 337 (M+1, ³⁷Cl).

Step 5 3-[(S)-(4-chlorophenyl)(3-hydroxyazetidin-1-yl)methyl]benzonitrile

A solution of 8.0 g (24.0 mmole) of 3-[(S)-[(3-chloro-2-hydroxypropyl)amino](4-chlorophenyl)methyl]benzonitrile and 11.7 g (36 mmole) of Cs₂CO₃ in 50 mL of dry CH₃CN was divided between two 80 mL microwave tubes. The tubes were irradiated in a microwave oven (with cooling) at 160° C. for 8 h. The samples were filtered and the solids were washed with 20 mL of CH₃CN and then 20 mL of CH₂Cl₂. The combined filtrates were concentrated and the residue was portioned between 300 mL ethyl acetate and 100 mL water. The layers were separated and the aqueous layer was washed with 100 mL ethyl acetate. The combined organic extracts were washed with brine, dried over Na₂SO₄ and concentrated. The residue was purified by flash chromatography using 10-20% ethyl acetate in CH₂Cl₂ to afford the title compound as a clear oil; ¹H-NMR(CDCl₃) δ 1.6 (s, 2H, br), 5.24 (s, 1H), 7.24-7.78 (m, 8H) 2.89 (m, 2H), 3.54 (m, 2H), 4.39 (s, 1H), 4.52 (m, 1H), 7.27-7.8 (m, 8H).

EXAMPLE 1

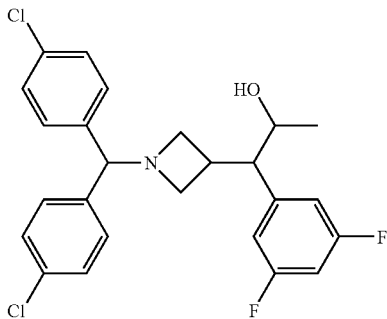

{1-[Bis(4-chlorophenyl)methyl]azetidin-3-yl}-1-(3,5-difluorophenyl)propan-2-ol

To a solution of 790 mg (1.77 mmol) of {1-[bis(4-chlorophenyl)methyl]azetidin-3-yl}(3,5-difluorophenyl)acetaldehyde in 20 mL of THF was added slowly a solution of 1.18 mL (3.54 mmol) of methylmagnesium chloride (3.0M solution in THF) at −78° C. and stirred for 1 h. The reaction mixture was warmed to 0° C. for 1 h and 3 g of sodium sulfate decahydrate was added to quench the reaction, followed by stirring for 1 h at rt. The reaction mixture was filtered and the organic layer was dried over Na₂SO₄ and concentrated. The residue was purified by silica gel chromatography with hexanes/acetone=8:1 to afford the title compound. ¹NMR (CDCl₃) δ 0.94 (d, J=6.7 Hz, 3H), 3.44 (d, J=6.5 Hz, 1H), 3.77 (m, 1H), 3.97 (s, 2H), 4.02 (s, 2H), 4.34 (m, 1H), 4.53 (s, 1H), 6.69 (m, 1H), 6.78 (m, 2H), 7.28 (d, J=8.5 Hz, 4H), 7.38 (d, J=8.5 Hz, 4H); Mass Spectrum: m/e=462 (M+1 ³⁵Cl, ³⁵Cl) and 464 (M+1 ³⁵Cl, ³⁷Cl).

EXAMPLE 2

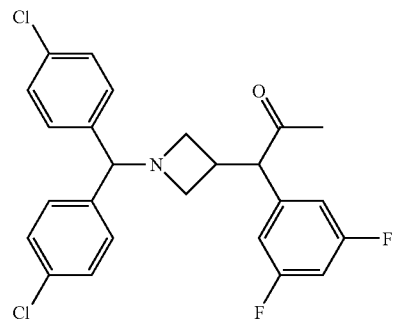

1-{1-[Bis(4-chlorophenyl)methyl]azetidin-3-yl}-1-(3,5-difluorophenyl)acetone

To a solution of 110 uL (1.26 mmol) of oxalyl chloride in 10 mL of methylene chloride was slowly added 180 uL (2.52 mmol) of DMSO at −78° C., followed by stirring for 20 minutes. Then a solution of 292 mg (0.63 mmol) of 1-{1-[bis (4-chlorophenyl)methyl]azetidin-3-yl}-1-(3,5-difluorophenyl)propan-2-ol in 2 mL of methylene chloride was added into the reaction mixture, followed by stirring for 30 minutes at −78° C. Then 435 uL (3.15 mmol) of triethylamine was added at −78° C. and the mixture was stirred for 1 h while it warmed from −78° C. to rt. The mixture was poured into 30 mL of ether and washed with 5 mL of aq NaHCO₃. The organic layer was dried over Na₂SO₄ and concentrated to afford the title compound. NMR(CDCl₃) δ 2.09 (s, 3H), 2.65 (m, 1H), 2.78 (m, 1H), 3.08 (m, 2H), 3.45 (m, 1H), 3.90 (d, J=10.5 Hz, 1H), 4.28 (s, 1H), 6.73-6.77 (m, 3H), 7.24-7.33 (m, 8H); Mass Spectrum: m/e=460 (M+1 ³⁵Cl, ³⁵Cl) and 462 (M+1 ³⁵Cl, ³⁷Cl).

EXAMPLE 3

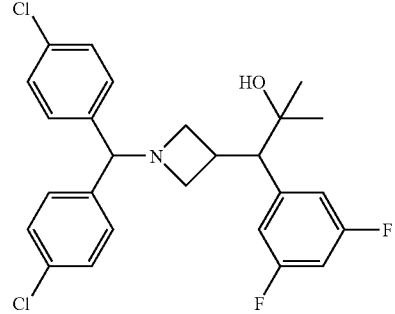

1-{1-[Bis(4-chlorophenyl)methyl]azetidin-3-yl}-1-(3,5-difluorophenyl)-2-methylpropan-2-ol To a solution of 230 mg (0.5 mmol) of 1-{1-[bis(4-chlorophenyl)methyl]azetidin-3-yl}-1-(3,5-difluorophenyl)acetone in 10 mL of THF was added slowly a solution of 0.42 mL (1.25 mmol) of methylmagnesium chloride (3.0M solution in THF) at −78° C. and stirred for 1 h. The reaction mixture was warmed to 0° C. for 1 h, followed by adding 1 g of sodium sulfate decahydrate to quench the reaction, and stirring for 1 h at rt. The quenched reaction mixture was filtered and the organic layer was dried over $Na_2SO_4$ and concentrated. The residue was purified by silica gel chromatography with hexanes/acetone=8:1 to afford racemic 1-{1-[bis(4-chlorophenyl)methyl]azetidin-3-yl}-1-(3,5-difluorophenyl)-2-methylpropan-2-ol as a white solid. The enantiomers were separated by a chiral column (OJ Column with hexanes/ethyl alcohol); $^1H$ NMR($CDCl_3$) δ 1.06 (s, 3H), 1.15 (S, 3H), 2.29 (t, 1H, J=7.5 Hz), 6.73 (m, 3H), 7.21-7.33 (m, 8H); Mass Spectrum: m/e=476 (M+1 $^{35}Cl, ^{35}Cl$) and 478 (M+1 $^{35}Cl, ^{37}Cl$).

EXAMPLES 4-7

The following compounds were prepared using the procedures described in Preparations 4, 6-8 and Examples 1-3, starting with the appropriately substituted aryl or heteroaryl acetate.

EXAMPLE 8

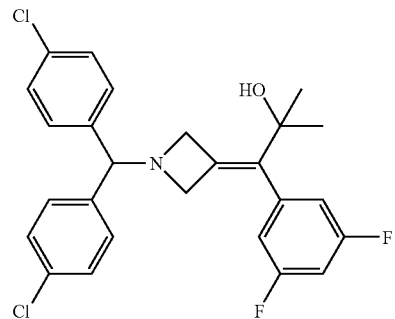

1-{1-[Bis(4-chlorophenyl)methyl]azetidin-3-ylidene}-1-(3,5-difluorophenyl)-2-methylpropan-2-ol A solution of 1.15 g (2.43 mmol) of methyl{1-[bis(4-chlorophenyl)methyl]azetidin-3-ylidene}(3,5-difluorophenyl)acetate (Preparation 5) in 10 mL of dry ethyl ether was cooled to −78° C. under nitrogen. Dropwise, 3.1 mL of a 1M solution of methyllithium in ether was added. After 30 minutes, another 3.1 mL of the 1M solution of methyllithium in ether

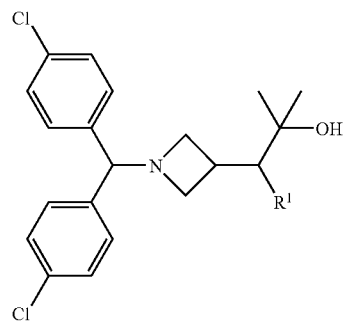

| Example | Name | $R^1$ | Mass Spectrum m/e |
|---|---|---|---|
| 4 | 1-{1-[Bis(4-chlorophenyl)methyl]azetidin-3-yl}-1-(3-fluorophenyl)-2-meethylpropan-2-ol | 3-fluorophenyl | 458 (M+1 $^{35}Cl, ^{35}Cl$); 460 (M+1 $^{35}Cl, ^{37}Cl$) |
| 5 | 1-{1-[Bis(4-chlorophenyl)methyl]azetidin-3-yl}-1-(3-chlorophenyl)-2-methylpropan-2-ol | 3-chlorophenyl | 474 (M+1 $^{335}Cl, ^{35}Cl$); 476 (M+1 $^{35}Cl, ^{37}Cl$) |
| 6 | 1-{1-[Bis(4-chlorophenyl)methyl]azetidin-3-yl}-2-methyl-1-[4-(methylsulfonyl)phenyl]propan-2-ol | 4-($SO_2Me$)phenyl | 518 (M+1 $^{35}Cl, ^{35}Cl$); 520 (M+1 $^{35}Cl, ^{37}$) |
| 7 | 1-{1-[Bis(4-chlorophenyl)methyl]azetidin-3-yl}-2-methyl-1-pyridin-3-ylpropan-2-ol | pyridin-3-yl | 441 (M+1 $^{35}Cl, ^{35}Cl$); 443 (M+1 $^{35}Cl, ^{37}Cl$) | was added dropwise and the solution was stirred at −78° C. for 30 min. The reaction was quenched by addition of water and the mixture was partitioned between ether and water. The aqueous extract was washed with ether and the combined organic layers were washed with brine, dried over Na$_2$SO4, and concentrated. The residue was purified by chromatography on a Waters RCM column (5 micron silica gel, 20 mm×10 cm) using a 2:1 mixture of hexane and 5:4:1 hexane-methyl tert-butyl ether-acetonitrile. Homogenous fractions were pooled and concentrated to afford the title compound; $^1$NMR (CDCl$_3$) δ 1.35 (s, 3H), 3.49 (m, 2H), 4.09 (m, 2H), 4.46 (s, 1H), 6.68 (m, 1H), 6.70 (m, 1H), 7.26 (m, 4H), 7.34 (m, 4H); Mass Spectrum: m/e=474 (M+1 $^{35}$Cl, $^{35}$Cl) and 475 (M+1 $^{35}$Cl, $^{37}$Cl).

EXAMPLE 9

Starting with {1-[bis(4-chlorophenyl)methyl]azetidin-3-ylidine}(3-fluorophenyl)acetate (as in Preparation 4) by the method of Example 8, the following were prepared

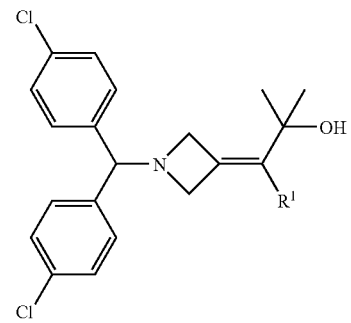

| Example | Name | R$^1$ | Mass Spectrum m/e |
|---|---|---|---|
| 9 | 1-{1-[Bis(4-chlorophenyl)methyl]azetidin-3-ylidene}-1-(3-fluorophenyl)-2-methylpropan-2-ol | 3-fluorophenyl | 456 (M+1 $^{35}$Cl, $^{35}$Cl); 458 (M+1 $^{35}$Cl, $^{37}$Cl) |
| 10 | 1-{1-[Bis(4-chlorophenyl)methyl]azetidin-3-ylidene}-1-(3-chlorophenyl)-2-methylpropan-2-ol | 3-chlorophenyl | 472 (M+1 $^{35}$Cl, $^{35}$Cl); 474 (M+1 $^{35}$Cl, $^{37}$Cl) |
| 11 | 1-{1-[Bis(4-chlorophenyl)methyl]azetidin-3-ylidene}-1-(4-fluorophenyl)-2-methylpropan-2-ol | 4-fluorophenyl | 456 (M+1 $^{35}$Cl, $^{35}$Cl); 458 (M+1 $^{35}$Cl, $^{37}$Cl) |
| 12 | 1-{1-[Bis(4-chlorophenyl)methyl]azetidin-3-ylidene}-2-methyl-1-pyridin-3-ylpropan-2-ol | pyridin-3-yl | 439 (M+1 $^{35}$Cl, $^{35}$Cl); 441 (M+1 $^{35}$Cl, $^{37}$Cl) |
| 13 | 1-{1-[Bis(4-chlorophenyl)methyl]azetidin-3-ylidene}-2-methyl-1-thien-3-ylpropan-2-ol | thien-3-yl | 444 (M+1 $^{35}$Cl, $^{35}$Cl); 446 (M+1 $^{35}$Cl, $^{37}$Cl) |
| 14 | 1-{1-[Bis(4-chlorophenyl)methyl]azetidin-3-ylidene}-2-methyl-1-thien-2-ylpropan-2-ol | thien-2-yl | 444 (M+1 $^{35}$Cl, $^{35}$Cl); 446 (M+1 $^{35}$Cl, $^{37}$Cl) |
| 15 | 1-{1-[bis(4-chlorophenyl)methyl]azetidin-3-ylidene}-2-methyl-1-(1-methyl-1H-imidazol-4-ylpropan-2-ol | 1-methyl-1H-imidazol-4-yl | 442 (M+1 $^{35}$Cl, $^{35}$Cl); 444 (M+1 $^{35}$Cl, $^{37}$Cl) |

-continued

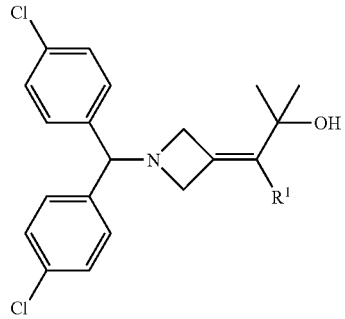

| Example | Name | R[1] | Mass Spectrum m/e |
|---|---|---|---|
| 16 | 1-{1-[Bis(4-chlorophenyl)methyl]azetidin-3-ylidene}-2-methyl-1-[3-(trifluoromethyl)phenyl]propan-2-ol | 3-CF$_3$-C$_6$H$_4$- | 506 (M+1 $^{35}$Cl, $^{35}$Cl); 508 (M+1 $^{35}$Cl, $^{37}$Cl) |
| 17 | 3-(1-{1-[Bis(4-chlorophenyl)methyl]azetidin-3-ylidene}-2-hydroxy-2-methylpropyl)benzonitrile | 3-CN-C$_6$H$_4$- | 463 (M+1 $^{35}$Cl, $^{35}$Cl); 465 (M+1 $^{35}$Cl, $^{37}$Cl) |
| 18 | 5-(1-{1-[bis(4-chlorophenyl)methyl]azetidin-3-ylidene}-2-hydroxy-2-methylpropyl)nicotinonitrile | 5-CN-pyridin-3-yl | 464 (M+1 $^{35}$Cl, $^{35}$Cl); 466 (M+1 $^{35}$Cl, $^{37}$Cl) |

EXAMPLE 19

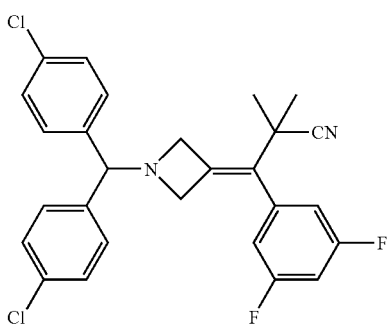

3-{1-[Bis(4-chlorophenyl)methyl]azetidin-3-ylidene}-3-(3,5-difluorophenyl)-2,2-dimethylpropanenitrile

Step 1: Tert-butyl 3-{[methoxy(methyl)amino]carbonyl}azetidine-1-carboxylate To a solution of 980 mg (4.87 mmol) of boc-azetidine-3-carboxylic acid, 951 mg (9.75 mmol) of N,O-dimethylhydroxylamine hydrochloride, 329 mg (2.435 mmol) of HOBT and 1.87 g (9.75 mmol) of 1-[3-dimethylamino)propyl]-3-ethylcarbodiimide hydrochloride in 30 mL of CH$_2$Cl$_2$ was added 2.54 mL 44.61 mmol) of N,N-diisopropylethylamine at 0° C. and it was stirred for 6 h at rt. Then the reaction mixture was poured into 100 mL of ether and washed with 20 mL of aq NaHCO$_3$. The organic layer was dried over Na$_2$SO$_4$ and concentrated to afford the title compound. $^1$NMR (CDCl$_3$) δ 1.46 (s, 9H), 3.23 (s, 3H), 3.62 (m, 1H), 3.68 (s, 3H), 4.07 (m, 2H), 4.09 (m, 2H).

Step 2: Tert-butyl 3-(3,5-difluorobenzoyl)azetidine-1-carboxylate

A solution of 1.19 g (4.87 mmol) of tert-butyl 3-{[methoxy(methyl)amino]carbonyl}azetidine-1-carboxylate in 15 mL of THF was added to a solution of 14.6 mL (7.31 mmol) of 3,5-difluorophenylmagnesium bromide (0.5M in THF). The reaction mixture was stirred for 2 h at 0° C., then poured into 100 mL of ether and washed with 10 mL of water. The organic layer was dried over Na$_2$SO$_4$ and concentrated. The residue was purified by silica gel chromatography with hexanes/ethyl acetate to afford the title compound. $^1$NMR(CDCl$_3$) δ 1.48 (s, 9H), 4.08 (m, 1H), 4.24 (m, 4H), 7.36 (m, 1H), 7.38 (m, 2H).

Step 3: Azetidin-3-yl(3,5-difluorophenyl)methanone

A solution of 400 mg (1.35 mmol) of tert-butyl 3-(3,5-fluorobenzoyl)azetidine-1-carboxylate in 6 mL of HCl in dioxane (4M) and 2.5 mL of TFA was stirred for 4 h at 50° C. The reaction mixture was concentrated, and the residue was washed with hexanes/ether (1/1) to afford the title compound. Mass Spectrum: m/e=199 (M+1).

Step 4: {1-[bis(4-chlorophenyl)methyl]azetidin-3-yl}(3,5-difluorophenyl)methanone The reaction mixture of 377 mg (1.19 mmol) of 1-[bromo(4-chlorophenyl)methyl]-4-chlorobenzene (Preparation 1, Step 2), 280 mg (1.19 mmol) of azetidin-3-yl(3,5-difluorophenyl)methanone and 0.49 mL (2.83 mmol) of N,N-diisopropylethylamine in 8 mL of acetonitrile was rapidly stirred for 1.5 h at rt to 91° C. Reaction mixture was concentrated to remove solvents and residue was purified by silica gel chromatography with hexanes/ethyl acetate=9/1 to afford the title compound. $^1$NMR(CDCl$_3$) δ 3.37 (s, 2H), 3.58 (s, 2H), 4.05 (m, 1H), 4.38 (s, 1H), 7.02 (m, 1H), 7.28-7.34 (m, 10H). Mass Spectrum: m/e=432 (M+1 $^{35}$Cl, $^{35}$Cl) and 435 (M+1 $^{35}$Cl, $^{37}$Cl).

Step 5: 3-{1-[Bis(4-chlorophenyl)methyl]azetidin-3-yl}-3-(3,5-difluorophenyl)-3-hydroxy-2,2-dimethylpropanenitrile To a solution of 84 uL (0.928 mmol) of isobutyronitrile in 2 mL of THF was added a solution of 370 uL (0.928 mmol) of butyllithium (2.5M solution in hexanes), followed by stirring for 50 minutes at −55° C. to −40° C. Then a solution of 334 mg (0.773 mmol) of {1-[bis(4-chlorophenyl)methyl]azetidin-3-yl}(3,5-difluorophenyl)methanone (as in Preparation 6) in THF was added at −78° C. and the solution was stirred for 5 h at −60° C. to −50° C. A solution of 2 mL of saturated NH$_4$Cl was added to quench the reaction and the reaction mixture was poured into 30 mL of ether and washed with 5 mL of aq NaHCO$_3$. The organic layer was dried over Na$_2$SO$_4$ and concentrated. The residue was purified by silica gel chromatography with hexanes/ethyl acetate=4:1 to afford the title compound. $^1$NMR(CDCl$_3$) δ 1.24 (s, 3H), 1.34 (S, 3H), 2.58 (br, 1H), 3.12 (br, 1H), 3.40 (br, 2H), 3.60 (br, 1H), 4.26 (m, 1h) 4.43 (s, 1H), 6.76 (m, 1H), 7.06 (m, 2H), 7.25-7.34 (m, 8H); Mass Spectrum: m/e=501 (M+1 $^{35}$Cl, $^{38}$Cl) and 503 (M+1 $^{35}$Cl, $^{37}$Cl).

Step 6: 3-{1-[Bis(4-chlorophenyl)methyl]azetidin-3-ylidene}-3-(3,5-difluorophenyl)-2,2-dimethylpropanenitrile The reaction mixture of 128 mg (0.255 mmol) of 3-{1-[bis(4-chlorophenyl)methyl]azetidin-3-yl}-3-(3,5-difluorophenyl)-3-hydroxy-2,2-dimethylpropanenitrile and 3 mL of phosphorus oxychloride in 5 mL of pyridine was heated at reflux for 48 h. The solution was concentrated, poured into 30 mL of ether, and washed with 5 mL of aq NaHCO$_3$. The organic layer was dried over Na$_2$SO$_4$ and concentrated. The residue was purified by silica gel chromatography with hexanes/ethyl acetate=4:1 to afford the title compound. 1NMR(CDCl$_3$) δ 1.47 (s, 6H), 3.48 (s, 2H), 4.18 (s, 2H), 4.47 (s, 1H), 6.66-6.77 (m, 2H), 7.25-6-7.35 (m, 8H); Mass Spectrum: m/e=483 (M+1 $^{35}$Cl, $^{35}$Cl) and 485 (M+1 $^{35}$Cl, $^{37}$Cl).

EXAMPLE 20

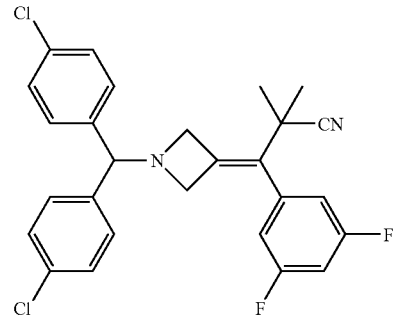

3-{1-[bis(4-chlorophenyl)methyl]azetidin-3-ylidene}-3-(3,5-difluorophenyl)-2,2-dimethylpropanenitrile

Step 1: 2-{1-[Bis(4-chlorophenyl)methyl]azetidin-3-ylidene}-2-(3,5-difluorophenyl)ethanol To a solution of 2.11 g (4.45 mmol) of methyl{1-[bis(4-chlorophenyl)methyl]azetidin-3-ylidene}(3,5-difluorophenyl)acetate in 40 mL of hexanes and 40 mL of CH$_2$Cl$_2$ was added a solution of 26.7 mL (26.7 mmol) of DIBAL-H (1M solution in THF), followed by stirring for 1 h at −78° C. The reaction mixture was warmed to rt for 1.5 h, quenched by addition of 8 g of sodium sulfate decahydrate, and stirred for 1 h at rt. The quenched reaction was filtered and the organic layer was concentrated. The residue was purified by silica gel chromatography with hexanes/ethyl acetate to afford the title compound as a white solid. $^1$NMR(CDCl$_3$) δ 3.99 (s, 2H), 4.03 (s, 2H), 4.35 (s, 2H), 4.54 (s, 1H), 6.70-6.80 (m, 3H), 7.30-6-7.40 (m, 8H); Mass Spectrum: m/e=446 (M+1 $^{35}$Cl, $^{35}$Cl) and 448 (M+1 $^{35}$Cl, $^{37}$Cl).

Step 2: 3-{1-[bis(4-chlorophenyl)methyl]azetidin-3-ylidene}-3-(3,5-difluorophenyl)propanenitrile The reaction mixture of 51 mg (0.114 mmol) of 2-{1-[bis(4-chlorophenyl)methyl]azetidin-3-ylidene}-2-(3,5-difluorophenyl)ethanol, 24 mg (0.137 mmol) of methanesulfonic anhydride, 14 mg (0.285 mmol) of sodium cyanide and 11 uL (0.137 mmol) pyridine in 5 mL of acetonitrile was stirred for 12 h at rt, and then concentrated. The residue was purified by silica gel chromatography with hexanes/ethyl acetate to the title compound; $^1$NMR(CDCl$_3$) δ 3.29 (s, 2H), 3.96 (s, 2H), 4.01 (s, 2H), 4.54 (s, 1H), 6.69-6.75 (m, 3H), 7.29-6-7.7.38 (m, 8H); Mass Spectrum: m/e=455 (M+1 $^{35}$Cl, $^{35}$Cl) and 457 (M+1 $^{35}$Cl, $^{37}$Cl).

Step 3: 3-{1-[bis(4-chlorophenyl)methyl]azetidin-3-ylidene}-3-(3,5-difluorophenyl)-2,2-dimethylpropanenitrile To a solution of 62 mg (0.136 mmol) of 3-{1-[bis(4-chlorophenyl)methyl]azetidin-3-ylidene}-3-(3,5-difluorophenyl)propanenitrile in 5 mL of THF was added a solution of 0.41 mL (0.41 mmol) of lithium bis(trimethylsilyl)amide (1M solution in THF) and it was stirred for 20 min. at −78° C.

Then 30 uL (0.476 mmol) of iodomethane was added and it was stirred for additional 2 h at −78° C. The reaction mixture was quenched by adding 1 mL of water and then the reaction mixture was poured into 30 mL of ether and washed with 5 mL of aq NaHCO$_3$. The organic layer was dried over Na$_2$SO$_4$ and concentrated. The residue was purified by silica gel chromatography with hexanes/ethyl acetate=4:1 to afford the title compound; $^1$NMR(CDCl$_3$) δ 1.47 (s, 6H), 3.48 (s, 2H), 4.18 (s, 2H), 4.47 (s, 1H), 6.66-6.77 (m, 2H), 7.25-6-7.35 (m, 8H); Mass Spectrum: m/e=483 (M+1 $^{35}$Cl, $^{35}$Cl) and 485 (M+1 $^{35}$Cl, $^{37}$Cl).

EXAMPLE 21

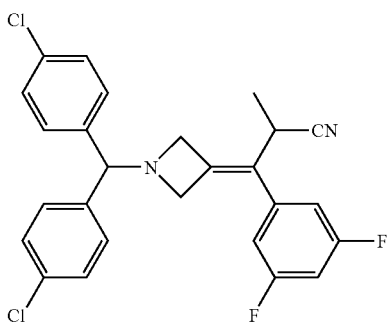

3-{1-[bis(4-chlorophenyl)methyl]azetidin-3-ylidene}-3-3,5-difluorophenyl)-2-methylpropanenitrile Further elution of the column from Example 20, Step 2 afforded the title compound; $^1$NMR(CDCl$_3$) δ 1.43 (d, 3H, J=7.3 Hz), 3.54 (q, 1H, J$_1$=15 Hz, J$_2$=7 Hz), 4.09 (m, 2H), 4.52 (s, 1H), 6.74-6.77 (m, 3H), 7.29-7.40 (m, 8H); Mass Spectrum: m/e=469 (M+1 $^{35}$Cl, $^{35}$Cl) and 471 (M+1 $^{35}$Cl, $^{37}$Cl).

EXAMPLE 22

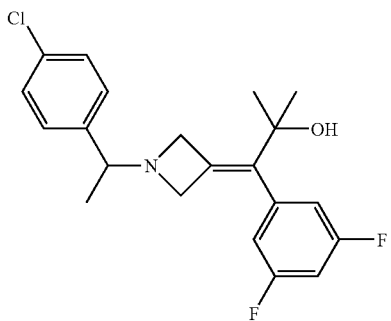

1-{1-[1-(4-chlorophenyl)ethyl]azetidin-3-ylidene}-1-(3,5-difluorophenyl)-2-methylpropan-2-ol Step 1: Methyl azetidin-3-ylidene(3,5-difluorophenyl)acetate To a solution of 0.405 g (1 mmol) of methyl (3,5-difluorophenyl)[1-(diphenylmethyl)azetidin-3-ylidene]acetate in 2 mL of dry THF was added 0.284 g (2 mmol) of 1-chloroethyl chloroformate and the solution was stirred at room temperature. After 1 h, the solution was concentrated and the residue was triturated with 2 mL of 10% ether-hexane. This was decanted and the solid residue was dissolved in methanol and heated to reflux for 6 h. The solution was concentrated to afford the title compound as the hydrochloride salt: Mass Spectrum: m/e=240 (M+1).

Step 2: Methyl {1-[1-(4-chlorophenyl)ethyl]azetidin-3-ylidene}-3-(3,5-difluorophenyl)acetate A solution of 0.142 g (0.5 mmole) of methyl azetidin-3-ylidene(3,5-difluorophenyl)acetate, 0.142 g (1 mmol) of 4-chloroacetophenone and 0.15 mL (12 mmol) of triethylamine in 5 mL of dichloroethane was stirred at room temperature. After 5 min, 0.422 g (2 mmol) of sodium triacetoxyborohydride was added and the mixture was stirred at room temperature for 3 h. The reaction was quenched by addition of saturated KHCO$_3$ solution and the mixture was partitioned between 10 mL ether and 2 mL saturated KHCO$_3$ solution. The layers were separated and the organic layer was dried over Na$_2$SO$_4$, and concentrated. The residue was purified by reverse phase chromatography (Waters Xterra C18, 19 mm×10 mm) using a gradient of CH$_3$CN—H$_2$O-Et$_3$N (20:80:0.1 to 60:40:0.1) to afford the title compound; Mass Spectrum m/e=378 (M+1 $^{35}$Cl) and 380 (M+1 $^{35}$Cl).

Step 3: 1-{1-[1-(4-chlorophenyl)ethyl]azetidin-3-ylidene}-1-3,5-difluorophenyl)-2-methylpropan-2-ol A solution of 0.02 mg (0.53 mmol) of methyl{1-[1-(4-chlorophenyl)ethyl]azetidin-3-yl}(3,5-difluorophenyl)acetate in 2 mL ether was cooled to −78° C. under nitrogen. To this was added 0.8 mL of a 1.6M solution of methyllithium in ether and the solution was stirred at −78° C. After 1 h, the solution was quenched by addition of 1 mL water and the mixture was partitioned between 10 mL ether and 2 mL water. The aqueous layer was washed two times with 10 mL ethyl acetate and the combined organic extracts were dried over Na$_2$SO$_4$ and concentrated. The residue was purified by reverse phase chromatography (Waters Xterra C18, 19 mm×10 mm) using a gradient of CH$_3$CN—H$_2$O-Et$_3$N (20:80:0.1 to 60:40:0.1). Homogenous fractions were pooled and concentrated to afford the title compound. $^1$NMR(CDCl$_3$) δ 1.23 (s, 3H), 1.35 (s, 3H), 1.36 (s, 3H), 6.64-6.74 (m, 3H), 7.24-7.32 (m, 4H); Mass Spectrum: m/e=378 (M+1 $^{35}$Cl) and 380 (M+1 $^{35}$Cl).

EXAMPLE 23

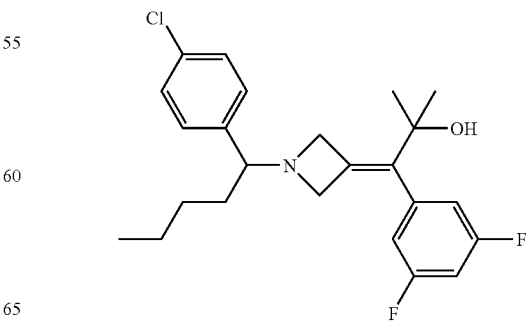

1-{1-[1-(4-chlorophenyl)pentyl]azetidin-3-ylidene}-1-1-(3,5-difluorophenyl)-2-methylpropan-2-ol Prepared from methyl azetidin-3-yl(3,5-difluorophenyl)acetate and 1-(4-chlorophenyl)pentan-1-one by the methods described in Example 22; Mass Spectrum: m/e=420 (M+1 $^{35}$Cl) and 422 (M+1 $^{37}$Cl).

EXAMPLE 24

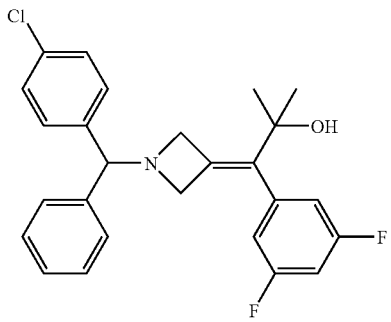

1-{1-[(4-Chlorophenyl)(phenyl)methyl]azetidin-3-ylidene}-1-(3,5-difluorophenyl)-2-methylpropan-2-ol Step 1: Methyl{1-[(4-chlorophenyl)(phenyl)methyl]azetidin-3-ylidene}(3,5-difluorophenyl)acetate A solution of 0.280 g (1 mmol) of 1-[bromo(phenyl)methyl]-4-chlorobenzene, 0.120 g (0.5 mmol) of methyl azetidin-3-yl(3,5-difluorophenyl)acetate (Example 22, Step 1) and 0.12 mL (0.7 mmol) of diisopropylethylamine in 10 mL of acetonitrile was heated at 40° C. for 18 h. The solution was concentrated and the residue was dissolved in 20 mL of ethyl acetate. This solution was washed with 10 mL water and the aqueous layer was washed with a second aliquot of 20 mL ethyl acetate. The organic extracts were washed with brine, combined, and concentrated. The residue was dissolved in acetonitrile and purified by reverse phase chromatography (Waters Xterra C18, 19 mm×50 mm) using a gradient of acetonitrile-water-triethylamine (30:70:1 to 60:40:1) to afford the title compound; $^1$NMR(CDCl$_3$) δ 3.74 (s, 3H), 3.88 (m, 2H), 4.24 (m, 2H), 4.55 (s, 1H), 6.70-6.86 (m, 3H), 7.21-7.43 (m, 9H); Mass Spectrum: m/e=440 (M+1 $^{35}$Cl) and 442 (M+1 $^{37}$Cl).

Step 2: 1-{1-[(4-Chlorophenyl)(phenyl)methyl]azetidin-3-ylidene}-1-(3,5-difluorophenyl)-2-methylpropan-2-ol A solution of 0.044 g (0.1 mmol) of methyl{1-[(4-chlorophenyl)(phenyl)methyl]azetidin-3-ylidene}(3,5-difluorophenyl)acetate in 5 mL dry ether was cooled to −78° C. under nitrogen. To this was added 0.45 mL of a 1M solution of methyllithium and the resulting solution was stirred at −78° C. for 30 minutes. A second aliquot of 0.45 mL of a 1M solution of methyllithium was added and the solution was allowed to warm to −60° C. After 1 h, the reaction was quenched by addition of 5 mL water and the layers were separated. The aqueous layer was washed with three 10 mL portions of ethyl acetate and the organic extracts were combined, dried over Na$_2$SO$_4$ and concentrated. The residue was purified by reverse phase chromatography (Waters Xterra C18, 19 mm×10 mm) using a gradient of CH$_3$CN—H$_2$O-Et$_3$N (20:80:0.1 to 60:40:0.1). Homogenous fractions were pooled and concentrated to afford the title compound; $^1$NMR (CDCl$_3$) δ 1.37 (s, 6H), 3.52 (m, 2H), 4.12 (m, 2H), 4.50 (s, 1H), 6.68-6.76 (m, 3H), 7.22-7.42 (m, 9H); Mass Spectrum: m/e=440 (M+1 $^{35}$Cl and 442 (M+1 $^{37}$Cl).

EXAMPLE 25

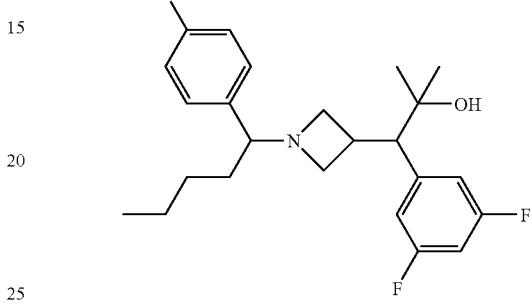

1-{1-[1-(4-chlorophenyl)pentyl]azetidin-3-yl}-1-(3,5-difluorophenyl)-2-methylpropan-2-ol Step 1: Methyl azetidin-3-yl(3,5-difluorophenyl)acetate A mixture of 0.406 g (1 mmol) of methyl (3,5-difluorophenyl)[1-(diphenylmethyl)azetidin-3-ylidene]acetate and 25 mg of 10% Pd/C in 10 mL of methanol and 1 mL of 1M HCl in ether was shaken under 40 psi H$_2$ for 18 h. The mixture was filtered through CELITE and the solid residue was washed with 30 mL of methanol. The filtrate was concentrated to afford a mixture of the title compound and diphenylmethane, which was not separated but was used directly in the next step; Mass Spectrum: m/e=242 (M+1).

Step 2: Methyl {1-[1-(4-chlorophenyl)ethyl]azetidin-3-yl}(3,5-difluorophenyl)acetate A solution of 0.015 g (0.054 mmole) of methyl azetidin-3-yl(3,5-difluorophenyl)acetate, 0.020 g (0.101 mmol) of 1-(4-chlorophenyl)pentan-1-one and 0.015 mL (0.12 mmol) of triethylamine in 5 mL of dichloroethane was stirred at room temperature. After 5 min, 0.050 g (0.237 mmol) of sodium triacetoxyborohydride was added and the mixture was stirred at room temperature for 6 h. The reaction was quenched by addition of saturated K$_2$CO$_3$ solution and the mixture was partitioned between 10 mL ether and 2 mL saturated K$_2$CO$_3$ solution. The layers were separated and the organic layer was dried over Na$_2$SO4, and concentrated. The residue was purified by reverse phase chromatography (Waters Xterra C18, 19 mm×10 mm) using a gradient of CH$_3$CN—H$_2$O-Et$_3$N (20:80:0.1 to 60:40:0.1). Homogenous fractions were pooled and concentrated to afford the title compound as a mixture of isomers; Mass Spectrum: m/e=422 (M+1 $^{35}$Cl and 424 (M+1 $^{37}$Cl). Mass Spectrum: m/e=422 (M+1 $^{35}$Cl and 424 (M+1 $^{37}$Cl).

Step 3: 1-{1-[1(4-chlorophenyl)ethyl]azetidin-3-ylidene}-1-(3,5-difluorophenyl)-2-methylpropan-2-ol A solution of 0.020 g (0.045 mmol) of methyl{1-[(4-chlorophenyl)(phenyl)methyl]azetidin-3-ylidene}(3,5-difluorophenyl)acetate in 5 mL dry ether was cooled to −78° C. under nitrogen. To this was added 0.1 mL of a 1M solution of methyllithium and the solution was stirred at −78° C. for 30 minutes. A second aliquot of 0.1 mL of a 1M solution of methyllithium was added and the solution was allowed to warm to −60° C. After 1 h, the reaction was quenched by addition of 5 mL water and the layers were separated. The aqueous layer was washed with three 10 mL portions of ethyl acetate and the organic extracts were combined, dried over $Na_2SO_4$ and concentrated. The residue was purified by reverse phase chromatography (Waters Xterra C18, 19 mm×10 mm) using a gradient of $CH_3CN$—$H_2O$-$Et_3N$ (20:80:0.1 to 60:40:0.1). Homogenous fractions were pooled and concentrated to afford the title compound; $^1NMR(CDCl_3)$ δ 0.80-0.84 (m, 3H), 0.96-1.20 (m, 2H), 1.16-1.23 (m, 2H), 1.35 (s, 3H), 1.36 (s, 3H), 1.40-1.66 (m, 2H), 3.20-3.52 (m, 2H), 3.66-3.78 (m, 1H), 3.88-4.32 (m, 2H), 6.44-6.80 (m, 3H), 7.20-7.32 (m, 2H); Mass Spectrum: m/e=422 (M+1 $^{35}Cl$ and 424 (M+1 $^{37}Cl$).

EXAMPLE 26

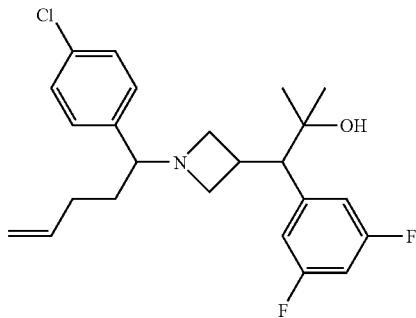

1{-1-[1-(4-chlorophenyl)pentyl]azetidin-3-ylidene}-1-(3,5-difluorophenyl)-2-methylpropan-2-ol Prepared from methyl azetidin-3-yl(3,5-difluorophenyl)acetate and 1-4-chlorophenyl)pent-4-en-1-one by the methods described in Example 25. Faster isomer: $^1NMR(CDCl_3)$ δ 1.09 (s, 3H), 1.13 (s, 3H), 1.4-1.9 (m, 4H), 2.40 (m, 1H), 2.7 (m, 2H), 3.1-3.2 (m, 2H), 3.42 (m, 2H), 4.91 (m, 2H), 5.70 (m, 1H), 6.68-6.76 (m, 3H), 7.23 (d, 2H), 7.31 (d, 2H); Mass Spectrum: m/e=420 (M+1 $^{35}Cl$ and 422 (M+1 $^{37}Cl$).

Slower isomer: $^1NMR(CDCl_3)$ δ 1.15 (s, 3H), 1.19 (s, 3H), 1.5-1.9 (m, 4H), 2.14 (m, 1H), 2.7 (m, 1H), 2.9-3.2 (m, 4H), 3.9 (m, 1H), 4.91 (m, 2H), 5.75 (m, 1H), 6.66-6.75 (m, 3H), 7.18 (d, 2H), 7.26 (d, 2H); Mass Spectrum: m/e=420 (M+1 $^{35}Cl$ and 422 (M+1 $^{37}Cl$).

EXAMPLE 27

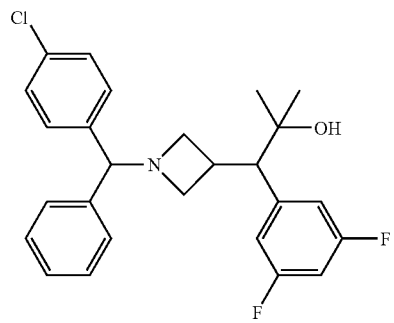

1-{1-[(4-chlorophenyl)(phenyl)methyl]azetidin-3-yl}-1-(3,5-difluorophenyl -2-methylpropan-2-ol Step 1: Methyl{1-[(4-chlorophenyl)(phenyl)methyl]azetidin-3-yl}(3,5-difluorophenyl)acetate A solution of 0.042 g (0.15 mmol) of 1-[bromo(phenyl)methyl]-4-chlorobenzene, 0.028 g (0.1 mmol) of methyl azetidin-3-yl(3,5-difluorophenyl)acetate (Example 25, Step 1) and 0.298 g (0.3 mmol) of $Cs_2CO_3$ in 5 mL of acetonitrile was heated at 45° C. for 18 h. The solution was concentrated and the residue was dissolved in 5 mL of ethyl acetate. This solution was washed with 1 mL water and the aqueous layer was washed with a second aliquot of 3 mL ethyl acetate. The organic extracts were washed with brine, combined, dried over $Na_2SO_4$ and concentrated. The residue was purified by chromatography on a Waters RCM column (5 micron silica gel, 20 mm×10 cm) using a 2:1 mixture of hexane and 5:4:1 hexane-methyl tert-butyl ether-acetonitrile. Homogenous fractions were pooled and concentrated to afford the title compound. $^1NMR(CDCl_3)$ δ 2.65-2.69 (m, 1H), 2.88-2.93 (m, 1H), 3.05-3.16 (m, 2h). 3.41-3.46 (m, 1H), 3.67 (s, 3H), 3.81-3.86 (m, 1H), 4.30 (s, 1H), 6.69-6.74 m, 1H), 6.80-6.85 (m, 2H), 7.19-7.37 (m, 9H). Mass Spectrum: m/e=442 (M+1 $^{35}Cl$) and 444 (M+1 $^{37}Cl$).

Step 2: 1-{1-[(4-Chlorophenyl)(phenyl)methyl]azetidin-3-yl}-1-3,5-difluorophenyl)-2-methylpropan-2-ol A solution of 0.044 g (0.1 mmol) of methyl{1-[(4-chlorophenyl)(phenyl)methyl]azetidin-3-yl}(3,5-difluorophenyl)acetate in 5 mL dry ether was cooled to −78° C. under nitrogen. To this was added 0.45 mL of a 1M solution of methyllithium and the solution was stirred at −78° C. for 30 minutes. A second aliquot of 0.45 mL of a 1M solution of methyllithium was added, and the solution was allowed to warm to −60° C. After 1 h, the reaction was quenched by addition of 5 mL water and the layers were separated. The aqueous layer was washed with three 10 mL portions of ethyl acetate and the organic extracts were combined, dried over $Na_2SO_4$ and concentrated. The residue was purified by reverse phase chromatography (Waters Xterra C18, 19 mm×10 mm) using a gradient of $CH_3CN$—$H_2O$-$Et_3N$ (20:80:0.1 to 60:40:0.1). Homogenous fractions were pooled and concentrated to afford the title compound; $^1NMR(CDCl_3)$ δ 1.37 (s, 6H), 3.52 (m, 2H), 4.12 (m, 2H), 4.50 (s, 1H), 6.68-6.76 (m, 3H), 7.22-7.42 (m, 9H). Mass Spectrum: m/e=440 (M+1 $^{35}Cl$) and 442 (M+1 $^{37}Cl$).

EXAMPLE 28

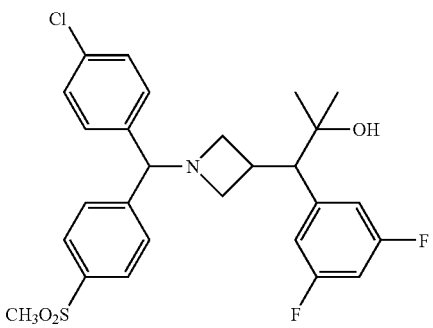

1-{1-[(4-chlorophenyl)(4-methylsulfonylphenyl)methyl]azetidin-3-yl}-1-(3,5-difluorophenyl)-2-methylpropan-2-ol Prepared using 1-[bromo(4-chlorophenyl)methyl]-4-(methylsulfonyl)benzene as described in Example 27; Mass Spectrum: m/e=518 (M+1 $^{35}$Cl) and 520 (M+1 $^{37}$Cl).

EXAMPLE 29

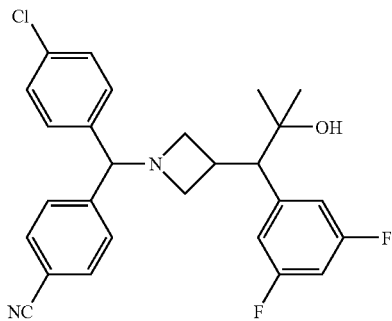

4-((4-chlorophenyl){3-[1-(3,5-difluorophenyl)-2-hydroxy-2-methylpropyl]azetidin-1-yl}methyl)benzonitrile Prepared as described in Example 27; Mass Spectrum: m/e=467 (M+1 $^{35}$Cl) and 469 (M+1 $^{37}$Cl).

EXAMPLE 30

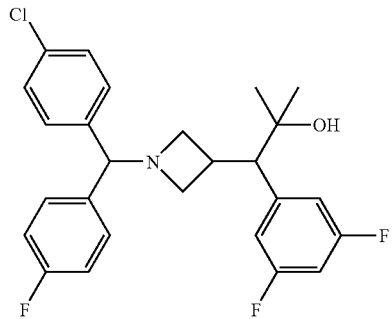

1-{1-[(4-chlorophenyl)(4-fluorophenyl)methyl]azetidin-3-yl}-1-(3,5-difluorophenyl)-2-methylpropan-2-ol Prepared as described in Example 27; Mass Spectrum: m/e=460 (M+1 $^{35}$Cl) and 462 (M+1 $^{37}$Cl).

EXAMPLE 31

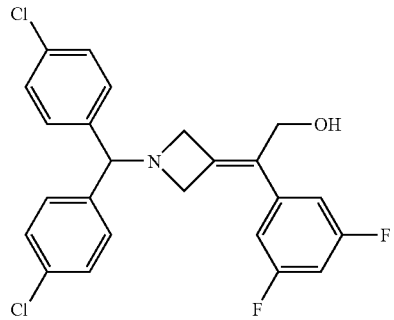

2-{1-[bis(4-chlorophenyl)methyl]azetidin-3-ylidene}-2-3,5-difluorophenyl)ethanol To a solution of 2.11 g (4.45 mmol) of methyl{1-[bis(4-chlorophenyl)methyl]azetidin-3-ylidene}(3,5-difluorophenyl)acetate in 40 mL of hexanes and 40 mL of $CH_2Cl_2$ was added a solution of 26.7 mL (26.7 mmol) of DIBAL-H (1M solution in THF) followed by stirring for 1 h at −78° C. Then the reaction mixture was warmed to rt for 1.5 h and 8 g of sodium sulfate-decahydrate was added to quench the reaction followed by stirring for 1 h at rt. The quenched reaction mixture was filtered and the organic layer concentrated. The residue was purified by silica gel chromatography with hexanes/ethyl acetate to afford the title compound as white solid. $^1$NMR(CDCl$_3$) δ 3.99 (s, 2H), 4.03 (s, 2H), 4.35 (s, 2H), 4.54 (s, 1H), 6.70-6.80 (m, 3H), 7.30-7.40 (m, 8H). Mass Spectrum: m/e=446 (M+1 $^{35}$Cl, $^{35}$Cl) and 448 (M+1 $^{35}$Cl, $^{37}$Cl).

EXAMPLE 32

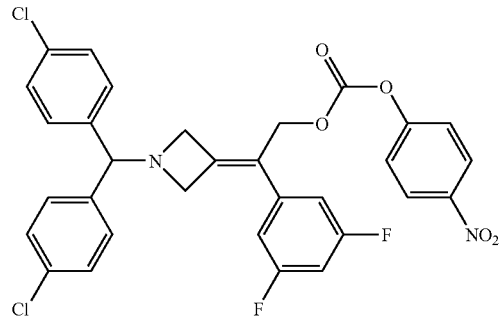

2-{1-[Bis(4-chlorophenyl)methyl]azetidin-3-ylidene}-2-(3,5-difluorophenyl)ethyl 4-nitrophenyl carbonate To a solution of 320 mg (0.717 mmol) of 2-{1-[bis(4-chlorophenyl)methyl]azetidin-3-ylidene}-2-(3,5-difluorophenyl)ethanol (Example 31) and 175 mg (1.43 mmol) of 4-dimethylaminopyridine in 10 mL of methylene chloride was added 217 mg (1.076 mmol) of 4-nitrophenyl chloroformate, and the reaction mixture was stirred for 4 h at rt. The reaction mixture was concentrated and the residue was purified by silica gel chromatography with hexanes/ethyl acetate=12:1 to afford the title compound as a white solid; Mass Spectrum m/e=613 (M+1 $^{35}$Cl, $^{35}$Cl) and 615 (M+1 $^{35}$Cl, $^{37}$Cl).

EXAMPLE 33

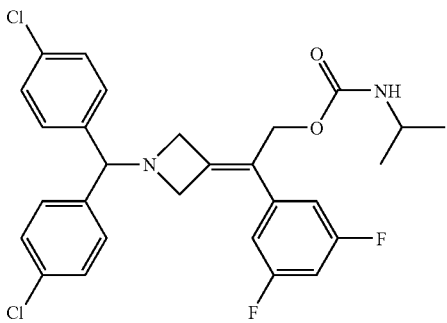

2-{1-[Bis(4-chlorophenyl)methyl]azetidin-3-ylidene}-2-3,5-difluorophenyl)ethyl isopropylcarbamate To a solution of 45 mg (0.073 mmol) of 2-{1-[bis(4-chlorophenyl)methyl]azetidin-3-ylidene}-2-(3,5-difluorophenyl)ethyl 4-nitrophenyl carbonate in 3 mL of methylene chloride was added 0.3 mL of isopropylamine and stirred for 4 h at rt. The reaction mixture was then concentrated and the residue was purified by silica gel chromatography with hexanes/ethyl acetate=4:1 to afford the title compound as a white solid. $^1$NMR(CDCl$_3$) δ 1.15 (d, 6H, J=5.7 Hz), 3.90 (br s, 1H), 3.99 (s, 2H), 4.06 (s, 2H), 4.54 (s, 1H), 4.74 (s, 2H), 6.68-6.74 (m, 3H), 7.29-7.39 (m, 8H); Mass Spectrum: m/e=531 (M+1 $^{35}$Cl, $^{35}$Cl) and 533 (M+1 $^{35}$Cl, $^{37}$Cl).

EXAMPLE 34

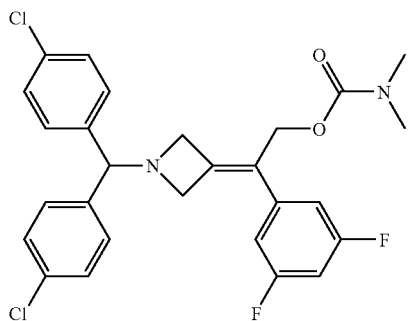

2-{1-[bis(4-chlorophenyl)methyl]azetidin-3-ylidene}-2-(3,5-difluorophenyl)ethyl dimethylcarbamate Prepared using dimethylamine as described in Example 33; Mass Spectrum: m/e=517 (M+1 $^{35}$C, $^{35}$Cl) and 519 (M+1 $^{35}$Cl, $^{37}$Cl).

EXAMPLE 35

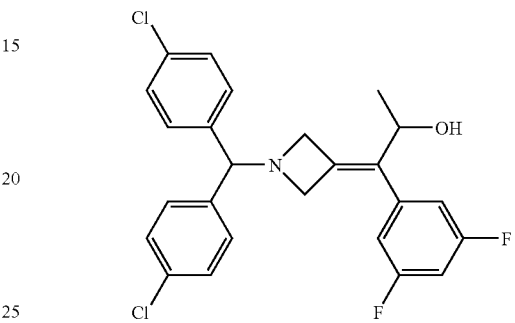

1-[bis(4-chlorophenyl)methyl]azetidin-3-ylidene}-1-(3,5-difluorophenyl)propan-2-ol Step 1: {1-[Bis(4-chlorophenyl)methyl]azetidin-3-ylidene}(3,5-difluorophenyl)acetaldehyde To a solution of 0.59 mL (6.72 mmol) of oxalyl chloride in 40 mL of methylene chloride was added slowly 0.95 mL (13.44 mmol) of DMSO at −78° C. and stirred for 20 minutes. Then a solution of 1.50 g (3.36 mmol) of 2-{1-[bis(4-chlorophenyl)methyl]azetidin-3-ylidene}(3,5-difluorophenyl) ethanol in 10 mL of methylene chloride was added into above reaction mixture and it was stirred for 30 minutes at −78° C. Then 2.32 mL (16.8 mmol) of triethylamine was added at −78° C. and the mixture was stirred for 1 h as the reaction mixture warmed from −78° C. to rt. The reaction mixture was poured into 150 mL of ether and washed with 15 mL of aq NaHCO$_3$. The organic layer was dried over Na$_2$SO$_4$ and concentrated to afford the title compound. Mass Spectrum: m/e=444 (M+1 $^{35}$Cl, $^{35}$Cl) and 446 (M+1 $^{35}$Cl, $^{37}$Cl).

Step 2: {1-[bis(4-chlorophenyl)methyl]azetidin-3-ylidene}-1-(3,5-difluorophenyl)propan-2-ol To a solution of 805 mg (1.81 mmol) of {1-[bis(4-chlorophenyl)methyl]azetidin-3-ylidene}(3,5-difluorophenyl) acetaldehyde in 20 mL of THF was added slowly a solution of 1.33 mL (4.0 mmol) of methylmagnesium chloride (3.0M solution in THF) at −78° C. and stirred for 1 h. The reaction mixture was warmed to 0° C. for 1 h and 3 g of sodium sulfate decahydrate was added to quench the reaction, followed by stirring for 1 h at rt. The quenched reaction mixture was filtered and the organic layer was dried over Na$_2$SO$_4$ and concentrated. The residue was purified by silica gel chromatography with hexanes/acetone=8:1 to afford {1-[bis(4-chlorophenyl)methyl]azetidin-3-ylidene}-1-(3,5-difluorophenyl)propan-2-ol as a white solid. Mass Spectrum m/e=460 (M+1 $^{35}$Cl, $^{35}$Cl) and 462 (M+1 $^{35}$Cl, $^{37}$Cl).

EXAMPLE 36

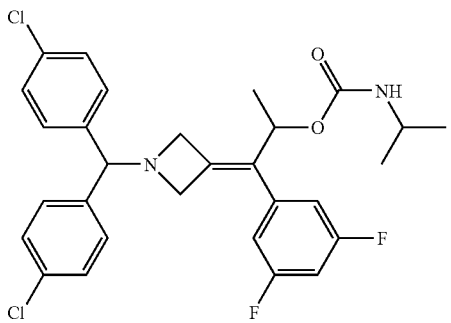

2-{1-[Bis(4-chlorophenyl)methyl]azetidin-3-ylidene}-2-(3,5-difluorophenyl)-1-methylethyl isopropylcarbamate Step 1: 2-{1-[bis(4-chlorophenyl)methyl]azetidin-3-ylidene}-2-(3,5-difluorophenyl)-1-methylethyl 4-nitrophenyl carbonate To a solution of 420 mg (0.91 mmol) of 1-{1-[bis(4-chlorophenyl)methyl]azetidin-3-ylidene}-1-(3,5-difluorophenyl)propan-2-ol, prepared according to the procedures of Example 35, and 222 mg (1.82 mmol) of 4-dimethylaminopyridine in 10 mL of methylene chloride was added 276 mg (1.37 mmol) of 4-nitrophenyl chloroformate and was stirred for 4 h at rt. The reaction mixture was concentrated and the residue was purified by silica gel chromatography with hexanes/ethyl acetate=12:1 to afford the title compound as a white solid. Mass Spectrum: m/e=627 (M+1 $^{35}$Cl, $^{35}$Cl) and 629 (M+1 $^{35}$Cl, $^{37}$Cl).

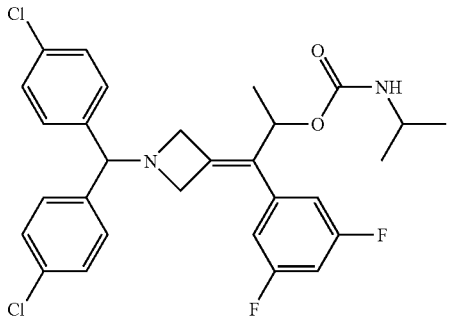

Step 2: 2-{1-[bis(4-chlorophenyl)methyl]azetidin-3-ylidene}-2-(3,5-difluorophenyl)-1-methylethyl isopropylcarbamate To a solution of 45 mg (0.073 mmol) of 2-{1-[bis(4-chlorophenyl)methyl]azetidin-3-ylidene}-2-(3,5-difluorophenyl)-1-methylethyl 4-nitrophenyl carbonate in 3 mL of methylene chloride was added 0.3 mL of isopropylamine and the reaction was stirred for 4 h at rt, followed by concentration and purification of the residue by silica gel chromatography with hexanes/ethyl acetate=4:1 to afford the title compound as white solid. Mass Spectrum: m/e=545 (M+1 $^{35}$Cl, $^{35}$Cl) and 547 (M+1 $^{35}$Cl, $^{37}$Cl).

EXAMPLE 37

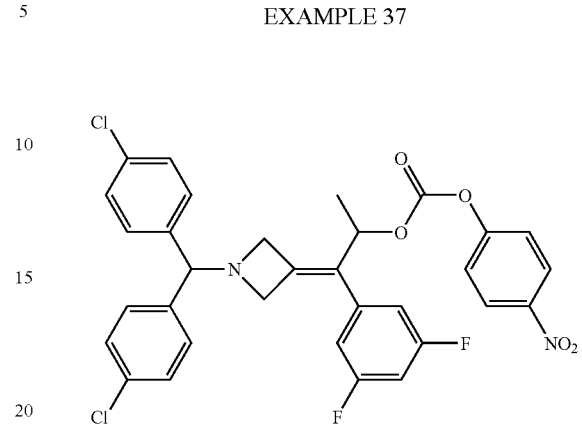

2-{1-[Bis(4-chlorophenyl)methyl]azetidin-3-ylidene}-2-3,5-difluorophenyl)-1-methylethyl 4-nitrophenyl carbonate To a solution of 420 mg (0.91 mmol) of 1-{1-[bis(4-chlorophenyl)methyl]azetidin-3-ylidene}-1-(3,5-difluorophenyl)propan-2-ol (Example 35) and 222 mg (1.82 mmol) of 4-dimethylaminopyridine in 10 mL of methylene chloride was added 276 mg (1.37 mmol) of 4-nitrophenyl chloroformate, followed by stirring for 4 h at rt. The reaction mixture was concentrated, and the residue was purified by silica gel chromatography with hexanes/ethyl acetate=12:1 to afford the title compound. Mass Spectrum: m/e=627 (M+1 $^{35}$Cl, $^{35}$Cl) and 629 (M+1 $^{35}$Cl, $^{37}$Cl).

EXAMPLE 38

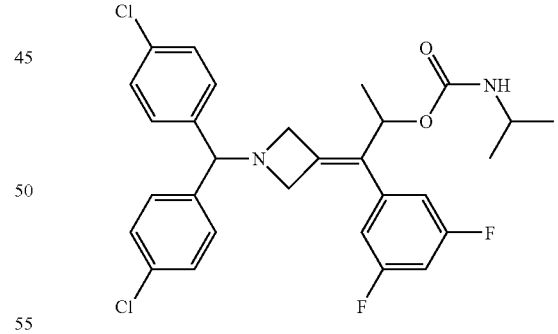

2-{1-[Bis(4-chlorophenyl)methyl]azetidin-3-ylidene}-2-(3,5-difluorophenyl)-1-methylethyl isopropylcarbamate To a solution of 45 mg (0.073 mmol) of 2-{1-[bis(4-chlorophenyl)methyl]azetidin-3-ylidene}-2-(3,5-difluorophenyl)-1-methylethyl 4-nitrophenyl carbonate (Example 37) in 3 mL of methylene chloride was added 0.3 mL of isopropylamine, followed by stirring for 4 h at rt. The reaction mixture was concentrated and the residue was purified by silica gel chromatography with hexanes/ethyl acetate=4:1 to afford the title compound; Mass Spectrum: m/e=545 (M+1 $^{35}$Cl, $^{35}$Cl) and 547 (M+1 $^{35}$Cl, $^{37}$Cl).

EXAMPLE 39

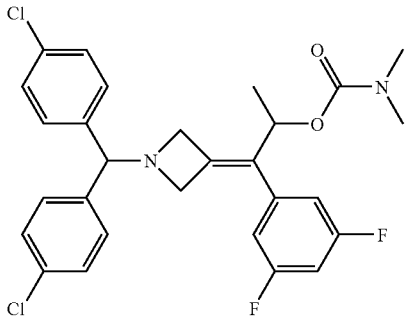

2-{1-[bis(4-chlorophenyl)methyl]azetidin-3-ylidene}-2-(3,5-difluorophenyl)-1-methylethyl dimethylcarbamate Prepared using dimethylamine as described in Example 38; Mass Spectrum m/e=531 (M+1 $^{35}$Cl, $^{35}$Cl) and 533 (M+1 $^{35}$Cl, $^{37}$Cl).

EXAMPLE 40

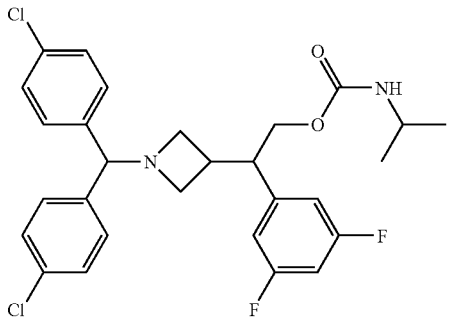

2-{1-[bis(4-chlorophenyl)methyl]azetidin-3-yl}-2-3,5-difluorophenyl)ethyl isopropylcarbamate Prepared from methyl (3,5-difluorophenyl)[1-diphenylmethyl)azetidin-3-ylidene]acetate (Preparation 5) by the procedures in Examples 37 and 38 to afford the title compound; Mass Spectrum: m/e=533 (M+1 $^{35}$Cl, $^{35}$Cl) and 535 (M+1 $^{35}$Cl, $^{37}$Cl).

EXAMPLE 41

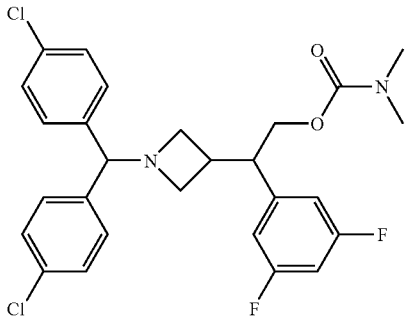

2-{1-[bis(4-chlorophenyl)methyl]azetidin-3-yl}-2-(3,5-difluorophenyl)ethyl dimethylcarbamate Prepared from methyl (3,5-difluorophenyl)[1-(diphenylmethyl)azetidin-3-ylidene]acetate (Preparation 5) and dimethylamine by the procedures in Examples 37 and 38 to afford the title compound; Mass Spectrum: m/e=519 (M+1 $^{35}$Cl, $^{35}$Cl) and 521 (M+1 $^{35}$Cl, $^{37}$Cl).

EXAMPLE 42

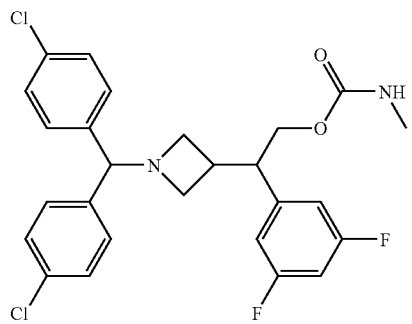

2-{1-[bis(4-chlorophenyl)methyl]azetidin-3-yl}-2-(3,5-difluorophenyl)ethyl methylcarbamate Prepared from methyl (3,5-difluorophenyl)[1-(diphenylmethyl)azetidin-3-ylidene]acetate (Preparation 5) and methylamine by the procedures in Examples 37 and 38 to afford the title compound. Mass Spectrum: m/e=505 (M+1 $^{35}$Cl, $^{35}$Cl) and 507 (M+1 $^{35}$Cl, $^{37}$Cl).

EXAMPLE 43

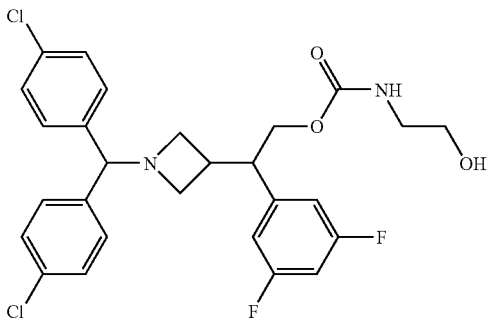

2-{1-[bis(4-chlorophenyl)methyl]azetidin-3-yl}-2-(3,5-difluorophenyl)ethyl 2-hydroxyethylcarbamate Prepared from methyl (3,5difluorophenyl)[1-(diphenylmethyl)azetidin-3-ylidene]acetate (Preparation 5) and 2-aminoethanol by the procedures in Examples 37 and 38 to afford the title compound. Mass Spectrum: m/e=535 (M+1 $^{35}$Cl, $^{35}$Cl) and 537 (M+1 $^{35}$Cl, $^{37}$Cl).

EXAMPLE 44

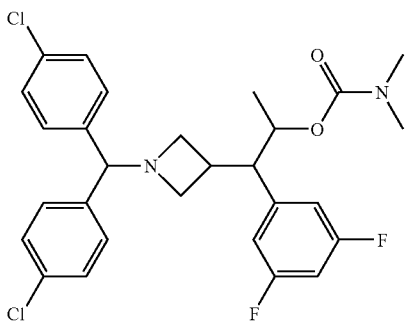

2-{1-[bis(4-chlorophenyl)methyl]azetidin-3-yl}-2-(3,5-difluorophenyl)-1-methylethyl dimethylcarbamate Prepared from {1-[bis(4-chlorophenyl)methyl]azetidin-3-yl}-1-(3,5-difluorophenyl)propan-2-ol (Example 1) and methylamine by the procedures of Examples 37 and 38 to afford the title compound. Mass Spectrum: m/e=533 (M+1 $^{35}$Cl, $^{35}$Cl) and 535 (M+1 $^{35}$Cl, $^{37}$Cl).

EXAMPLE 45

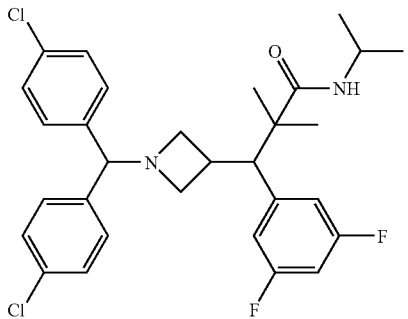

3-{1-[bis(4-chlorophenyl)methyl]azetidin-3-yl}-3-(3,5difluorophenyl)-N-isopropyl-2,2-dimethylpropanamide Prepared from {1-[bis(4-chlorophenyl)methyl]azetidin-3-yl}-1-3,5-difluorophenyl) propan-2-ol (Example 1) by the procedures of Examples 37 and 38 to afford the title compound; Mass Spectrum: m/e=545 (M+1 $^{35}$Cl, $^{35}$Cl) and 547 (M+1 $^{35}$cl, $^{37}$Cl).

EXAMPLE 46

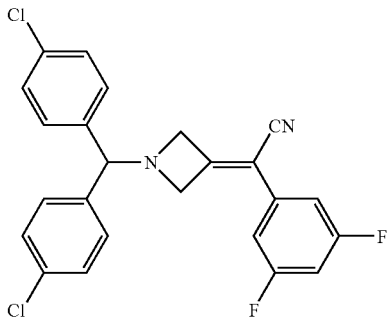

{1-[bis(4-chlorophenyl)methyl]azetidin-3-ylidene}(3,5-difluorophenyl)acetonitrile To a solution of 540 mg (3.53 mmol) of 3,5-difluorophenylacetonitrile in 8 mL of THF a solution of 1.41 mL (3.53 mmol) of butyllithium (2.5M solution in hexanes) was added and it was stirred for 30 minutes at −78° C. Then a solution of 985 mg (3.21 mmol) of 1-[bis(4-chlorophenyl)methyl]azetidin-3-one (1) in THF was added and it was stirred for 3 h at −78° C. Then 510 mg (4.17 mmol) of 4-dimethylaminopyridine, 840 uL(4.82 mmol) of N,N-diisopropylethylamine and 558 uL (7.06 mmol) of methanesulfonyl chloride was added and it was stirred at −78° C. to rt overnight. The solution was poured into 80 mL of ether and washed with 10 mL of aq NaHCO$_3$. The organic layer was dried over Na$_2$SO$_4$ and concentrated. The residue was purified by silica gel chromatography with hexanes/ethyl acetate=9:1 to afford the title compound; $^1$NMR(CDCl$_3$) δ 3.84 (m, 2H), 4.25 (m, 2H), 4.54 (s, 1H), 6.76 (m, 1H), 6.78 (m, 2H), 7.33 (m, 3H), 7.38 (m, 2H); Mass Spectrum: m/e=430 (M+1 $^{35}$Cl, $^{35}$Cl) and 432 (M+1 $^{35}$Cl, $^{37}$Cl).

EXAMPLE 47

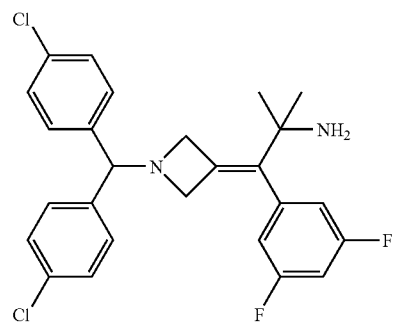

1-{1-[bis(4-chlorophenyl)methyl]azetidin-3-ylidene}-1-(3,5-difluorophenyl)-2-methylpropan-2-amine A sample of 236 mg anhydrous CeCl$_3$ (0.96 mmol) was dried with magnetic stirring under N$_2$ at 150-160° C. for 40 min. Then 6 mL of dry THF was added and the suspension was stirred at 25° C. After 2 h, 600 uL of a 1.6 M of methyllithium solution in THF, 0.96 mmol) was added at −78° C. After 30 min, a solution of 201 mg (0.46 mmol) of {1-[bis(4-chlorophenyl)methyl]azetidin-3-ylidene}(3,5-difluorophenyl)acetonitrile in 2 mL of THF was added and the mixture was stirred at −78° C. for 3 h. Concentrated NH$_4$OH (3 mL) was added with the temperature lower than −60° C. and the mixture was brought to rt and filtered through CELITE. The solids were washed several times with methylene chloride and the aqueous layer was extracted twice with methylene chloride. The combined organic layers were dried and concentrated. The residue was purified by silica gel chromatography with hexanes/ethyl acetate/2 M NH$_3$ in MEOH=100:30:6 to afford the title compound; $^1$NMR(CDCl$_3$) δ 1.28 (s, 6H), 3.14 (S, 2H), 3.95 (s, 2H), 4.66 (s, 1H), 6.56 (m, 2H), 6.77 (m, 1H), 7.21-7.28 (m, 8H); Mass Spectrum m/e=473 (M+1 $^{35}$Cl, $^{35}$Cl) and 475 (M+1 $^{35}$Cl, $^{37}$Cl).

EXAMPLE 48

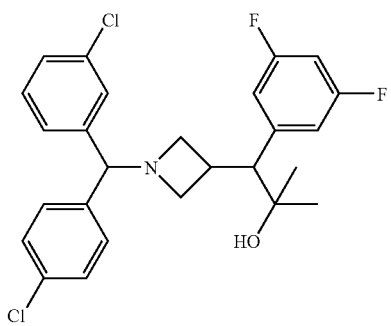

1-{1-[(3-chlorophenyl)(4-chlorophenyl)methyl]azetidin-3-yl}-1-(3,5-difluorophenyl)-2-methylpropan-2-ol A solution of 0.985 g (4.0 mmole) of finely powdered CeCl$_3$ (Strem Chemical Co.) in 10 mL anhydrous THF was stirred at room temperature under N$_2$. After 1 h, the solution was cooled to −78° C. in a dry ice-acetone bath and 2.5 mL of a 1.6M solution of methyllithium in ether was added dropwise at such a rate that the solids remained dispersed. After 30 minutes, a solution of 0.485 g (1.1 mmole) of methyl{1-[(3-chlorophenyl)(4-chlorophenyl)methyl]azetidin-3-yl}(3,5-difluorophenyl)acetate in 5 mL of THF was added and the solution was left stirring at −78° C. for 1 h. The reaction was quenched by addition of 0.1 mL of methanol, diluted with 40 mL of ether and allowed to warm to −10° C. Then aqueous NH$_4$Cl solution was added dropwise until the cerium salts precipitated onto the surface of the flask. The supernatant was decanted and the solids were triturated with two 20 mL portions of dichloromethane and two 20 mL portions of ether. The combined organic extracts were washed with saturated aqueous NH$_4$Cl solution and brine, dried over Na$_2$SO$_4$ and concentrated to afford the title compound as a mixture of 4 diastereomers. The mixture was purified by flash chromatography on silica gel using a step gradient of 3 column volumnes each of 1%, then 2%, then 4%, then 6% ethyl acetate-hexane to afford two diastereomers of the title compound. The enantiomers of the faster diastereomer were separated by chromatography on an AD column chiral using 6% isopropanol in heptane.

Faster diastereomer: $^1$H NMR(CDCl$_3$) δ 1.07 (s, 3H), 1.14 (S, 3H), 2.28 (t, 1H, J=7.5 Hz), 2.74 (d, 1H, J=10.7 Hz), 2.82 (t, 1H, J=7.5 Hz), 3.10-3.16 (m, 2H), 3.62 (m, 1H), 4.20 (s, 1H), 6.67-6.73 (m, 3H), 7.21-7.33 (m, 8H); Mass Spectrum: m/e=476 (M+1 $^{35}$Cl, $^{35}$Cl) and 478 (M+1 $^{35}$Cl, $^{37}$Cl).

Slower diastereomer $^1$H NMR(CDCl$_3$) δ 1.06 (s, 3H), 1.14 (S, 3H), 2.29 (t, 1H, J=7.5 Hz), 2.75 (d, 1H, J=10.7 Hz), 2.82 (t, 1H, J=7.5 Hz), 3.10-3.16 (m, 2H), 3.62 (m, 1H), 4.22 (s, 1H), 6.67-6.73 (m, 3H), 7.21-7.33 (m, 8H); Mass Spectrum: m/e=476 (M+1 $^{35}$Cl, $^{35}$Cl) and 478 (M+1 $^{35}$Cl, $^{37}$Cl).

EXAMPLE 49

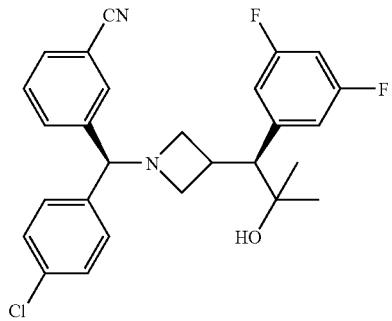

3-((S)-(4-chlorophenyl){3-[(1S)-1-(3,5-difluorophenyl)-2-hydroxy-2-methylpropyl]azetidin-1-yl}methyl)benzonitrile Step 1: (1S)-1-(3,5-difluorophenyl)-1-[1-(diphenylmethyl)azetidin-3-yl]-2-methylpropan-2-ol A suspension of 67.03 g (272 mmole) of CeCl$_3$ in 500 mL dry THF was stirred in a 2L three-necked flask under N$_2$ at rt. After 30 minutes, the mixture was cooled to −78° C. in a dry ice-acetone bath and 155 mL of a 1.6M solution of methyllithium in ether was added dropwise with vigorous stirring. The yellow-green mixture was stirred at −78° C. for an additional 30 minutes and then a solution of 28.75 g (70.6 mmole) of methyl (3,5-difluorophenyl)[1-(diphenylmethyl)azetidin-3-yl]acetate in 100 mL of dry THF was added over 30 minutes, at such a rate as to keep the temperature below −60° C. The mixture was left stirring at −78° C. for 1 h, then excess carbanion was decomposed by the dropwise addition of 20 mL of methanol and 1000 mL of ether while the solution warmed to −40° C. The reaction was quenched by addition of saturated aqueous NH$_4$Cl until the most of the solids had precipitated to the bottom surface of the flask. The liquid layer was decanted into a 2L separatory funnel and the solids were triturated with three 200 mL portions of dichloromethane. The combined organic layers were washed with two 400 mL portions of aqueous NH$_4$Cl solution and brine, then dried over Na$_2$SO$_4$ and concentrated to a white solid. The residue was purified on ChiralPak AD resin using 5% isopropanol-heptane. Fractions containing the faster enantiomer were pooled and concentrated to afford the title compound, which is the (+) enantiomer; $^1$H NMR(CDCl$_3$) δ 1.07 (s, 3H), 1.14 (S, 3H), 2.28 (t, 1H, J=7.5 Hz), 2.74 (d, 1H, J=10.7 Hz), 2.82 (t, 1H, J=7.5 Hz), 3.10-3.16 (m, 2H), 3.62 (m, 1H), 4.20 (s, 1H), 6.67-6.73 (m, 3H), 7.21-7.45 (m, 10H); Mass Spectrum: m/e=408.

Step 2: (1S)-1-azetidin-3-yl-1-(3,5-difluorophenyl)-2-methylpropan-2-ol

A 500 mL Parr flask was purged with N$_2$ and charged with 1.2 g of 10% Pd/C and 20 mL of methanol. To this was added a solution of 4.1 g (10.1 mmole) of (1S)-1-(3,5-difluorophenyl)-1-[1-(diphenylmethyl)azetidin-3-yl]-2-methylpropan-2-ol and the mixture was shaken under 40 psi H$_2$ for 24 h. The mixture was filtered through CELITE and the filtrate was concentrated. The oily residue was applied to a silica gel column packed in 20% ethyl acetate-hexane and the column was washed with 5 column volumes of 20% ethyl acetate-hexane, then with dichloromethane, with 10% methanol in dichloromethane and finally with 60:40:10 dichloromethane-methanol-ammonium hydroxide. Homogenous fractions were concentrated to afford the title compound, which was not further purified but was used directly in the next step; Mass Spectrum: m/e=244 (M+1).

Step 3: 3-((S)-(4-chlorophenyl){3-[(1S)-1-(3,5-difluorophenyl)-2-hydroxy-2-methylpropyl]azetidin-1-yl}methyl)benzonitrile A solution of the crude amine from Step 3 and 6.51 g (20 mmole) of $Cs_2CO_3$ in 30 mL dry acetonitrile was stirred at rt in a flask fitted with a small Dean-Stark trap. After 15 minutes, 4.6 g (15 mmole) 3-[bromo(4-chlorophenyl)methyl] benzonitrile was added and the mixture was heated at 60° C. After 18 h, the solution was filtered through CELITE and the residue was washed with acetonitrile. The combined filtrates were concentrated and the residue was purified by flash chromatography using a step gradient of 5 to 20% ethyl acetate-hexane. Fractions containing the faster product diastereomer were pooled and concentrated to afford the title compound; $^1$NMR(CDCl$_3$) δ 1.07 (s, 3H), 1.14 (S, 3H), 2.28 (t, 1H, J=7.5 Hz), 2.74 (d, 1H, J=10.7 Hz), 2.82 (t, 1H, J=7.5 Hz), 3.10-3.16 (m, 2H), 3.62 (m, 1H), 4.29 (s, 1H), 6.67-6.73 (m, 3H), 7.21-7.4 (m, 8H); Mass Spectrum: m/e=469 (M+1, $^{35}$Cl) and 4.71 (M+1, $^{37}$Cl).

EXAMPLES 50-69

The following examples were prepared from the corresponding esters according to the procedures described in Examples 48 and 49.

| Example | Name | Ar | R4 | Mass Spectrum m/e |
|---|---|---|---|---|
| 50 | 1-(3,5-difluorophenyl)-1-[1-(diphenylmethyl)azetidin-3-yl]-2-methylpropan-2-ol | phenyl | phenyl | 408 (M+1) |
| 51 | 1-{1-[bis(4-chlorophenyl)methyl]azetidin-3-yl}-1-(3,5-difluorophenyl)-2-methylpropan-2-ol | 4-chlorophenyl | 4-chlorophenyl | 476 (M+1 $^{35}$Cl, $^{35}$Cl) 478 (M+1 $^{35}$Cl, $^{37}$Cl) |
| 52 | 1-{1-[(4-chlorophenyl)(phenyl)methyl]azetidin-3-yl}-1-(3,5-difluorophenyl)-2-methylpropan-2-ol | 4-chlorophenyl | phenyl | 472 (M+1 $^{35}$Cl); 474 (M+1, $^{37}$Cl) |
| 53 | (1S)-1-{1-[(R)-(4-chlorophenyl)(phenyl)methyl]azetidin-3-yl}-1-(3,5-difluorophenyl)-2-methylpropan-2-ol | 4-chlorophenyl | phenyl | 472 (M+1 $^{35}$Cl); 474 (M+1, $^{37}$Cl) |
| 54 | (1R)-1-{1-[(S)-(4-chlorophenyl)(phenyl)methyl]azetidin-3-yl}-1-(3,5-difluorophenyl)-2-methylpropan-2-ol | 4-chlorophenyl | phenyl | 472 (M+1 $^{35}$Cl); 474 (M+1, $^{37}$Cl) |
| 55 | 4-((4-chlorophenyl){3-[1-(3,5-difluorophenyl)-2-hydroxy-2-methylpropyl]azetidin-1-yl}methyl)benzonitrile | 4-chlorophenyl | 3-cyanophenyl | 467 (M+1, $^{35}$Cl); 469 (M+1, $^{37}$Cl) |

-continued

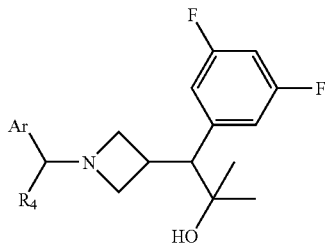

| Example | Name | Ar | R4 | Mass Spectrum m/e |
|---|---|---|---|---|
| 56 | 3-((R)-(4-chlorophenyl){3-[(1R)-1-(3,5-difluorophenyl)-2-hydroxy-2-methylpropyl]azetidin-1-yl}methyl)benzonitrile | 4-Cl-phenyl | 3-CN-phenyl | 467 (M+1, $^{35}$Cl); 469 (M+1, $^{37}$Cl) |
| 57 | 3-((S)-(4-chlorophenyl){3-[(1S)-1-(3,5-difluorophenyl)-2-hydroxy-2-methylpropyl]azetidin-1-yl}methyl)benzonitrile | 4-Cl-phenyl | 3-CN-phenyl | 467 (M+1, $^{35}$Cl); 469 (M+1, $^{37}$Cl) |
| 58 | 3-((R)-(4-chlorophenyl){3-[(1S)-1-(3,5-difluorophenyl)-2-hydroxy-2-methylpropyl]azetidin-1-yl}methyl)benzonitrile | 4-Cl-phenyl | 3-CN-phenyl | 467 (M+1, $^{35}$Cl); 469 (M+1, $^{37}$Cl) |
| 59 | 3-((S)-(4-chlorophenyl){3-[(1R)-1-(3,5-difluorophenyl)-2-hydroxy-2-methylpropyl]azetidin-1-yl} methyl)benzonitrile | 4-Cl-phenyl | 3-CN-phenyl | 467 (M+1, $^{35}$Cl); 469 (M+1, $^{37}$Cl) |
| 60 | (1RS)-1-(1-{(SR)-(4-chlorophenyl)[4-(methylsulfonyl)phenyl]methyl}azetidin-3-yl)-1-(3,5-difluorophenyl)-2-methylpropan-2-ol | 4-Cl-phenyl | 4-SO$_2$CH$_3$-phenyl | 520 (M+1 $^{35}$Cl); 522 (M+11, $^{37}$Cl) |
| 61 | (1RS)-1-(1-{(RS)-(4-chlorophenyl)[4-(methylsulfonyl)phenyl]methyl}azetidin-3-yl)-1-(3,5-difluorophenyl)-2-methylpropan-2-ol | 4-Cl-phenyl | 4-SO$_2$CH$_3$-phenyl | 520 (M+1 $^{35}$Cl); 522 (M+11, $^{37}$Cl) |
| 62 | 1-{1-[(4-chlorophenyl)(4-fluorophenyl)methyl]azetidin-3-yl}-1-(3,5-difluorophenyl)-2-methylpropan-2-ol | 4-Cl-phenyl | 4-F-phenyl | 460 (M+1 $^{35}$Cl); 462 (M+1 $^{37}$Cl) |

-continued

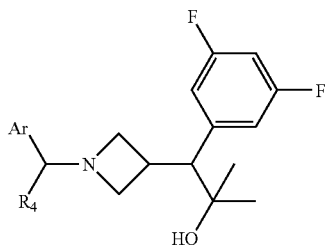

| Example | Name | Ar | R4 | Mass Spectrum m/e |
|---|---|---|---|---|
| 63 | 1-{1-[bis(4-fluorophenyl)methyl]azetidin-3-yl}-1-(3,5-difluorophenyl)-2-methylpropan-2-ol | 4-F-C6H4 | 4-F-C6H4 | 444 (M+1) |
| 64 | (1SR)-1-{1-[(SR)-(2-chlorophenyl)(4-chlorophenyl)methyl]azetidin-3-yl}-1-(3,5-difluorophenyl)-2-methylpropan-2-ol | 4-Cl-C6H4 | 2-Cl-C6H4 | 476 (M+1 $^{35}$Cl, $^5$Cl); 478 (M+1 $^{35}$Cl, $^{37}$Cl) |
| 65 | (1RS)-1-{1-[(SR)-(2-chlorophenyl)(4-chlorophenyl)methyl]azetidin-3-yl}-1-(3,5-difluorophenyl)-2-methylpropan-2-ol | 4-Cl-C6H4 | 2-Cl-C6H4 | 476 (M+1 $^{35}$Cl, $^{35}$Cl); 478 (M+1 $^{35}$Cl, $^{37}$Cl) |
| 66 | (1SR)-1-{1-[(SR)-(2-chlorophenyl)(4-fluorophenyl)methyl]azetidin-3-yl}-1-(3,5-difluorophenyl)-2-methylpropan-2-ol | 4-F-C6H4 | 2-Cl-C6H4 | 460 (M+1 $^{35}$Cl); 462 (M+1 $^{37}$Cl) |
| 67 | (1RS)-1-{1-[(SR)-(2-chlorophenyl)(4-fluorophenyl)methyl]azetidin-3-yl}-1-(3,5-difluorophenyl)-2-methylpropan-2-ol | 4-F-C6H4 | 2-Cl-C6H4 | 460 (M+1 $^{35}$Cl); 462 (M+1 $^{37}$Cl) |
| 68 | 3-((R)-(4-chloro-3-iodophenyl){3-[(1S)-1-(3,5-difluorophenyl)-2-hydroxy-2-methylpropyl]azetidin-1-yl}methyl)benzonitrile | 4-Cl-3-I-C6H3 | 3-CN-C6H4 | 593(M+1, $^{35}$Cl); 595 (M+1, $^{37}$Cl) |
| 69 | 3-((S)-(4-chloro-3-iodophenyl){3-[(1S)-1-(3,5-difluorophenyl)-2-hydroxy-2-methylpropyl]azetidin-1-yl}methyl)benzonitrile | 4-Cl-3-I-C6H3 | 3-CN-C6H4 | 593(M+1, $^{35}$Cl); 595 (M+1, $^{37}$Cl) |

EXAMPLE 70

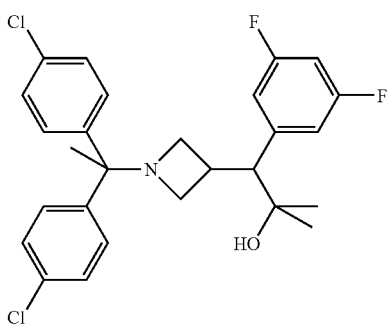

1-{1-[1,1-bis(4-chlorophenyl)ethyl]azetidin-3-yl}-1-
(3,5-difluorophenyl)-2-methylpropan-2-ol Prepared from methyl {1-[1,1-bis(4-chlorophenyl)ethyl] azetidin-3-yl}(3,5-difluorophenyl)acetate using the procedure described in Example 48; Mass Spectrum: m/e=490 (M+1 $^{35}$Cl, $^{35}$Cl); 492 (M+1 $^{35}$Cl, $^{37}$Cl).

EXAMPLE 71

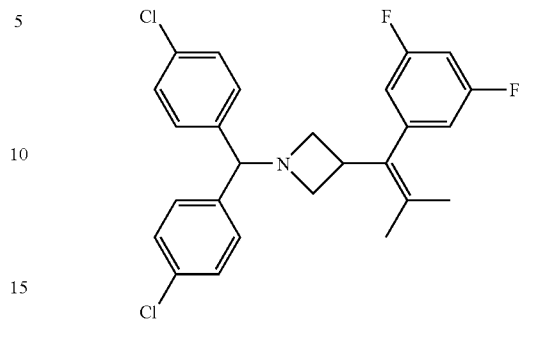

1-[bis(4-chlorophenyl)methyl]-3-[1-(3,5-difluorophenyl)-2-methylprop-1-en-1-yl]azetidine To a solution of 47 mg (0.099 mmol) of 1-{1-[bis(4-chlorophenyl)methyl]azetidin-3-yl}-1-(3,5-difluorophenyl)-2-methylpropan-2-ol in 0.5 mL of CH$_2$Cl$_2$ 52 uL (0.395 mmol) of DAST (diethylaminosulfur trifluoride) was added and the solution was stirred for 2 h at −78° C. Then to the reaction mixture was added 10 mL of ether and 3 mL of aq NaHCO$_3$. The pH was adjusted to 8-9 with 2N NaOH. The water layer was extracted with CH$_2$Cl$_2$ (3×10 mL). The combined organic layer was dried over Na$_2$SO$_4$ and concentrated. The residue was purified by silica gel chromatography with hexanes/ethyl acetate to afford the title compound as a white solid; $^1$H NMR(CDCl$_3$) δ 1.51 (s, 3H), 1.71 (s, 3H), 2.60 (t, J=7.8 Hz, 2H), 3.36 (t, J=7.6 Hz, 2H), 3.70 (m, 1H), 4.06 (s, 1H), 6.56 (m, 2H), 6.73 (m, 1H), 7.24 (m, 8H); Mass Spectrum: m/e=458 (M+1 $^{35}$Cl, $^{35}$Cl) and 460 (M+1 $^{35}$Cl, $^{37}$Cl).

EXAMPLES 72-73

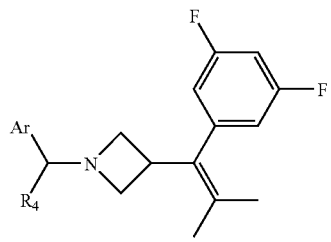

| Example | Name | Ar | R4 | Mass Spectrum m/e |
|---|---|---|---|---|
| 72 | 3-[1-(3,5-difluorophenyl)-2-methylprop-1-en-1-yl]-1-(diphenylmeethyl)azetidine | phenyl | phenyl | 390 (M+1) |
| 73 | 3-((4-chlorophenyl){3-[1-(3,5-difluorophenyl)-2-methylprop-1-en-1-yl]azetidin-1-yl}methyl)benzonitrile | 4-chlorophenyl | 3-cyanophenyl | 449 (M+1, $^{35}$Cl); 451 (M+1, $^{37}$Cl) |

EXAMPLE 74

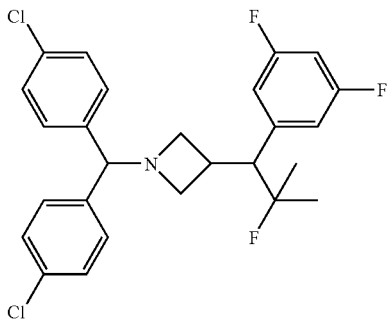

1-[bis(4-chlorophenyl)methyl]-3-[(1S)-1-(3,5-difluorophenyl)-2-fluoro-2-methylpropyl]azetidine To a solution of 175 mg (0.368 mmol) of 1-{1-[bis(4-chlorophenyl)methyl]azetidin-3-yl}-1-(3,5-difluorophenyl)-2-methylpropan-2-ol in 3 mL of $CH_2Cl_2$, 1 mL of hydrogen fluoride-pyridine was added and the reaction was stirred for 9 h at 42° C. Then the reaction mixture was poured to 7 mL of 5N NaOH, 7 mL of ag $NaHCO_3$ and 30 mL of $CH_2Cl_2$. Adjusted pH to 8-9 with 2N NaOH. The water layer was extracted with $CH_2Cl_2$ (3×30 mL). The combined organic layer was dried over $Na_2SO_4$ and concentrated. The residue was purified by silica gel chromatography with 10% methyl tert-butyl ether-hexane to afford the title compound as a white solid. $^1H$ NMR($CDCl_3$) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.20 (s, 1H), 6.68-6.71 (m, 3H), 7.21-7.33 (m, 8H)

EXAMPLE 75

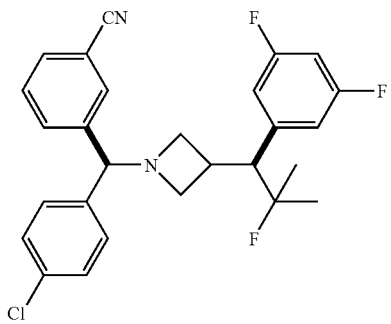

3-((S)-(4-chlorophenyl){3-[(1S)-1-(3,5-difluorophenyl)-2-fluoro-2-methylpropyl]azetidin-1-yl}methyl)benzonitrile To a solution of 186 mg (0.368 mmol) of 3-((S)-(4-chlorophenyl){3-[(1S)-1-(3,5-difluorophenyl)-2-hydroxy-2-methylpropyl]azetidin-1-yl}methyl)benzonitrile in 3 mL of $CH_2Cl_2$, 1 mL of hydrogen fluoride-pyridine was added and it was stirred for 9 h at 42° C. Then the reaction mixture was poured to 7 mL of 5N NaOH, 7 mL of ag $NaHCO_3$ and 30 mL of $CH_2Cl_2$. The pH was adjusted to 8-9 with 2N NaOH. The water layer was extracted with $CH_2Cl_2$ (3×30 mL). The combined organic layer was dried over $Na_2SO_4$ and concentrated. The residue was purified by silica gel chromatography with 10% methyl tert-butyl ether-hexane to afford the title compound as a white solid; $^1$NMR($CDCl_3$) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.24 (s, 1H), 6.68-6.71 (m, 3H), 7.21-7.8 (m, 8H); Mass Spectrum: m/e=478 (M+1 $^{35}Cl$, $^{35}Cl$) and 480 (M+1 $^{35}Cl$, $^{37}Cl$).

EXAMPLE 76

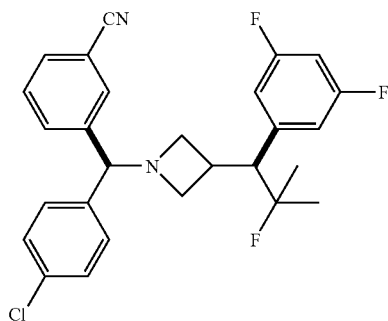

3-((S)-(4-chlorophenyl){3-[(1S)-1-(3,5-difluorophenyl)-2-fluoro-2-methylpropyl]azetidin-1-yl}methyl)benzonitrile Step 1: (1S)-1-(3,5-difluorophenyl)-1-[1-(diphenylmethyl)azetidin-3-yl]-2-methylpropan-2-ol A suspension of 67.03 g (272 mmole) of $CeCl_3$ in 500 mL dry THF was stirred in a 2L three-necked flask under $N_2$ at rt. After 30 minutes, the mixture was cooled to −78° C. in a dry ice-acetone bath and 155 mL of a 1.6M solution of methyllithium in ether was added dropwise with vigorous stirring. The yellow-green mixture was stirred at −78° C. for an additional 30 minutes and then a solution of 28.75 g (70.6 mmole) of methyl (3,5-difluorophenyl)[1-(diphenylmethyl)azetidin-3-yl]acetate in 100 mL of dry THF was added over 30 minutes, at such a rate as to keep the temperature below −60° C. The mixture was left stirring at −78° C. for 1 h, then excess carbanion was decomposed by the dropwise addition of 20 mL of methanol and 1000 mL of ether while the solution warmed to −40° C. The reaction was quenched by addition of saturated aqueous $NH_4Cl$ until the most of the solids had precipitated to the bottom surface of the flask. The liquid layer was decanted into a 2L separatory funnel and the solids were triturated with three 200 mL portions of dichloromethane. The combined organic layers were washed with two 400 mL portions of aqueous $NH_4Cl$ solution and brine, then dried over $Na_2SO_4$ and concentrated to a white solid. The residue was purified on ChiralPak AD resin using 5% isopropanol-heptane. Fractions containing the faster enantiomer were pooled and concentrated to afford the title compound, which is the (+) enantiomer; $^1H$ NMR($CDCl_3$) δ 1.07 (s, 3H), 1.14 (S, 3H), 2.28 (t, 1H, J=7.5 Hz), 2.74 (d, 1H, J=10.7 Hz), 2.82 (t, 1H, J=7.5 Hz), 3.10-3.16 (m, 2H), 3.62 (m, 1H), 4.20 (s, 1H), 6.67-6.73 (m, 3H), 7.21-7.45 (m, 10H); Mass Spectrum: m/e=408.

Step 2: 3-[(1S)-1-(3,5-difluorophenyl)-2-fluoro-2-methylpropyl]-1-diphenylmethyl)azetidine To a solution of 5.5 g (13.5 mmole) of (1S)-1-(3,5-difluorophenyl)-1-[1-(diphenylmethyl)azetidin-3-yl]-2-methylpropan-2-ol in 25 mL of $CH_2Cl_2$ was added 15 mL of hydrogen fluoride-pyridine and the two-phase mixture was stirred for 15 h at 42° C. Then the reaction mixture was poured to 100 mL of 5N NaOH, 20 mL of aq NaHCO₃, 150 mL of CH₂Cl₂ and 100 mL ice. The pH was adjusted to 8-9 with 2N NaOH. The water layer was extracted with CH₂Cl₂ (3×1500 mL). The combined organic layer was dried over Na₂SO₄ and concentrated. The residue was purified by silica gel chromatography with 10% methyl tert-butyl ether-hexane to afford the title compound as a white solid; $^1$NMR(CDCl₃) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.30 (s, 1H), 6.68-6.71 (m, 3H), 7.21-7.8 (m, 10H); Mass Spectrum: m/e=410 (M+1)

Step 3: 3-[(1S)-1-(3,5-difluorophenyl)-2-fluoro-2-methylpropyl]azetidine

A 500 mL Parr flask was purged with N₂ and charged with 1.2 g of 10% Pd/C and 20 mL of methanol. To this was added a solution of 4.1 g (10.1 mmole) of 3-[(1S)-1-(3,5difluorophenyl)-2-fluoro-2-methylpropyl]-1-diphenylmethyl)azetidine and the mixture was shaken under 40 psi H2 for 24 h. The mixture was filtered through CELITE and the filtrate was concentrated. The oily residue was applied to a silica gel column packed in 20% ethyl acetate-hexane and the column was washed with 5 column volumes of 20% ethyl acetate-hexane, then with dichloromethane, with 10% methanol in dichloromethane and finally with 80:20:2 dichloromethane-methanol-ammonium hydroxide. Homogenous fractions were concentrated to afford the title compound, which was not further purified but was used directly in the next step; Mass Spectrum: m/e=244 (M+1).

Step 4: 3-((S)-(4-chlorophenyl){3-[(1S)-1-(3,5-difluorophenyl)-2-fluoro-2-methylpropyl]azetidin-1-yl}methyl)benzonitrile A solution of the crude amine from Step 3 and 6.51 g (20 mmole) of Cs₂CO₃ in 30 mL dry acetonitrile was stirred at rt in a flask fitted with a small Dean-Stark trap. After 15 minutes, 4.6 g (15 mmole) of 3-[bromo(4-chlorophenyl)methyl]benzonitrile was added and the mixture was heated at 60° C. After 18 h, the solution was filtered through CELITE and the residue was washed with acetonitrile. The combined filtrates were concentrated and the residue was purified by flash chromatography using a step gradient of 5 to 20% ethyl acetate-hexane. Fractions containing the faster product diastereomer were pooled and concentrated to afford the title compound; $^1$NMR(CDCl₃) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.24 (s, 1H), 6.68-6.71 (m, 3H), 7.21-7.8 (m, 8H); Mass Spectrum m/e=469 (M+1, $^{35}$Cl) and 471 (M+1, $^{37}$Cl).

EXAMPLE 77

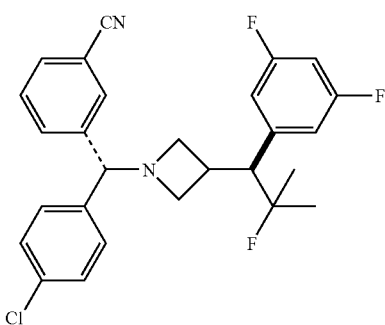

3-((R)-(4-chlorophenyl){3-[(1S)-1-(3,5-difluorophenyl)-2-fluoro-2-methylpropyl]azetidin-1-yl}methyl)benzonitrile Further elution of the flash column of Step 4 of Example 76 afforded the title compound as a white solid; $^1$NMR(CDCl₃) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.20 (s, 1H), 6.68-6.71 (m, 3H), 7.21-7.8 (m, 8H); Mass Spectrum: m/e=469 (M+1, $^{35}$Cl) and 471 (M+1, $^{37}$Cl).

EXAMPLE 78

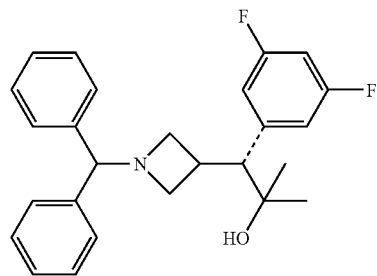

(1R)-1-(3,5-difluorophenyl)-1-[1-(diphenylmethyl)azetidin-3-yl]-2-methylpropan-2-ol Further elution of the AD column of Step 1 of Example 76 afforded the title compound, which is the (−) enantiomer; $^1$NMR(CDCl₃) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.20 (s, 1H), 6.68-6.71 (m, 3H), 7.21-7.8 (m, 8H); Mass Spectrum: m/e=408 (M+1).

EXAMPLE 79

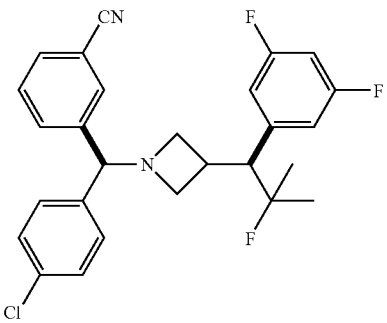

3-((S)-(4-chlorophenyl){3-[(1S)-1-(3,5-difluorophenyl)-2-fluoro-2-methylpropyl]azetidin-1-yl}methyl)benzonitrile Step 1: 3-[(1S)-1-(3,5-difluorophenyl)-2-fluoro-2-methylpropyl]azetidine A sample of 2.25 g (5.5 mmole) of 3-[(1S)-1-(3,5-difluorophenyl)-2-fluoro-2-methylpropyl]-1-(diphenylmethyl)azetidine (Step 2 of Example 76) was dissolved in 15 mL of THF and 1.1 mL (10 mmole) of 1-chloroethyl chloroformate was added. The solution was stirred at room temperature.

After 2 h, the solution was concentrated under reduced pressure and the residue was dried under high vacuum for 1 h. The residue was dissolved in 20 mL of methanol and heated to reflux for 6 h. The solution was concentrated and the residue was partitioned between 100 mL ether and 50 mL of 1:1 saturated $Na_2CO_3$ solution-1M NaOH. The aqueous layer was washed with 3 portions of 100 mL ether and the combined organic extracts were washed with $NaHCO_3$, then brine, then concentrated. The oily residue was applied to a silica gel column packed in 20% ethyl acetate-hexane and the column was washed with 5 column volumes of 20% ethyl acetate-hexane, then with dichloromethane, with 10% methanol in dichloromethane and finally with 80:20:2 dichloromethane-methanol-ammonium hydroxide. Homogenous fractions were concentrated to afford the title compound, which was not further purified but was used directly in the next step; Mass Spectrum m/e=244 (M+1).

Step 2: 3-((S)-(4-chlorophenyl){3-[(1S)-1-(3,5-difluorophenyl)-2-fluoro-2-methylpropyl]azetidin-1-yl}methyl)benzonitrile A solution of the crude amine from Step 1 and 3.4 g (1.1 mmole) of $Cs_2CO_3$ in 10 mL dry acetonitrile was stirred at rt in a flask fitted with a small Dean-Stark trap. After 15 minutes, 2.3 g (7.5 mmole) of 3-[bromo(4-chlorophenyl)methyl]benzonitrile was added and the mixture was heated at 60° C. After 18 h, the solution was filtered through CELITE and the residue was washed with acetonitrile. The combined filtrates were concentrated and the residue was purified by flash chromatography using a step gradient of 5 to 20% ethyl acetate-hexane. Fractions containing the faster product diastereomer were pooled and concentrated to afford the title compound; $^1$NMR(CDCl$_3$) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.24 (s, 1H), 6.66-6.71 (m, 3H), 7.21-7.8 (m, 8H); Mass Spectrum: m/e=469 (M+1, $^{35}$Cl) and 471 (M+1, $^{37}$Cl).

EXAMPLE 80

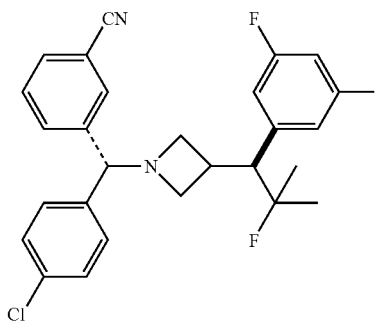

3-((R)-(4-chlorophenyl){3-[(1S)-1-(3,5-difluorophenyl)-2-fluoro-2-methylpropyl]azetidin-1-yl}methyl)benzonitrile Further elution of the column from Step 4 of Example 79 afforded the title compound and slower product diastereomer; $^1$NMR(CDCl$_3$) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.20 (s, 1H), 6.68-6.71 (m, 3H), 7.21-7.8 (m, 8H); Mass Spectrum: m/e=469 (M+1, $^{35}$Cl) and 471 (M+1, $^{37}$Cl).

EXAMPLES 81-108

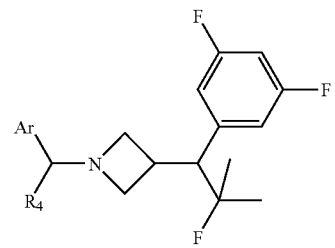

The following analogs were prepared using the methods described in Examples 72, 73, 74 and 77.

| Example | Name3 | Ar | R4 | Mass Spectrum m/e |
|---|---|---|---|---|
| 81 | 3-((R)-(4-chlorophenyl){3-[(1R)-1-(3,5-difluorophenyl)-2-fluoro-2-methylpropyl]azetidin-1-yl}methyl)benzonitrile | 4-Cl-C6H4 | 3-CN-C6H4 | 469 (M+1, $^{35}$Cl) and 471 (M+1, $^{37}$Cl) |

| Example | Name3 | Ar | R4 | Mass Spectrum m/e |
|---|---|---|---|---|
| 82 | 3-((S)-(4-chlorophenyl){3-∂(1R)-1-(3,5-difluorophenyl)-2-fluoro-2-methylpropyl]azetidin-1-yl}methyl)benzonitrile | —C6H4—Cl | —C6H4—CN | 469 (M+1, 35Cl) and 471 (M+1, 37Cl) |
| 83 | 3-{{3-[1-(3,5-difluorophenyl)-2-fluoro-2-methylpropyl]azetidin-1-yl}[4-(trifluoromethyl)phenyl] meethyl}benzonitrile | —C6H4—CF3 | —C6H4—CN | 502 (M+1) |
| 84 | 3-{(R)-{3-[(1S)-1-(3,5-difluorophenyl)-2-fluoro-2-methylpropyl]azetidin-1-yl}[4-(trifluoromethyl)phenyl]methyl} benzonitrile | —C6H4—CF3 | —C6H4—CN | 502 (M+1) |
| 85 | 3-{(S)-{3-[(1S)-1-(3,5-difluorophenyl)-2-fluoro-2-methylpropyl]azetidin-1-yl}[4-(trifluoromethyl)phenyl]methyl} benzonitrile | —C6H4—CF3 | —C6H4—CN | 502 (M+1) |
| 86 | 3-[1-(3,5-difluorophenyl)-2-fluoro-2-methylpropyl]-1-(dipheenylmethyl)azetidine | —C6H5 | —C6H5 | 410 (M+1) |
| 87 | 3-[(1R)-1-(3,5-difluorophenyl)-2-fluoro-2-methylpropyl]-1-(diphenylmethyl)azetidine | —C6H5 | —C6H5 | 410 (M+1) |
| 88 | 3-[(1S)-1-(3,5-difluorophenyl)-2-fluoro-2-methylpropyl]-1-(diphenylmethyl)azetidine | —C6H5 | —C6H5 | 410 (M+1) |
| 89 | 3-((R)-(4-chloro-3-iodophenyl){3-[(1S)-1-(3,5-difluorophenyl)-2-fluoro-2-methylpropyl]azetidin-1-yl}methyl)benzonitrile | —C6H3(Cl)(I) | —C6H4—CN | 595 (M+1) |
| 90 | 3-((4-cyanophenyl){3-[1-(3,5-difluorophenyl)-2-fluoro-2-methylpropyl]azetidin-1-yl}methyl)benzonitrile | —C6H4—CN | —C6H4—CN | 460 (M+1) |
| 91 | 3-((S)-(4-cyanophenyl){3-[(1S)-1-(3,5-difluorophenyl)-2-fluoro-2-methylpropyl]azetidin-1-yl}methyl)benzonitrile | —C6H4—CN | —C6H4—CN | 460 (M+1) |
| 92 | 3-((R)-(4-cyanophenyl){3-[(1S)-1-(3,5-difluorophenyl)-2-fluoro-2-methylpropyl]azetidin-1-yl}methyl)benzonitrile | —C6H4—CN | —C6H4—CN | 460 (M+1) |

-continued

| Example | Name3 | Ar | R4 | Mass Spectrum m/e |
|---|---|---|---|---|
| 93 | 3-((S)-(4-cyanophenyl){3-[(1R)-1-(3,5-difluorophenyl)-2-fluoro-2-methylpropyl]azetidin-1-yl}methyl)benzonitrile | 4-CN-C6H4- | 3-CN-C6H4- | 460 (M+1) |
| 94 | 3-((R)-(4-cyanophenyl){3-[(1R)-1-(3,5-difluorophenyl)-2-fluoro-2-methylpropyl]azetidin-1-yl}mthyl)benzonnitrile | 4-CN-C6H4- | 3-CN-C6H4- | 460 (M+1) |
| 95 | 4-((3-bromophenyl){3-[1-(3,5-difluorophenyl)-2-fluoro-2-methylpropyl]azetidin-1-yl}methyl)benzonitrile | 4-Br-C6H4- | 3-CN-C6H4- | 513 (M+1, $^{79}$Br), 515 (M+1, $^{81}$Br) |
| 96 | 3-{(R)-{3-[(1S)-1-(3,5-difluorophenyl)-2-fluoro-2-methylpropyl]azetidin-1-yl}[3-(methylsulfonyl)phenyl]methyl}benzonitrile | 3-SO2CH3-C6H4- | 3-CN-C6H4- | 513 (M+1) |
| 97 | 3-{(S)-{3-[(1S)-1-(3,5-difluorophenyl)-2-fluoro-2-methylpropyl]azetidin-1-yl}[3-(methylsulfonyl)phenyl]methyl}benzonitrile | 3-SO2CH3-C6H4- | 3-CN-C6H4- | 513 (M+1) |
| 98 | 2-chloro-5-((4-chlorophenyl){3-[1-(3,5-difluorophenyl)-2-fluoro-2-methylpropyl]azetidin-1-yl}methyl)pyridine | 4-Cl-C6H4- | 2-Cl-pyridin-5-yl | 479 (M+1 $^{35}$Cl, $^{35}$Cl); 481 (M+1 $^{35}$Cl, $^{37}$Cl) |
| 99 | 1-{(4-chlorophenyl)[3-(methylsulfonyl)phenyl]methyl}-3-[1-(3,5-difluorophenyl)-2-fluoro-2-methylpropyl]azetidine | 4-Cl-C6H4- | 3-SO2CH3-C6H4- | 522 (M+1, $^{35}$Cl) and 524 (M+1, $^{37}$Cl) |
| 100 | 3-((6-chloropyridin-3-yl){3-[1-(3,5-difluorophenyl)-2-fluoro-2-methylpropyl]azetidin-1-yl}methyl)benzonitrile | 6-Cl-pyridin-3-yl | 3-CN-C6H4- | 470 (M+1, $^{35}$Cl) and 472 (M+1, $^{37}$Cl) |
| 101 | 4-((4-chlorophenyl){3-[1-(3,5-difluorophenyl)-2-fluoro-2-methylpropyl]azetidin-1-yl}methyl)-2-meethylpyridine | 4-Cl-C6H4- | 2-Cl-pyridin-4-yl | 479 (M+1 $^{35}$Cl, $^{35}$Cl); 481 (M+1 $^{35}$Cl, $^{37}$Cl) |
| 102 | N-[3-((4-chlorophenyl){3-[1-(3,5-difluorophenyl)-2-fluoro-2-methylpropyl]azetidin-1-yl}methyl)phenyl]methanesulfonamide | 4-Cl-C6H4- | 3-NHSO2Cl-C6H4- | 537 (M+1, $^{35}$Cl) and 539 (M+1, $^{37}$Cl) |

-continued

| Example | Name3 | Ar | R4 | Mass Spectrum m/e |
|---|---|---|---|---|
| 103 | N-[3-((4-chlorophenyl){3-[1-(3,5-difluorophenyl)-2-fluoro-2-methylpropyl]azetidin-1-yl}methyl)phenyl]methanesulfonamide | 4-Cl-C6H4- | 3-(CH3SO2NH)-C6H4- | 551 (M+1, 35Cl) and 551 (M+1, 37Cl) |
| 104 | 3-[{3-[1-(3,5-difluorophenyl)-2-fluoro-2-methylpropyl]azetidin-1-yl}(4-fluorophenyl)methyl]benzonitrile | 4-F-C6H4- | 3-CN-C6H4- | 453 (M+1) |
| 105 | 5-chloro-2-((4-chlorophenyl){3-[1-(3,5-difluorophenyl)-2-fluoro-2-methylpropyl]azetidin-1-yl}methyl)pyridine | 4-Cl-C6H4- | 5-Cl-pyridin-2-yl | 479 (M+1 35Cl, 35Cl); 481 (M+1 35Cl, 37Cl) |
| 106 | 1-[(4-bromo-2-thienyl)(4-chlorophenyl)methyl]-3-[1-(3,5-difluorophenyl)-2-fluoro-2-methylpropyl]azetidine | 4-Cl-C6H4- | 4-Br-thien-2-yl | 528 (M+1, 79Br), 530 (M+1, 81Br) |
| 107 | 5-((4-chlorophenyl)-{3-[1-(3,5-difluorophenyl)-2-fluoro-2-methylpropyl]azetidin-1-yl}mthyl)thiophene-3-carbonitrile | 4-Cl-C6H4- | 4-CN-thien-2-yl | 528 (M+1, 35Cl, 79Br), 530 (M+1, 35Cl, 81Br and 37Cl, 79br), 532 (M+1, 37Cl, 81Br) |
| 108 | 3-[{3-[1-(3,5-difluorophenyl)-2-fluoro-2-methylpropyl]azetidin-1-yl}(4-methylphenyl)methyl]benzonitrile | 4-CH3-C6H4- | 3-CN-C6H4- | 449 (M+1) |

EXAMPLE 109

1-{1-[bis(4-chlorophenyl)methyl]azetidin-3-yl}-1-3,5-difluorophenyl)-2,2-dimethylpropan-1-ol

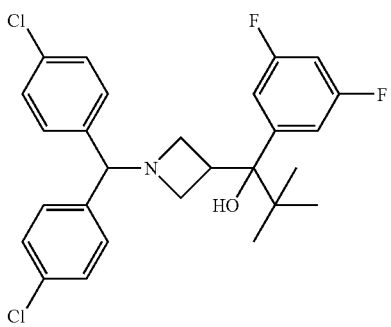

To a solution of 120 mg (0.278 mmol) of {1-[bis(4-chlorophenyl)methyl]azetidin-3-yl}(3,5-difluorophenyl)methanone (Example 19, Step 4) in 3 mL of THF, 0.35 mL (0.69 mmol) of tert-butyl magnesium chloride (2M in THF) was added and stirred for 1 h at −78° C. Then to the reaction mixture was added 30 mL of ether and 5 mL of 7 mL of qNaHCO3. The pH was adjusted to 8-9 with 2N NaOH. The water layer was extracted with $CH_2Cl_2$ (3×30 mL). The combined organic layer was dried over $Na_2SO_4$ and concentrated. The residue was purified by silica gel chromatography with hexanes/ethyl acetate to afford of the title compound as a white solid; $^1$H-NMR(CDCl$_3$) δ 0.88 (s, 9H), 2.46 (t, J=7.2 Hz, 1H), 2.97 (s, 1H), 3.05 (t, J=7.6 Hz, 1H), 3.31-3.39 (m, 2H), 3.42 (m, 1H), 4.25 (s, 1H), 6.56 (m, 2H), 6.68 (m, 1H), 7.24-7.36 (m, 8H); Mass Spectrum: m/e=490 (M+1 $^{35}$Cl, $^{35}$Cl) and 492 (M+1 $^{35}$Cl, $^{37}$Cl).

EXAMPLE 110

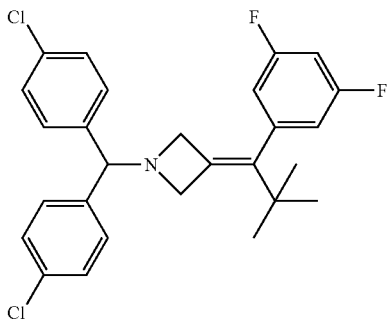

1-[bis(4-chlorophenyl)methyl]-3-[1-(3,5-difluorophenyl)-2,2-dimethylpropylidene]azetidine To a solution of 80 mg (0.163 mmol) of 1-{1-[bis(4-chlorophenyl)methyl]azetidin-3-yl}-1-(3,5-difluorophenyl)-2,2-dimethylpropan-1-ol (2) in 1 mL of $CH_2Cl_2$, 86 uL (0.653 mmol) of DAST was added and it was stirred for 1 h at −78° C. and overnight at rt. Then another 86 uL (0.653 mmol) of DAST was added again and it was stirred 3 h at 38-45° C. Then to the reaction mixture was added 20 mL of $CH_2Cl_2$ and 10 mL of aq $NaHCO_3$. The pH was adjusted to 8-9 with 2N NaOH. The water layer was extracted with $CH_2Cl_2$ (3×20 mL). The combined organic layer was dried over $Na_2SO_4$ and concentrated. The residue was purified by silica gel chromatography with hexanes/ethyl acetate to afford the title compound as a white solid; $^1$H-NMR(CDCl$_3$) δ 1.06 (s, 9R), 3.37 (s, 2H), 4.05 (s, 2H), 4.44 (s, 1H), 6.55 (d, J=8 Hz, 2H), 6.67 (m, 1H), 7.25 (d, J=6.6 Hz, 4H), 7.33 (d, J=7 Hz, 4H); Mass Spectrum: m/e=472 (M+1 $^{35}$Cl, $^{35}$Cl) and 474 (M+1 $^{35}$Cl, $^{37}$Cl).

EXAMPLE 111

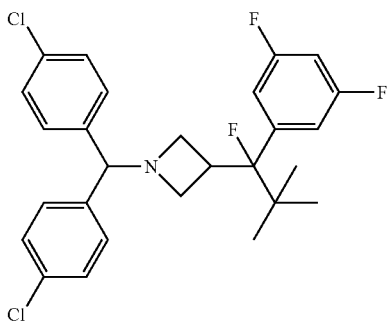

1-[bis(4-chlorophenyl)methyl]-3-[1-(3,5-difluorophenyl)-1-fluoro-2,2-dimethylpropyl]azetidine Further elution of the column in Example 110 afforded the title compound as a white solid; $^1$H-NMR(CDCl$_3$) δ 0.895 (s, 9H), 2.39 (m, 1H), 2.99 (m, 2H), 3.38 (m, 2H), 4.24 (s, 1H), 6.68 (m, 2H), 6.93 (m, 2H), 7.20-7.35 (m, 8H); Mass Spectrum: m/e=492 (M+1 $^{35}$Cl, $^{35}$Cl) and 494 (M+1 $^{35}$Cl, $^{37}$Cl).

EXAMPLE 112

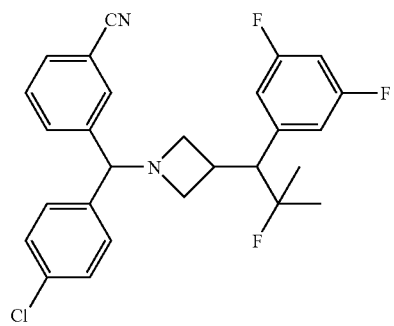

1-{1-[(3-chlorophenyl)(4-chlorophenyl)methyl]azetidin-3-yl}-1-(3,5-difluorophenyl)-2-methylpropan-2-ol To a solution of 175 mg (0.368 mmol) of 1-{1-[bis(4-chlorophenyl)methyl]azetidin-3-yl}-1-(3,5-difluorophenyl)-2-methylpropan-2-ol (1) in 3 mL of $CH_2Cl_2$, 1 mL of hydrogen fluoride-pyridine was added. The reaction was stirred for 9 h at 42° C. Then the reaction mixture was poured to 7 mL of 5N NaOH, 7 mL of aq $NaHCO_3$ and 30 mL of $CH_2Cl_2$. The pH was adjusted to 8-9 with 2N NaOH. The water layer was extracted with $CH_2Cl_2$ (3×30 mL). The combined organic layer was dried over $Na_2SO_4$ and concentrated. The residue was purified by silica gel chromatography with hexanes/methyl tert-butyl ether to afford the title compound as a white solid; $^1$NMR(CDCl$_3$) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.20 (s, 1H), 6.68-6.71 (m, 3H), 7.21-7.33 (m, 8H); Mass Spectrum: m/e=478 (M+1 $^{35}$Cl, $^{35}$Cl) and 480 (M+1 $^{35}$Cl, $^{37}$Cl).

EXAMPLE 113

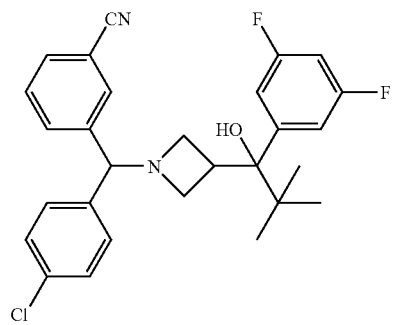

3-((4-chlorophenyl){3-[1-(3,5-difluorophenyl)-1-hydroxy-2,2-dimethylpropyl]azetidin-1-yl}methyl)benzonitrile Step 1 tert-butyl 3-[1-(3,5-difluorophenyl)-1-hydroxy-2,2-diethylpropyl]azetidine-1-carboxylate To a solution of 3.07 g (10.34 mmol) of tert-butyl 3-(3,5-difluorobenzoyl)azetidine-1-carboxylate in 20 mL of THF, 36.19 mL (36.19 mmol) of tert-butyl magnesium chloride was added and stirred for 3.5 h at −78° C. To the solution was added 8 mL of aq. NH$_4$Cl and the solution was filtered to remove the solid. The filtrate was washed with ether. The combined organic layer was concentrated to remove solvents and residue was purified by silica gel chromatography with hexanes/ethyl acetate to afford the title compound; $^1$H-NMR (CDCl$_3$) δ 0.897 (s, 9H), 1.425 (s, 9H), 2.234(br, 1H), 3.25 (m, 1H), 3.55 (m, 1H), 3.71 (t, J=8.9 Hz, 1H), 3.97 (t, J=8.4 Hz, 1H), 4.17(m ,1H), 6.53-6.74 (m, 3H).

Step 2 1-azetidin-3-yl-1-(3,5-difluorophenyl)-2,2-dimethylpropan-1-ol

To a solution of 210 mg (0.59 mmol) of tert-butyl 3-[1-(3,5-difluorophenyl)-1-hydroxy-2,2-dimethylpropyl]azetidine-1-carboxylate (2) in 1 mL of CH$_2$Cl$_2$, 1.5 mL of TFA was added and the solution was stirred for 1 h at rt. It was concentrated and washed with ether to afford the title compound as white solid; Mass Spectrum: m/e=256 (M+1).

Step 3 3-((4-chlorophenyl){3-[1-(3,5-difluorophenyl)-1-hydroxy-2,2-dimethylpropyl]azetidin-1-yl}methyl)benzonitrile The reaction mixture of 135 mg (0.44 mmol) of 3-[bromo(4-chlorophenyl)methyl]benzonitrile, 105 mg (0.367 mmol) of 1-azetidin-3-yl-1-(3,5-difluorophenyl)-2,2-dimethylpropan-1-ol (3) and 230 uL (1.32 mmol) of N,N-diisopropylethylamine in 6 mL of acetonitrile was refluxed for 3 h. Then it was concentrated and the residue was dissolved in 5 mL of hexane/ether. 1 mL of 1N HCl in ether was added to above solution to make salt. It was filtered and washed with hexane/ether. The residue was neutralized with base and was purified by silica gel chromatography with hexanes/ethyl acetate to afford one racemic diastereomer of the title compound; Mass Spectrum: m/e=481 (M+1 $^{35}$Cl) and 483 (M+1 $^{37}$Cl). Further elution of the column afforded the other racemic diastereomer of the title compound; Mass Spectrum: m/e=481 (M+1 $^{35}$Cl) and 483 (M+1 $^{37}$Cl).

EXAMPLE 114

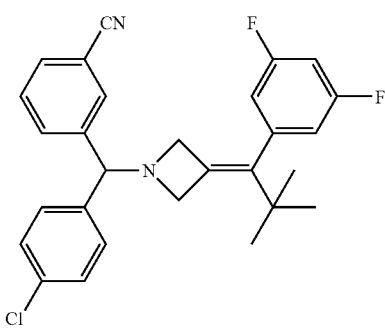

3-((4-chlorophenyl){3-[1-(3,5-difluorophenyl)-2,2-dimethylpropylidene]azetidin-1-yl}methyl) benzonitrile Step 1 tert-butyl 3-[1-(3,5-difluorophenyl)-2,2-dimethylpropylidene]azetidine-1-carboxylate To a solution of 1.72 g (4.84 mmol) of tert-butyl 3-[1-(3,5-difluorophenyl)-1-hydroxy-2,2-dimethylpropyl]azetidine-1-carboxylate (2) in 25 mL of CH$_2$Cl$_2$, 5.76 mL of DAST was added and stirred for 3 h at rt. Then it was poured into 50 mL of CH$_2$Cl$_2$, 25 mL of ag NaHCO$_3$ and 15 mL of 6N NaOH. It was adjusted to pH 8~9 with 2N NaOH. The water layer was extracted with CH$_2$Cl$_2$ (3×50 mL). The combined organic layer was dried over Na$_2$SO$_4$ and concentrated. The residue was purified by silica gel chromatography with hexanes/ethyl acetate to afford of the title compound (2) as a white solid; $^1$H-NMR(CDCl$_3$) δ 1.10 (s, 9H), 1.45 (s, 9H), 4.05 (t, J=2.8 Hz, 2H), 4.73(t, J=2.8 Hz, 2H), 6.60 (d, J=8 Hz, 2H), 6.74 (m, 1H).

Step 2 3-[1-(3,5-difluorophenyl)-2,2-dimethylpropylidene]azetidine

To a solution of 210 mg (0.623 mmol) of tert-butyl 3-[1-(3,5-difluorophenyl)-2,2-dimethylpropylidene]azetidine-1-carboxylate in 1 mL of CH$_2$Cl$_2$, was added 1.5 mL of TFA followed by stirring for 1 h at rt. The reaction mixture was concentrated and washed with ether to afford the title compound as white solid; Mass Spectrum: m/e=238 (M+1).

Step 3 3-((4-chlorophenyl){3-[1-(3,5-difluorophenyl)-2,2-dimethylpropylidene]azetidin-1-yl}methyl) benzonitrile A mixture of 99 mg (0.32 mmol) of 3-[bromo(4-chlorophenyl)methyl]benzonitrile, 80 mg (0.216 mmol) of 3-[1-3,5-difluorophenyl)-2,2-dimethylpropylidene]azetidine and 113 uL (0.65 mmol) of N,N-diisopropylethylamine in 3 mL of acetonitrile was heated at reflux for 3 h. Then the reaction was concentrated and the residue was dissolved in 5 mL of hexane/ether. A solution of 1 mL of 1N HCl in ether was added to above solution to make the salt. The mixture was filtered and the solids were washed with hexane/ether. The residue was neutralized with NaOH and the free base was purified by silica gel chromatography with hexanes/ethyl acetate to afford the title compound as a white solid; $^1$H-NMR(CDCl$_3$) δ 1.07 (s, 9H), 3.37 (m, 2H), 4.06 (m, 2H), 4.50 (s, 1H), 6.58 (d, J=8 Hz, 2H), 6.74 (m, 1H), 7.28 (d, J=8.5 Hz, 2H), 7.34 (d, J=8.5 Hz, 2H), 7.39 (t, J=7.7 Hz, 1H), 7.50(d, J=7.8 Hz, 1H), 7.62 (d, J=7.8 Hz, 1H), 7.72 (s, 1H); Mass Spectrum: m/e=463 (M+1 ³⁵Cl) and 465 (M+1 ³⁷Cl).

EXAMPLE 115

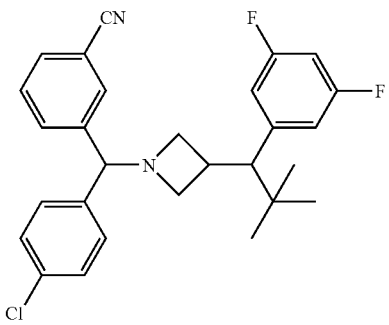

3-((4-chlorophenyl){3-[1-(3,5-difluorophenyl)-2,2-dimethylpropyl]azetidin-1-yl}methyl)benzonitrile Step 1 tert-butyl 3-[1-(3,5-difluorophenyl)-2,2-dimethylpropyl]azetidine-1-carboxylate A mixture of 720 mg (2.14 mmol) of tert-butyl 3-[1-(3,5-difluorophenyl)-2,2-dimethylpropylidene]azetidine-1-carboxylate and 600 mg of palladium on activated carbon (10%) in 6 mL of ethyl acetate and 5 mL of MeOH was pressurized to 50 psi with hydrogen gas at room temperature for 72 h. The solution was filtered through CELITE and the filtrate was concentrated. The residue was purified by silica gel chromatography with hexanes/ethyl acetate to afford the title compound as a white solid; $^1$H-NMR(CDCl$_3$) δ 0.88 (s, 9H), 1.43 (s, 9H), 2.69 (d, J=11 Hz, 1H), 3.09-3.18 (m, 2H), 3.71 (t, J=8.2 Hz, 1H), 3.81(m, 1H), 4.12 (t, J=8.5 Hz, 1H), 6.49 (br, 1H), 6.69 (m, 2);

Step 2 3-[1-(3,5-difluorophenyl)-2,2-dimethylpropyl]azetidine

To a solution of 360 mg (1.06 mmol) of tert-butyl 3-[1-(3, 5-difluorophenyl)-2,2-dimethylpropyl]azetidine-1-carboxylate in 1.5 mL of CH$_2$Cl$_2$, was added 1.5 mL of TFA and the solution was stirred for 1 h at rt. It was concentrated and washed with ether to afford the title compound as a white solid; Mass Spectrum: m/e=240 (M+1).

Step 3 3-((4-chlorophenyl){3-[1-(3,5-difluorophenyl)-2,2-dimethylpropyl]azetidin-1-yl}methyl)benzonitrile A mixture of 263 mg (0.86 mmol) of 3-[bromo(4-chlorophenyl)methyl]benzonitrile, 213 mg (0.574 mmol) of 3-[1-(3,5-difluorophenyl)-2,2-dimethylpropyl]azetidine and 300 uL (1.72 mmol) of N,N-diisopropylethylamine in 6 mL of acetonitrile was heated to reflux for 3 h. Then the solution was concentrated and the residue was dissolved in 5 mL of hexane/ether. 1.5 mL of 1N HCl in ether was added to above solution to make salt. It was filtered and washed with hexane/ether. The residue was neutralized with base and was purified by silica gel chromatography with hexanes/ethyl acetate to afford one racemic diastereomer of the title compound; Mass Spectrum: m/e=465 (M+1 ³⁵Cl) and 467 (M+1 ³⁷Cl).

Further elution of the column afforded the other racemic diastereomer of the title compound; Mass Spectrum: m/e=465 (M+1 ³⁵Cl) and 467 (M+1 ³⁷Cl).

EXAMPLE 116

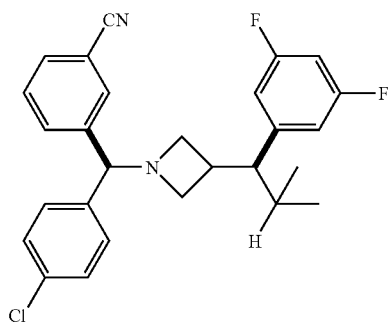

3-((S)-4-chlorophenyl){3-[(1S)-1-(3,5-difluorophenyl)-2-methylpropyl]azetidin-1-yl}methyl)benzonitrile Step 1 (1S)-1-3,5-difluorophenyl)-1-[1-(diphenylmethyl)azetidin-3-yl]acetone Racemic 1-(3,5-difluorophenyl)-1-[1-(diphenylmethyl)azetidin-3-yl]acetone (Prepared as described in Example 2) was separated into its two component enantiomers by chromatography on a ChiralPak OD column using 1.5% isopropanol-heptane eluant. The slower eluting enantiomer was the (+)(S) diastereomer. This material was taken directly in the next step.

Step 2 3-[(1R)-1-(3,5-(difluorophenyl)-2-methylprop-2-en-1-yl]-1-(diphenylmethyl)azetidine A suspension of 1.08 g (3 mmole) of methyltriphenylphosphonium bromide in dry THF was cooled to −78° C. under N$_2$. To this was added 1.4 mL of a 1.6 M solution of butyllithium in hexane and the solution was stirred at room temperature for 30 minutes. Then a solution of 0.285 g (0.73 mmole) of (1S)-1-(3,5-difluorophenyl)-1-[1-(diphenylmethyl)azetidin-3-yl]acetone in 2 mL THF was added and the solution was stirred for 2 h at −78° C. before being allowed to warm to −10° C. The reaction was quenched by addition of 10 mL aqueous saturated NH$_4$Cl solution and diluted with 25 mL ether. The layers were separated and the aqueous layer was washed with three 20 mL portions of ether and the combined organic extracts were washed with brind, dried over Na$_2$SO$_4$ and concentrated to afford the title compound as a clear oil; Mass Spectrum: m/e=390 (M+1).

Step 3 3-[(1S)-1-(3,5-difluorophenyl)-2-methylpropyl]azetidine

A mixture of 250 mg (0.64 mmole) of 3-[(1R)-1-(3,5-difluorophenyl)-2-methylprop-2-en-1-yl]-1-(diphenylmethyl)azetidine and 50 mg of 10% Pd/C in 10 mL methanol and 2 mL of 1M HCl in ether was shaken under 40 psi H$_2$. After 8 h, the solution was filtered and the filtrate was concentrated. The residue was triturated with hexane to remove diphenylmethane and the residue was collected to afford the title compound as a white solid; Mass Spectrum m/e=226 (M+1)

Step 4 3-((S)(4-chlorophenyl){3-[(1S)-1-(3,5-difluo-rophenyl)-2-methylpropyl]azetidin-1-yl}methyl) benzonitrile A mixture of 106 mg (0.5 mmole) of 3-[(1S)-1-(3,5-difluorophenyl)-2-methylpropyl]azetidine hydrochloride from Step 3 and 0.650 g (2 mmole) of $Cs_2CO_3$ in 5 mL dry acetonitrile was stirred at rt in a flask fitted with a small Dean-Stark trap. After 15 minutes, 0.306 g (1 mmole) of 3-[bromo(4-chlorophenyl)methyl]benzonitrile was added and the mixture was heated at 60° C. After 18 h, the solution was partitioned between ethyl acetate and water. The layers were separated and the organic layer was dried over $Na_2SO_4$. The solution was filtered and the filtrate was concentrated to an oil. The residue was purified by chromatography on a ChralPak AD column using 4% isopropanol-heptane to afford two enantiomers. Fractions containing the slower product diastereomer were pooled and concentrated to afford the title compound; Mass Spectrum: m/e=451 (M+1, $^{35}Cl$) and 453 (M+1, 37Cl).

EXAMPLE 117

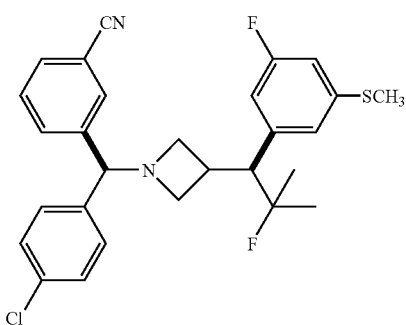

3-[(S)-(4-chlorophenyl)(3-{(1S)-2-fluoro-1-[3-fluoro-5-(methylthio)phenyl]-2-methylpropyl}azetidin-1-yl)methyl]benzonitrile Step 1 3-[(1S)-1-(3,5-difluorophenyl-2-fluoro-2-methylpropyl]-1-(diphenylmethyl)azetidine A mixture of 0.408 mg (1.0 mmole) of 3-[(1S)-1-(3,5-difluorophenyl)-2-fluoro-2-methylpropyl]-1-(diphenylmethyl)azetidine and 90 mg (1.3 mmole) of $NaSCH_3$ in 2 mL of dry DMF was degassed with $N_2$. After 15 minutes, the solution was heated at 110° C. under $N_2$. After 20 minutes, the solution was cooled, partitioned between 100 mL ether and 10 mL 1M NaOH and the aqueous layer was washed with two 50 mL portions of ether. The combined organic extracts were washed with brine, dried over $MgSO_4$ and concentrated. The residue was filtered through silica gel using 10% ethyl acetate-hexane to afford the title compound; Mass Spectrum: m/e=438 (M+1).

Step 2 3-{(1S)-2-fluoro-1-[3-fluoro-5-(methylthio) phenyl]-2-methylpropyl}azetidine The benzohydrol group of 0.431 g (0.95 mmole) of 3-[(1S)-1-(3,5-difluorophenyl)-2-fluoro-2-methylpropyl]-1-diphenylmethyl)azetidine was removed by reaction with 0.3 mL of 1-chloroethyl chloroformate in 5 mL of dry THF as described in Step 1 of Example 79 to afford the title compound; Mass Spectrum: m/e=272 (M+1).

Step 3 3-[(S)-(4-chlorophenyl)(3-{(1S)-2-fluoro-1-[3-fluoro-5-(methylthio)phenyl]-2-methylpropyl}azetidin-1-yl)methyl]benzonitrile A sample of 0.233 mg (0.86 mmole) of 3-{(1S)-2-fluoro-1-[3-fluoro-5-(methylthio)phenyl]-2-methylpropyl}azetidine was alkylated with 263 mg (0.86 mmole) of 3-[bromo(4-chlorophenyl)methyl]benzonitrile and 0.975 mg (3 mmole) of $Cs_2CO_3$ as described in Step 2 of Example 79 to afford the title compound; Mass Spectrum: m/e=497 (M+1, $^{35}Cl$); 499 (M+1, $^{37}Cl$)

EXAMPLE 118

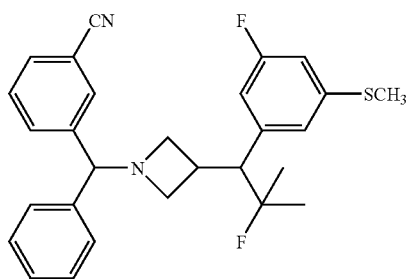

3-[(R)-(4-chlorophenyl)(3-{(1S)-2-fluoro-1-[3-fluoro-5-(methylthio)phenyl]-2-methylpropyl}azetidin-1-yl)methyl]benzonitrile Further elution of the column from Step 3 of example 117 afforded the title compound; Mass Spectrum: m/e=497 (M+1).

EXAMPLES 119-120

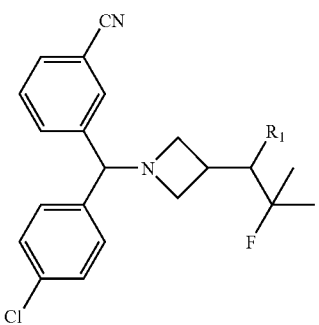

The following examples were prepared as described in Example 117 except that the potassium salt of the thiols were used in Step 1 instead of the sodium salts.

| Example | Name | R1 | Mass Spectrum m/e |
|---|---|---|---|
| 119 | 3-[(S)-(4-chlorophenyl)(3-{(1S)-1-[3-(ethylthio)-5-fluorophenyl]-2-fluoro-2-methylpropyl}azetidin-1-yl)methyl]benzonitrile | (F, SEt substituted phenyl) | 511 (M+1, $^{35}$Cl); 513 (M+1, $^{37}$Cl) |
| 120 | 3-[(S)-(4-chlorophenyl)(3-{(1S)-2-fluoro-1-[3-fluoro-5-(isopropylthio)phenyl]-2-methylpropyl}azetidin-1-yl)methyl]benzonitrile | (F, SiPr substituted phenyl) | 525 (M+1, $^{35}$Cl); 527 (M+1, $^{37}$Cl) |

EXAMPLE 121

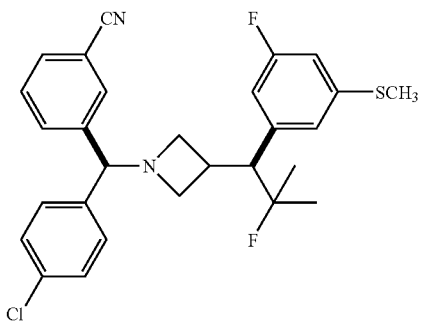

h3-[(S)-(4-chlorophenyl)(3-{(1S)-2-fluoro-1-[3-fluoro-5-(methylthio)phenyl]-2-methylpropyl}azetidin-1-yl)methyl]benzonitrile To a solution of 80 mg (0.16 mmole) of 3-[(S)-(4-chlorophenyl)(3-{(1S)-2-fluoro-1-[3-fluoro-5-(methylthio)phenyl]-2-methylpropyl}azetidin-1-yl)methyl]benzonitrile in 2 mL dichloromethane was added 0.2 mL of a 1M solution of methanesulfonic acid in dichloromethane. The solution was allowed to stir for 5 minutes, and then 95 mg (0.36 mmole) of 3-chloroperbenzoic acid (70%) was added and the solution was allowed to stir at rt. After 30 minutes, the solution was diluted with 25 mL ether and the organic layer was washed with three 10 mL portions of 1M NaOH. The aqueous layers were sequentially back-extracted with ether and the combined organic extracts were washed with brine, dried over MgSO4 and concentrated. The residue was filtered through silica gel using a 15 mL funnel column and 20% ethyl acetate-hexane to afford the title compound; Mass Spectrum: m/e=529 (M+1, $^{35}$Cl); 531 (M+1, $^{37}$Cl).

EXAMPLE 122

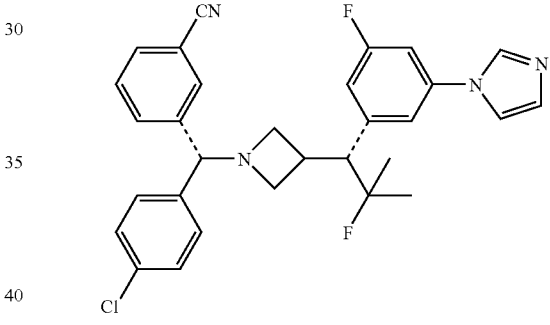

3-[(R)-(4-chlorophenyl)(3-{(1R)-2-fluoro-1-[3-fluoro-5-(1H-imidazol-1-yl)phenyl]-2-methylpropyl}azetidin-1-yl)methyl]benzonitrile A mixture of 90 mg (0.192 mmole) of 3-((R)-(4-chlorophenyl){3-[(1R)-1-(3,5-difluorophenyl)-2-fluoro-2-methylpropyl]azetidin-1-yl}methyl)benzonitrile, 17 mg (0.25 mmole) of imidazole and 40 mg (0.288 mmole) of $K_2CO_{3\ 1\ in}$ 1.5 mL DMSO was stirred at 150° C. in a microwave (with cooling). After 4 h, the mixture was poured into 30 mL of ether and 5 mL of water. The layers were separated and the aqueous layer was washed with three 10 mL portions of ether and the combined organic extracts were washed with brine, dried over Na$_2$SO$_4$ and concentrated. The residue was purified by flash chromatography using 25% acetone-hexane to afford the title compound; Mass Spectrum: m/e=517 (M+1, $^{35}$Cl); 519 (M+1, $^{37}$Cl).

EXAMPLES 123-125

The following Examples were prepared from 3-((S)-(4-chlorophenyl){3-[(1S)-1-(3,5-difluorophenyl)-2-fluoro-2-methylpropyl]azetidin-1-yl}methyl)benzonitrile using the appropriate base (e.g. 1,2,4-triazole, imidazole or azetidine) according to the procedure described in Example 122.

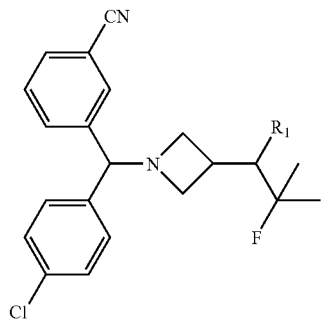

| Example | Name | R₁ | Mass Spectrum m/e |
|---|---|---|---|
| 123 | 3-[(S)-(4-chlorophenyl)(3-{(1S)-2-fluoro-1-[3-fluoro-5-(1H-imidazol-1-yl)phenyl]-2-methylpropyl}azetidin-1-yl)methyl]benzonitrile | | 517 (M+1, ³⁵Cl); 519 (M+1, ³⁷Cl) |
| 124 | 3-[(S)-(4-chlorophenyl)(3-{(1S)-2-fluoro-1-[3-fluoro-5-(1H-1,2,4-triazol-1-yl)phenyl]-2-methylpropyl}azetidin-1-yl)methyl]benzonitrile | | 518 (M+1, ³⁵Cl); 520 (M+1, ³⁷Cl) |
| 125 | 3-[(S)-{3-[(1S)-1-(3-azetidin-1-yl-5-fluorophenyl)-2-fluoro-2-methylpropyl]azetidin-1-yl}(4-chlorophenyl)meethyl]benzonitrile | | 506 (M+1, ³⁵Cl); 509 (M+1, ³⁷Cl) |

EXAMPLE 126

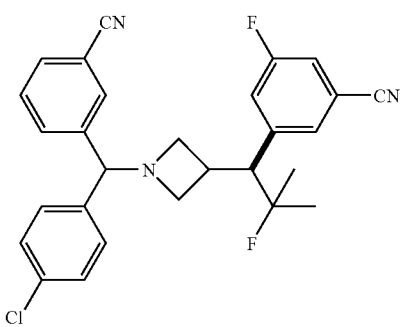

3-((1S)-1-{1-[(S)-(4-chlorophenyl)(3-cyanophenyl)methyl]azetidin-3-yl}-2-fluoro-2-methylpropyl)-5-fluorobenzonitrile Step 1 Ethyl (2R)-(3-bromo-5-fluorophenyl)[1-(diphenylmethyl)-3-hydroxyazetidin-3-yl]acetate The title compound was prepared from ethyl 3-bromo-5-fluorophenylacetate and 1-[bis-phenylmethyl]azetidin-3-one (Preparation 2) by the procedure described in Step 2 of Preparation 3 except that lithium hexamethyldisilamide was used instead of butyllithium to form the ketene acetal; Mass Spectrum: m/e=498 (M+1, ⁷⁹Br), 500 (M+1, ⁸¹Br)

Step 2 Ethyl (3-bromo-5-fluorophenyl)[1-(diphenylmethyl)azetidin-3-ylidene]acetate The title compound was prepared from ethyl (2R)-(3-bromo-5-fluorophenyl)[1(diphenylmethyl)-3-hydroxyazetidin-3-yl]acetate according to the procedures described in Preparation 5; Mass Spectrum: m/e=480 (M+1, $^{79}$Br), 482 (M+1, $^{81}$Br)

Step 3 Ethyl (3-bromo-5-fluorophenyl)[1-(diphenylmethyl)azetidin-3-yl]acetate The title compound was prepared from ethyl (3-bromo-5-fluorophenyl)[1-(diphenylmethyl)azetidin-3-ylidene]acetate according to the procedure described in Preparation 6 except that THF was used as the co-solvent; Mass Spectrum m/e=482 (M+1, $^{79}$Br), 484 (M+1, $^{81}$Br).

Step 4 1-(3-Bromo-5-fluorophenyl)-1-[1-(diphenylmethyl)azetidin-3-yl]-2-methylpropan-2-ol The title compound was prepared from ethyl (3-bromo-5-fluorophenyl)[1-(diphenylmethyl)azetidin-3-yl]acetate according to the procedure described in Step 1 of Example 49; Mass Spectrum: m/e=468 (M+1, $^{79}$Br), 470 (M+1, $^{81}$Br).

Step 5 (1S)-1-(3-bromo-5-fluorophenyl)-1-[1-(diphenylmethyl)azetidin-3-yl]-2-methylpropan-2-ol The enantiomers of the product of Step 4 were separated by chromatography on a ChiralPak AD column using 3% isopropanol-heptate as described in Step 1 of Example 49; Mass Spectrum: m/e=468 (M+1).

Step 6 3-[(1S)-1-(3-bromo-5-fluorophenyl)-2-fluoro-2-methylpropyl]-1-(diphenylmethyl)azetidine The title compound was prepared from (1S)-1-(3-bromo-5-fluorophenyl)-1-[1-(diphenylmethyl)azetidin-3-yl]-2-methylpropan-2-ol according to the procedure described in Step 2 of Example 76; Mass Spectrum: m/e=470 (M+1, $^{79}$Br), 472 (M+1, $^{81}$Br).

Step 7 3-[(1S)-1-(3-bromo-5-fluorophenyl)-2-fluoro-2-methylpropyl]azetidine

The title compound was prepared from 3-[(1S)-1-(3-bromo-5-fluorophenyl)-2-fluoro-2-methylpropyl]-1-(diphenylmethyl)azetidine according to the procedure described in Step 1 of Example 79; Mass Spectrum: m/e=304 (M+1, $^{79}$Br), 306 (M+1, $^{81}$Br).

Step 8 3-[(S)-{3-[(1S)-1-(3-Bromo-5-fluorophenyl)-2-fluoro-2-methylpropyl]azetidin-1-yl}(4-chlorophenyl)methyl]benzonitrile The title compound was prepared from 3-[(1S)-1-(3-bromo-5-fluorophenyl)-2-fluoro-2-methylpropyl]azetidine according to the procedure described in Step 2 of Example 79 except that diisopropylethylamine was used instead of $Cs_2CO_3$; Mass Spectrum: m/e=529 (M+1, $^{35}$Cl, $^{79}$Br), 531 (M+1, $^{35}$Cl, $^{81}$Br and $^{37}$Cl, $^{79}$Br), 576 (M+1, $^{35}$Cl, $^{81}$Br).

Step 9 3-((1S)-1-{1-[(S)-(4-chlorophenyl)(3-cyanophenyl)methyl]azetidin-3-yl}-2-fluoro-2-methylpropyl)-5-fluorobenzonitrile A suspension of 143 mg (0.27 mmole) of 3-[(S)-{3-[(1S)-1-(3-bromo-5-fluorophenyl)-2-fluoro-2-methylpropyl]azetidin-1-yl}(4-chlorophenyl)methyl]benzonitrile, 0.026 mg (0.216 mmole) of Zn(CN)2, 5 mg (0.005 mmole) of tris (dibenzylideneacetone)dipalladium(0) and 8 mg (0.014 mmole) of 1,1'-Bis(diphenylphosphino)ferrocene in 2.5 mL of dry DMF was degassed for 1 h at rt. Then the solution was heated at 140° C. for 17 h. The solution was concentrated under high vacuum and then was partitioned between 20 mL ether, 20 mL ethyl acetate and 10 mL water. The layers were separated and the aqueous layer was washed with two 20 mL portions of 1:1 ether-ethyl acetate. The combined organic layers were dried over $Na_2SO_4$ and concentrated. The residue was purified by preparatory TLC using 20% ethyl acetate-hexane to afford the title compound; Mass Spectrum: m/e=476 (M+1, $^{35}$Cl), 478 (M+1, $^{37}$Cl).

EXAMPLES 127-143

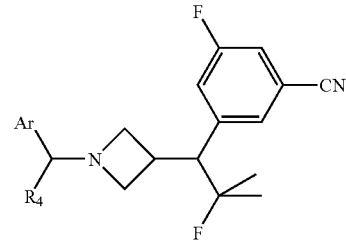

The following compounds were prepared according to the procedures described in Example 126.

| Example | Name | Ar | R4 | Mass Spectrum m/e |
|---|---|---|---|---|
| 127 | 3-(1-{1-[(4-chlorophenyl)(3-cyanophenyl)methyl]azetidin-3-yl}-2-fluoro-2-methylpropyl)-5-fluorobenzonitrile | —C$_6$H$_4$—Cl | —C$_6$H$_4$—CN | 476 (M+1, $^{335}$Cl), 478 (M+1, $^{37}$Cl). |
| 128 | 3-((1R)-1-{1-[(R)-(4-chlorophenyl)(3-cyanophenyl)methyl]azetidin-3-yl}-2-fluoro-2-methylpropyl)-5-fluorobenzonitrile | —C$_6$H$_4$—Cl | —C$_6$H$_4$—CN | 476 (M+1, $^{35}$Cl), 478 (M+1, $^{37}$Cl). |

-continued

| Example | Name | Ar | R4 | Mass Spectrum m/e |
|---|---|---|---|---|
| 129 | 3-((1R)-1-{1-[(S)-(4-chlorophenyl)(3-cyanophenyl)methyl]azetidin-3-yl}-2-fluoro-2-methylpropyl)-5-fluorobenzonitrile | 4-Cl-C6H4- | 3-CN-C6H4- | 476 (M+1, $^{35}$Cl), 478 (M+1, $^{37}$Cl). |
| 130 | 3-((1S)-1-{1-[(R)-(4-chlorophenyl)(3-cyanophenyl)methyl]azetidin-3-yl}-2-fluoro-2-methylpropyl)-5-fluorobenzonitrile | 4-Cl-C6H4- | 3-CN-C6H4- | 476 (M+1, $^{35}$Cl), 478 (M+1, $^{37}$Cl). |
| 131 | 3-{1-[1-(diphenylmethyl)azetidin-3-yl]-2-fluoro-2-methylpropyl}-5-fluorobenzonitrile | C6H5- | C6H5- | 417 (M+1) |
| 132 | 3-{(1S)-1-[1-(diphenylmethyl)azetidin-3-yl]-2-fluoro-2-methyl-propyl}-5-fluorobenzonitrile | C6H5- | C6H5- | 417 (M+1) |
| 133 | 3-{(1R)-1-[1-(diphenylmethyl)azetidin-3-yl]-2-fluoro-2-methyl-propyl}-5-fluorobenzonitrile | C6H5- | C6H5- | 417 (M+1) |
| 134 | 3-(1-{1-[(3-bromophenyl)(4-cyanophenyl)methyl]azetidin-3-yl}-2-fluoro-2-methylpropyl)-5-fluorobenzonitrile | 4-CN-C6H4- | 3-Br-C6H4- | 520 (M+1, $^{79}$Br), 522 (M+1, $^{81}$Br). |
| 135 | 3-((1S)-1-{1-[(S)-(3-bromophenyl)(4-cyanophenyl)methylazetidin-3-yl-}-2-fluoro-2-methylpropyl)-5-fluorobenzonitrile | 4-CN-C6H4- | 3-Br-C6H4- | 520 (M+1, $^{79}$br), 522 (M+1, $^{81}$Br). |
| 136 | 3-((1R)-1-{1-[(R)-(3-bromophenyl)(4-cyanophenyl)methyl]azetidin-3-yl}-2-fluoro-2-methylpropyl)-5-fluorobenzonitrile | 4-CN-C6H4- | 3-Br-C6H4- | 520 (M+1, $^{79}$Br), 522 (M+1, $^{81}$Br). |
| 137 | 3-((1S)-1-{1-[(R)-(3-bromophenyl)(4-cyanophenyl)methyl]azetidin-3-yl}-2-fluoro-2-methylpropyl)-5-fluorobenzonitrile | 4-CN-C6H4- | 3-Br-C6H4- | 520 (M+1, $^{79}$br), 522 (M+1, $^{81}$Br). |
| 138 | 3-((1R)-1-{1-[(S)-(3-bromophenyl)(4-cyanophenyl)methyl]azetidin-3-yl}-2-fluoro-2-methylpropyl)-5-fluorobenzonitrile | 4-CN-C6H4- | 3-Br-C6H4- | 520 (M+1, $^{79}$Br), 522 (M+1, $^{81}$Br). |
| 139 | 3-(1-{1-[(3-cyanophenyl)(4-cyanophenyl)methyl]azetidin-3-yl}-2-fluoro-2-methylpropyl)-5-fluorobenzonitrile | 4-CN-C6H4- | 3-CN-C6H4- | 467 (M+1) |

-continued

| Example | Name | Ar | R4 | Mass Spectrum m/e |
|---|---|---|---|---|
| 140 | 3-((1S)-1-{1-[(S)-(3-cyanophenyl)(4-cyanophenyl)methyl]azetidin-3-yl}-2-fluoro-2-methylpropyl)-5-fluorobenzonitrile | —C₆H₄—CN | —C₆H₄—CN (3-CN) | 467 (M+1) |
| 141 | 3-((1R,S)-1-{1-[(R)-(3-cyanophenyl)(4-cyanophenyl)methyl]azetidin-3-yl}-2-fluoro-2-methylpropyl)-5-fluorobenzonitrile | —C₆H₄—CN | —C₆H₄—CN (3-CN) | 467 (M+1) |
| 142 | 3-((1R)-1-{1-[(S)-(3-cyanophenyl)(4-cyanophenyl)methyl]azetidin-3-yl}-2-fluoro-2-methylpropyl)-5-fluorobenzonitrile | —C₆H₄—CN | —C₆H₄—CN (3-CN) | 467 (M+1) |
| 143 | 3-((1S)-1-{1-[(R)-(3-cyanophenyl)(4-cyanophenyl)methyl]azetidin-3-yl}-2-fluoro-2-methylpropyl)-5-fluorobenzonitrile | —C₆H₄—CN | —C₆H₄—CN (3-CN) | 467 (M+1) |

EXAMPLE 144

EXAMPLE 145

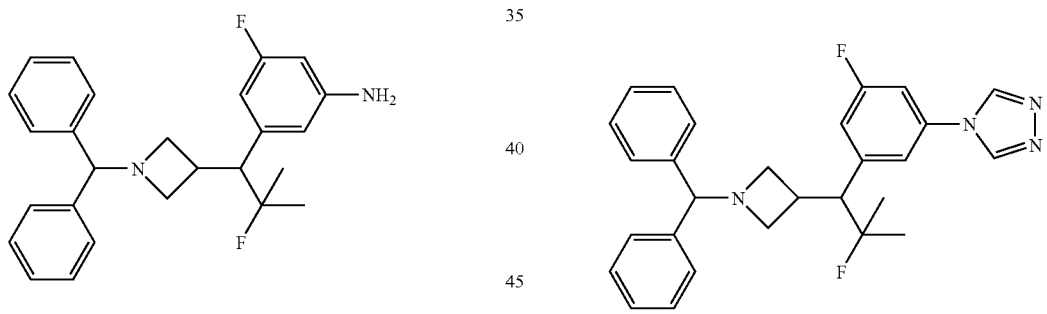

(3-{1-[1(Diphenylmethyl)azetidin-3-yl]-2-fluoro-2-methylpropyl}-5-fluorophenyl)amine 4-(3-{1-[1-(Diphenylmethyl)azetidin-3-yl]-2-fluoro-2-methylpropyl}-5-fluorophenyl)-4H-1,2,4-trizole A mixture of 105 mg (0.24 mmole) of 3-[1-3-bromo-5-fluorophenyl)-2-fluoro-2-methylpropyl]-1-(diphenylmethyl)azetidine, 2 mg (0.005 mmole) of 1,1'-Bis(diphenylphosphino)ferrocene and 2.2 mg (0.0024 mmole) of tris(dibenzylideneacetone)dipalladium(0) in 2 mL of dry THF was degassed three times. Then 0.36 mL of a 1M solution of LHMDS in THF was added and the solution was stirred at 65° C. for 15 h. After the solution had cooled to rt, 1 mL of 1M HCl was added and the solution was stirred at rt. After 5 min, the pH of the solution was adjusted to 7.5 with 1M NaOH and the layers were separated. The aqueous layer was washed with 20 ML of 1:1 ether-ethyl acetate and the combined organic layers were dried over Na₂SO₄ and concentrated to afford the title compound; Mass Spectrum: m/e=407 (M+1).

A solution of 0.364 g (0.897 mmole) of (3-{1-[1-(Diphenylmethyl)azetidin-3-yl]-2-fluoro-2-methylpropyl}-5-fluorophenyl)amine, 574 mg (4.04 mmole) N'-[(1E)-(dimethylamino)methylene]-N,N-dimethylhydrazonoformamide and 136 mg (0.72 mmole) p-toluenesulfonic acid monohydrate in 6 mL was heated at reflux for 36 h. The solution was concentrated under vacuum and the residue was dissolved in ether. The ether layer was shaken with two 20 mL portions of saturated NaHCO₃ solution and then dried over Na₂SO₄ and concentrated. The residue was purified by flash chromatography using CH₂Cl₂-EtOAc-NH₃ (2M in MeOH), 200:50:4 to afford the title compound as a white solid: Mass Spectrum: m/e=459 (M+1).

EXAMPLE 146

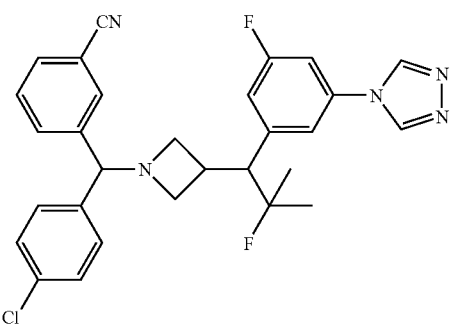

3-[(4-Chlorophenyl)(3-{2-fluoro-1-[3-fluoro-5-4H-1,2,4-triazol-4-yl)phenyl]-2-methylpropyl}azetidin-1-yl)methyl]benzonitrile Step 1 4-[3-(1-Azetidin-3-yl-2-fluoro-2-methylpropyl)-5-fluorophenyl]-4H-1,2,4-triazole hydrochloride A mixture of 190 mg (0.41 mmole) of 4-(3-{1-[1-(diphenylmethyl)azetidin-3-yl]-2-fluoro-2-methylpropyl}-5-fluorophenyl)-4H-1,2,4-triazole and 180 mg of 10% Pd/C in 6 mL of CH₃OH and 0.83 mL of 1M HCL in ether was shaken under 40 psi H₂. After 24 h, the mixture was filtered through CELITE and the filtrate was concentrated. The residue was triturated with three 50 mL portions of 2:1 hexane-ether and filtered to afford the title compound as a white solid; Mass Spectrum: m/e=293 (M+1).

Step 2 3-[(4-Chlorophenyl)(3-{2-fluoro-1-[3-fluoro-5-(4H-1,2,4-triazol-4-yl)phenyl]-2-methylpropyl}azetidin-1-yl)methyl]benzonitrile A sample of 135 mg (0.41 mmole) of 4-[3-(1-Azetidin-3-yl-2-fluoro-2-methylpropyl)-5-fluorophenyl]-4H-1,2,4-triazole hydrochloride, 211 mg (0.62 mmole) of 3-[bromo(4-chlorophenyl)methyl]benzonitrile and 181 uL (1.025 mmole) of diisopropylethylamine in 5 mL of dry CH₃CN was heated at reflux for 3 h.

The solution was concentrated and the residue was dissolved in 20 mL of CH₂Cl₂ and 5 mL of NaHCO₃. The layers were separated and the organic phase was dried over Na₂SO₄ and concentrated. The residue was purified on silica gel using CH₂Cl₂-EtOAc-NH₃ (2M in MeOH), 200:50:4 to afford the title compound as a mixture of 4 diastereomers: Mass Spectrum: m/e=518 (M+1).

EXAMPLE 147

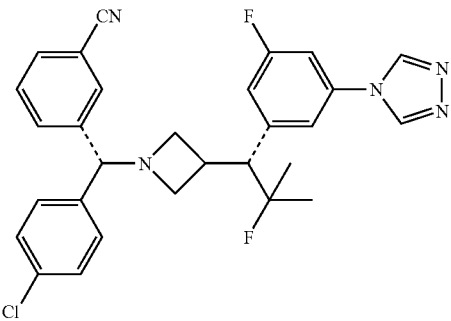

3-[(R)-(4-chlorophenyl)(3-{(1R)-2-fluoro-1-[3-fluoro-5-(4H-1,2,4-triazol-4-yl)phenyl]-2-methylpropyl}azetidin-1-yl)methyl]benzonitrile The product from Step 3 of Example 146 was purified on a ChiralPak AK column using 20% isopropanol-heptane to afford the title compound; Mass Spectrum: m/e=518 (M+1).

EXAMPLE 148

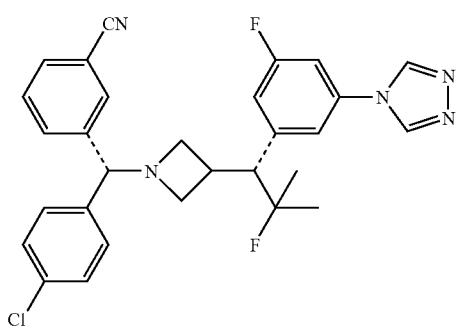

3-[(SR)-(4-chlorophenyl)(3-{(1RS)-2-fluoro-1-[3-fluoro-5-(4H-1,2,4-triazol-4-yl)phenyl]-2-methylpropyl}azetidin-1-yl)methyl]benzonitrile Further elution of the ChiralPak AK column in Example 147 with 20% isopropanol-heptane to afford the title compound as a mixture of enantiomers; Mass Spectrum: m/e=518 (M+1).

EXAMPLE 149

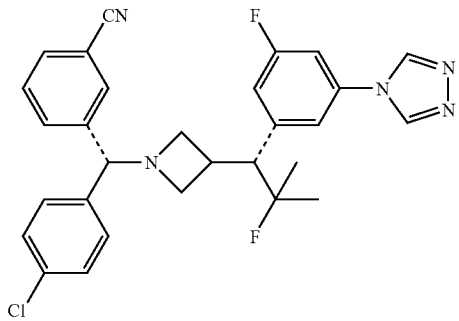

3-[(R)-(4-chlorophenyl)(3-{(1R)-2-fluoro-1-[3-fluoro-5-(4H-1,2,4-triazol)-4-yl)phenyl]-2-methylpropyl}azetidin-1-yl)methyl]benzonitrile Further elution of the ChiralPak AK column in Example 148 with 20% isopropanol-heptane to afford the title compound as a single enantiomer; Mass Spectrum: m/e=518 (M+1).

EXAMPLE 150

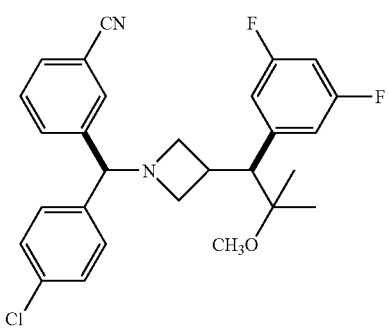

3-((S)-(4-chlorophenyl){3-[(1S)-1-(3,5-difluorophenyl)-2-methoxy-2-methylpropyl]azetidin-1-yl}methyl)benzonitrile A solution of 46.6 mg (0.1 mmole) of 3-((S)-(4-chlorophenyl){3-[(1S)-1-(3,5-difluorophenyl)-2-hydroxy-2-methylpropyl]azetidin-1-yl}methyl)benzonitrile in THF was cooled to −78° C. To this was added 0.3 mL of a 1M solution of NaHMDS in THF. After 10 minutes, 20 uL of iodomethane was added and the solution was allowed to warm to rt. The solution was partitioned between ethyl acetate and water and the organic layer was washed with brine, dried over MgSO$_4$ and concentrated. The residue was filtered through silica gel using 10% ethyl acetate-hexane to afford the title compound; $^1$H-NMR(CDCl$_3$) δ 1.07 (s, 3H), 1.14 (S, 3H), 2.28 (t, 1H, J=7.5 Hz), 2.74 (d, 1H, J=10.7 Hz), 2.82 (t, 1H, J=7.5 Hz), 3.10-3.16 (m, 2H), 3.19 (s, 1H), 3.62 (m, 1H), 4.29 (s, 1H), 6.67-6.73 (m, 3H), 7.21-7.4 (m, 8H);); Mass Spectrum: m/e=481 (M+1, $^{35}$Cl) and 483 (M+1, $^{37}$Cl).

EXAMPLE 151-153

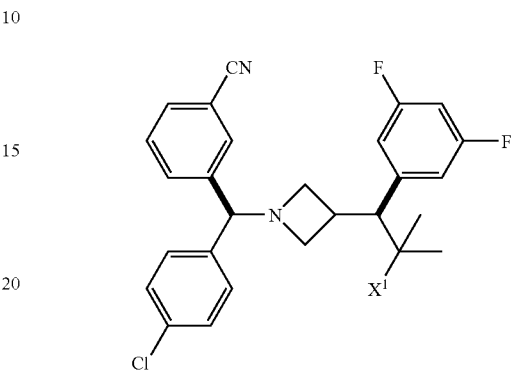

The following Examples were prepared from 3-((S)-(4-chlorophenyl){3-[(1S)-1-(3,5-difluorophenyl)-2-hydroxy-2-methylpropyl]azetidin-1-yl}methyl)benzonitrile using the procedure described in Example 150.

| Example | Name | X$^1$ | Mass Spectrum m/e |
|---|---|---|---|
| 151 | (2S)-2-{1-[(S)-(4-Chlorophenyl)(3-cyanophenyl)methyl]azetidin-3-yl}-2-(3,5-difluorophenyl)-1,1-dimethylethyl dimethylcarbamate | | 538 (M+1, $^{35}$Cl); 540 (M+1, $^{37}$Cl) |
| 152 | 3-[(S)-{3-[(1S)-2-(Allyloxy)-1-(3,5-difluoropheenyl)-2-methylpropyl]azetidin-1-yl}(4-chaloorphenyl)methyl]benzonitrile | | 507 (M+1, $^{35}$Cl); 509 (M+1, $^{37}$Cl) |
| 153 | tert-Butyl [(2S)-2-{1-[(S)-(4-chlorophenyl)(3-cyanophenyl)methyl]azetidin-3-yl}-2-(3,5-difluorophenyl)-1,1-dimethylethoxy]acetate | | 581 (M+1, $^{35}$Cl); 583 (M+1, $^{37}$Cl) |

BIOLOGICAL EXAMPLE 1

Cannabinoid Receptor-1 (CB1) Binding Assay

Binding affinity determination is based on recombinant human CB1 receptor expressed in Chinese Hamster Ovary (CHO) cells (Felder et al, Mol. Pharmacol. 48: 443-450, 1995). Total assay volume is 250 μL (240 μL CB1 receptor membrane solution plus 5 μL test compound solution plus 5 μL [3H]CP-55940 solution). Final concentration of [3H]CP-55940 is 0.6 nM. Binding buffer contains 50 mM Tris-HCl, pH7.4, 2.5 mM EDTA, 5mM MgCl$_2$, 0.5 mg/mL fatty acid free bovine serum albumin and protease inhibitors (Cat#P8340, from Sigma). To initiate the binding reaction, 5 μL of radioligand solution is added, the mixture is incubated with gentle shaking on a shaker for 1.5 hours at 30° C. The binding is terminated by using 96-well harvester and filtering through GF/C filter presoaked in 0.05% polyethylenimine. The bound radiolabel is quantitated using scintillation counter. Apparent binding affinities for various compounds are calculated from $IC_{50}$ values (DeBlasi et al., Trends Pharmacol Sci 10: 227-229, 1989).

The binding assay for CB2 receptor is done similarly with recombinant human CB2 receptor expressed in CHO cells.

CB1 antagonist/inverse agonist compounds of the present invention have $IC_{50}s$ of less than 1 micromolar in the CB1 binding assay. Selective CB1 antagonist/inverse agonist compounds have IC50s 100-fold greater in the CB2 binding assay than in the CB1 assay, and generally have IC50s of greater than one micromolar in the CB2 binding assay.

BIOLOGICAL EXAMPLE 2

Cannabinoid Receptor-1 (CB1) Functional Activity Assay

The functional activation of CB1 receptor is based on recombinant human CB1 receptor expressed in CHO cells (Felder et al, Mol. Pharmacol. 48: 443-450, 1995). To determine the agonist activity or inverse agonist activity of any test compound, 50 μL of CB 1-CHO cell suspension are mixed with test compound and 70 uL assay buffer containing 0.34 mM 3-isobutyl-1-methylxanthine and 5.1 μM of forskolin in 96-well plates. The assay buffer is comprised of Earle's Balanced Salt Solution supplemented with 5 mM $MgCl_2$, 1 mM glutamine, 10 mM HEPES, and 1 mg/mL bovine serum albumin. The mixture is incubated at room temperature for 30 minutes, and terminated by adding 30 μl/well of 0.5M HCl. The total intracellular cAMP level is quantitated using the New England Nuclear Flashplate and cAMP radioimmunoassay kit.

To determine the antagonist activity of test compound, the reaction mixture also contains 0.5 nM of the agonist CP55940, and the reversal of the CP55940 effect is quantitated. Alternatively, a series of dose response curves for CP55940 is performed with increasing concentration of the test compound in each of the dose response curves.

The functional assay for the CB2 receptor is done similarly with recombinant human CB2 receptor expressed in CHO cells.

CB1 antagonist/inverse agonist compounds of the present invention generally have EC50s of less than 1 micromolar in the CB1 functional assay and selective CB1 antagonist/inverse agonists have generally have EC50s of greater than 1 micromolar in the CB2 functional assay.

BIOLOGICAL EXAMPLE 3

Acute Food Intake Studies in Rats or Mice: General Procedure

Adult rats or mice are used in these studies. After at least 2 days of acclimation to the vivarium conditions (controlled humidity and temperature, lights on for 12 hours out of 24 hours) food is removed from rodent cages. Experimental compounds or their vehicles are administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the compounds are compared to the effect of vehicle. In these experiments many strains of mouse or rat, and several standard rodent chows can be used.

BIOLOGICAL EXAMPLE 4

Chronic Weight Reduction Studies in Rats or Mice: General Procedure

Adult rats or mice are used in these studies. Upon or soon after weaning, rats or mice are made obese due to exclusive access to diets containing fat and sucrose in higher proportions than in the control diet. The rat strains commonly used include the Sprague Dawley bred through Charles River Laboratories. Although several mouse strains may be used, c57B1/6 mice are more prone to obesity and hyperinsulinemia than other strains. Common diets used to induce obesity include: Research Diets D12266B (32% fat) or D12451 (45% fat) and BioServ S3282 (60% fat). The rodents ingest chow until they are significantly heavier and have a higher proportion of body fat than control diet rats, often 9 weeks. The rodents receive injections (1 to 4 per day) or continuous infusions of experimental compounds or their vehicles either orally, intraperitoneally, subcutaneously or intravenously. Food intake and body weights are measured daily or more frequently. Food intake is calculated as grams of food eaten per gram of body weight within each time interval and the appetite-suppressant and weight loss effects of the compounds are compared to the effects of vehicle.

BIOLOGICAL EXAMPLE 5

Tail Suspension Test

The tail suspension test has been widely used for screening antidepressant-like effects of compounds in mice (Steru et al., 1987), rats (Izumi et al, 1997) and gerbils (Varty et al., 2003). It is based on the principle that helplessness takes place when the animal is exposed to a sustained aversive situation. Briefly, when the animal is suspended by its tail it exhibits several escape-oriented behaviors intercalated with bouts of immobility that evolve with time into complete immobility. Pretreatment with a wide range of antidepressants, such as tricyclic compounds, monoamine uptake blockers, or serotonin reuptake inhibitors (SSRIs), significantly decrease duration of immobility throughout the test, while anxiolytics or antipsychotics do not (Wong et al., 2000; Oxenkrug 1999).

Subjects

Male mice are housed in a colony room maintained at constant temperature (22° C.) and humidity (30-70%), with food (Harlan Teklad Diet #7012, 5% fat; 3.75 kcal/gm) and water available ad libitum. For the behavioral experiments, mice are group housed (10/cage) under a reversed light/dark cycle (lights on at 21:00 h, off at 09:00 h) and tests occurred between 10:00 h and 14:00 h.

Drugs

The compounds of formula (I) are solubilized into 1% Tween80-saline solution, addition of DMSO may be employed to increase solubility. Compounds are dosed intraperitoneally in a volume of 0.1 mL.

Tail Suspension Test

An automated tail-suspension apparatus (TSE Systems, Bad Homburg, Germany) with a tail hanger connected to a precision linear load cell is used. One centimeter of the mouse's tail is inserted into the tail hanger and secured with non-irritating adhesive tape. Mice are suspended by the tail, at a height of 35 cm from the tabletop for 6 minutes. During this time the load cell records the mouse's movements and transmits the information to a central computer, which then records the rate of immobility within the course of the session, and calculates total duration of immobility. Total duration of immobility is used as the dependent variable in one-way Analysis of Variance (ANOVA) on treatment.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. 3-((1S)-1-{1-[(S)-(3-cyanophenyl)(4-cyanophenyl)methyl]azetidin-3-yl}-2-fluoro-2-methylpropyl)-5-fluorobenzonitrile; or a pharmaceutically acceptable salt thereof.

* * * * *